(12) United States Patent
Svanegaard et al.

(10) Patent No.: US 12,029,582 B2
(45) Date of Patent: Jul. 9, 2024

(54) ACCESSORY DEVICES OF A MEDICAL SYSTEM, AND RELATED METHODS FOR CHANGING A MEDICAL APPLIANCE BASED ON FUTURE OPERATING STATE

(71) Applicant: Coloplast A/S, Humlebaek (DK)

(72) Inventors: Mads Hindhede Svanegaard, Bagsvaerd (DK); Marie Svane Rizk Vestergaard, Frederiksberg (DK); Michael Larsen, Copenhagen (DK); Mikkel Broge Hendeliowitz, Copenhagen (DK); Tine Frimodt Hansen, Paris (FR)

(73) Assignee: Coloplast A/S, Humlebaek (DK)

( * ) Notice: Subject to any disclaimer, the term of this patent is extended or adjusted under 35 U.S.C. 154(b) by 995 days.

(21) Appl. No.: 16/970,970

(22) PCT Filed: Feb. 20, 2019

(86) PCT No.: PCT/DK2019/050059
§ 371 (c)(1),
(2) Date: Aug. 19, 2020

(87) PCT Pub. No.: WO2019/161863
PCT Pub. Date: Aug. 29, 2019

(65) Prior Publication Data
US 2021/0059603 A1    Mar. 4, 2021

(30) Foreign Application Priority Data
Feb. 20, 2018  (DK) .......................... PA 2018 70109

(51) Int. Cl.
G05B 99/00     (2006.01)
A61B 5/00      (2006.01)
(Continued)

(52) U.S. Cl.
CPC .......... A61B 5/4851 (2013.01); A61B 5/7435 (2013.01); A61F 5/4404 (2013.01);
(Continued)

(58) Field of Classification Search
CPC ........................................... G05B 2219/32128
See application file for complete search history.

(56) References Cited

U.S. PATENT DOCUMENTS 2,054,535 A   9/1936  Diack
2,327,514 A   8/1943  Fenwick
(Continued)

FOREIGN PATENT DOCUMENTS

CN    203786580 U    8/2014
CN    104902399 A    9/2015
(Continued)

OTHER PUBLICATIONS

International Preliminary Report on Patentability received for PCT Patent Application No. PCT/DK2019/050059, mailed on May 7, 2020, 14 pages.
(Continued)

Primary Examiner — Suresh Suryawanshi
(74) Attorney, Agent, or Firm — Coloplast Corp., Coloplast A/S; Nick Baumann

(57) ABSTRACT

The present disclosure relates to a method, performed in an accessory device, for monitoring the current operating state and the future operating state of a base plate of an ostomy appliance. The accessory device comprises an interface configured to communicate with one or more devices of an ostomy system. The interface comprises a display. The ostomy system comprises a monitor device, and/or the ostomy appliance configured to be placed on a skin surface of a user. The ostomy appliance comprises a base plate. The method comprises obtaining monitor data from the monitor
(Continued)

device; determining a current operating state of the ostomy appliance based on the monitor data; determining a future operating state of the ostomy appliance based on the monitor data and/or the current operating state; and displaying, on the display, a first user interface screen comprising a first primary user interface object representing the current operating state and/or a first secondary user interface object representing the future operating state.

28 Claims, 23 Drawing Sheets

(51) Int. Cl.
    *A61F 5/44*         (2006.01)
    *A61F 5/443*       (2006.01)
    *H04M 1/72409*   (2021.01)
    *A61F 5/445*       (2006.01)

(52) U.S. Cl.
    CPC ......... *A61F 5/443* (2013.01); *H04M 1/72409* (2021.01); *A61B 2560/0204* (2013.01); *A61B 2560/0487* (2013.01); *A61F 5/445* (2013.01); *G05B 2219/32128* (2013.01)

(56) References Cited

U.S. PATENT DOCUMENTS

| | | | |
|---|---|---|---|
| 2,542,233 | A | 2/1951 | Carroll |
| 2,544,579 | A | 3/1951 | Ardner |
| 3,214,502 | A | 10/1965 | Schaar |
| 3,832,510 | A | 8/1974 | Pfau et al. |
| 3,915,171 | A | 10/1975 | Shermeta |
| 3,941,133 | A | 3/1976 | Chen |
| 4,231,369 | A | 11/1980 | Sorensen et al. |
| 4,372,308 | A | 2/1983 | Steer et al. |
| 4,449,970 | A | 5/1984 | Bevan et al. |
| 4,668,227 | A | 5/1987 | Kay |
| 4,754,264 | A | 6/1988 | Okada et al. |
| 4,775,374 | A | 10/1988 | Cilento et al. |
| 4,834,731 | A | 5/1989 | Nowak et al. |
| 4,973,323 | A | 11/1990 | Kaczmarek et al. |
| 4,982,742 | A | 1/1991 | Claude |
| 5,013,307 | A | 5/1991 | Broida |
| 5,016,645 | A | 5/1991 | Williams et al. |
| 5,051,259 | A | 9/1991 | Olsen et al. |
| 5,074,851 | A | 12/1991 | Plass et al. |
| 5,111,812 | A | 5/1992 | Swanson et al. |
| 5,167,650 | A | 12/1992 | Johnsen et al. |
| 5,197,895 | A | 3/1993 | Stupecky |
| 5,237,995 | A | 8/1993 | Cano |
| 5,318,543 | A | 6/1994 | Ross et al. |
| 5,358,488 | A | 10/1994 | Suriyapa |
| 5,486,158 | A | 1/1996 | Samuelsen |
| 5,570,082 | A | 10/1996 | Mahgerefteh et al. |
| 5,593,397 | A | 1/1997 | La Gro |
| 5,626,135 | A | 5/1997 | Sanfilippo |
| 5,672,163 | A | 9/1997 | Ferreira et al. |
| 5,677,221 | A | 10/1997 | Tseng |
| 5,704,905 | A | 1/1998 | Jensen et al. |
| 5,790,036 | A | 8/1998 | Fisher et al. |
| 5,800,415 | A | 9/1998 | Olsen |
| 5,816,252 | A | 10/1998 | Faries, Jr. et al. |
| 5,834,009 | A | 11/1998 | Sawers et al. |
| 5,879,292 | A | 3/1999 | Sternberg et al. |
| 5,942,186 | A | 8/1999 | Sanada et al. |
| 6,015,399 | A | 1/2000 | Mracna et al. |
| 6,025,725 | A | 2/2000 | Gershenfeld et al. |
| 6,057,689 | A | 5/2000 | Saadat |
| 6,103,033 | A | 8/2000 | Say et al. |
| 6,135,986 | A | 10/2000 | Leisner et al. |
| 6,165,005 | A | 12/2000 | Mills et al. |
| 6,171,289 | B1 | 1/2001 | Millot et al. |
| 6,206,864 | B1 | 3/2001 | Kavanagh et al. |
| 6,246,330 | B1 | 6/2001 | Nielsen |
| 6,297,422 | B1 | 10/2001 | Hansen et al. |
| 6,407,308 | B1 | 6/2002 | Roe et al. |
| 6,433,244 | B1 | 8/2002 | Roe et al. |
| 6,482,491 | B1 | 11/2002 | Samuelsen et al. |
| 6,485,476 | B1 | 11/2002 | Von et al. |
| 6,520,943 | B1 | 2/2003 | Wagner |
| 6,659,989 | B1 | 12/2003 | Otto |
| 6,677,859 | B1 | 1/2004 | Bensen |
| 6,764,474 | B2 | 7/2004 | Nielsen et al. |
| 7,049,478 | B1 | 5/2006 | Smith |
| 7,066,919 | B1 | 6/2006 | Sauerland et al. |
| 7,150,728 | B2 | 12/2006 | Hansen et al. |
| 7,166,091 | B1 | 1/2007 | Zeltner |
| 7,199,501 | B2 | 4/2007 | Pei et al. |
| 7,214,217 | B2 | 5/2007 | Pedersen et al. |
| 7,221,279 | B2 | 5/2007 | Nielsen |
| 7,326,190 | B2 | 2/2008 | Botten |
| 7,341,578 | B2 | 3/2008 | Bulow et al. |
| 7,347,844 | B2 | 3/2008 | Cline et al. |
| 7,367,965 | B2 | 5/2008 | Poulsen et al. |
| 7,422,578 | B2 | 9/2008 | Shan et al. |
| 7,559,922 | B2 | 7/2009 | Botten |
| 7,625,362 | B2 | 12/2009 | Boehringer et al. |
| 7,641,612 | B1 | 1/2010 | McCall |
| 7,670,289 | B1 | 3/2010 | McCall |
| 7,943,812 | B2 | 5/2011 | Stroebeck et al. |
| 7,981,098 | B2 | 7/2011 | Boehringer et al. |
| 8,061,360 | B2 | 11/2011 | Locke et al. |
| 8,277,427 | B2 | 10/2012 | Edvardsen et al. |
| 8,319,003 | B2 | 11/2012 | Olsen et al. |
| 8,398,575 | B1 | 3/2013 | McCall |
| 8,398,603 | B2 | 3/2013 | Thirstrup et al. |
| 8,399,732 | B2 | 3/2013 | Oelund et al. |
| 8,409,158 | B2 | 4/2013 | Edvardsen et al. |
| 8,449,471 | B2 | 5/2013 | Tran |
| 8,474,338 | B2 | 7/2013 | Gelman et al. |
| 8,500,718 | B2 | 8/2013 | Locke et al. |
| 8,632,492 | B2 | 1/2014 | Delegge |
| 8,680,991 | B2 | 3/2014 | Tran |
| 8,684,982 | B2 | 4/2014 | Nguyen-Demary et al. |
| 8,740,865 | B2 | 6/2014 | Krystek et al. |
| 8,795,257 | B2 | 8/2014 | Coulthard et al. |
| D712,545 | S | 9/2014 | Igwebuike et al. |
| 8,821,464 | B2 | 9/2014 | Hanuka et al. |
| 8,975,465 | B2 | 3/2015 | Hong et al. |
| 8,979,813 | B2 | 3/2015 | Uveborn |
| 9,046,085 | B2 | 6/2015 | Schoess et al. |
| 9,066,812 | B2 | 6/2015 | Edvardsen et al. |
| 9,216,104 | B2 | 12/2015 | Thirstrup et al. |
| 9,308,332 | B2 | 4/2016 | Heppe |
| 9,322,797 | B1 | 4/2016 | Lastinger et al. |
| 9,629,779 | B2 | 4/2017 | Grum-Schwensen et al. |
| 9,629,964 | B2 | 4/2017 | Wuepper |
| 9,693,908 | B2 | 7/2017 | Eriksson et al. |
| 9,770,359 | B2 | 9/2017 | Edvardsen et al. |
| 9,788,991 | B2 | 10/2017 | Bird |
| 9,867,934 | B2 | 1/2018 | Heppe |
| 9,928,341 | B2 | 3/2018 | Angelides |
| 10,016,298 | B2 | 7/2018 | Thirstrup et al. |
| D826,740 | S | 8/2018 | Stevens et al. |
| 10,500,084 | B2 | 12/2019 | Hansen et al. |
| 10,531,977 | B2 | 1/2020 | Schoess et al. |
| 10,646,370 | B2 | 5/2020 | Keleny et al. |
| 10,792,184 | B2 | 10/2020 | Hvid et al. |
| 10,799,385 | B2 | 10/2020 | Hansen et al. |
| 10,849,781 | B2 | 12/2020 | Hansen et al. |
| 10,874,541 | B2 | 12/2020 | Seres et al. |
| 10,987,243 | B2 | 4/2021 | Thirstrup et al. |
| 11,096,818 | B2 | 8/2021 | Thirstrup et al. |
| 11,135,084 | B2 | 10/2021 | Seres et al. |
| 11,306,224 | B2 | 4/2022 | Chatterjee et al. |
| 11,406,525 | B2 | 8/2022 | Seres et al. |
| 11,471,318 | B2 | 10/2022 | Hansen et al. |
| 11,491,042 | B2 | 11/2022 | Seres et al. |
| 11,534,323 | B2 | 12/2022 | Hansen et al. |
| 11,540,937 | B2 | 1/2023 | Hansen et al. |
| 11,547,595 | B2 | 1/2023 | Hansen et al. |
| 11,547,596 | B2 | 1/2023 | Hansen et al. |

(56) References Cited

U.S. PATENT DOCUMENTS

| | | |
|---|---|---|
| 11,559,423 B2 | 1/2023 | Speiermann et al. |
| 11,559,426 B2 | 1/2023 | Sletten et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries, Jr. et al. |
| 2006/0271002 A1 | 11/2006 | Botten |
| 2007/0010256 A1 | 1/2007 | Klabunde et al. |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1 | 2/2010 | Thirstrup et al. |
| 2010/0036206 A1 | 2/2010 | Lorio |
| 2010/0072271 A1 | 3/2010 | Thorstensson |
| 2010/0076275 A1 | 3/2010 | Chu et al. |
| 2010/0311167 A1 | 12/2010 | Wood et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0128815 A1* | 5/2014 | Cabiri ............... A61M 5/14248 604/180 |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0351690 A1 | 12/2015 | Toth et al. |
| 2015/0374896 A1 | 12/2015 | Du et al. |
| 2016/0015570 A1 | 1/2016 | Heinecke et al. |
| 2016/0058604 A1 | 3/2016 | Wiltshire et al. |
| 2016/0084869 A1 | 3/2016 | Yuen et al. |
| 2016/0117062 A1* | 4/2016 | Hussam ................. A61B 34/25 715/763 |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0178387 A1* | 6/2016 | Yamasaki ............... G01C 21/20 701/428 |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mrtensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | DiMaio et al. |
| 2017/0079576 A1 | 3/2017 | Stroebech et al. |
| 2017/0098044 A1 | 4/2017 | Lai et al. |
| 2017/0112658 A1 | 4/2017 | Hosono |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0319073 A1 | 11/2017 | DiMaio et al. |
| 2017/0340474 A1 | 11/2017 | Thirstrup et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0171183 A1 | 6/2018 | Sakurai et al. |
| 2018/0177626 A1 | 6/2018 | Israelson |

(56) References Cited

U.S. PATENT DOCUMENTS

| | | |
|---|---|---|
| 2018/0250156 A1 | 9/2018 | Lam |
| 2018/0298240 A1 | 10/2018 | Chatterjee et al. |
| 2018/0344533 A1 | 12/2018 | Rovaniemi |
| 2019/0008439 A1 | 1/2019 | Sageder et al. |
| 2019/0099552 A1 | 4/2019 | Zhang et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0000652 A1 | 1/2022 | Thirstrup et al. |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0378602 A1 | 12/2022 | Hansen et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0145670 A1 | 5/2023 | Seres et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19900611 C1 | 7/2000 |
| DE | 69722993 | 7/2003 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0800804 A1 | 10/1997 |
| EP | 1275357 A2 | 1/2003 |
| EP | 1188157 B1 | 12/2005 |
| EP | 2108345 A1 | 10/2009 |
| EP | 2000083 B1 | 8/2012 |
| EP | 2489561 A2 | 8/2012 |
| EP | 2601915 A1 | 6/2013 |
| EP | 2654646 A2 | 10/2013 |
| EP | 2738960 A1 | 6/2014 |
| EP | 2453851 B1 | 10/2014 |
| EP | 3064179 A1 | 9/2016 |
| EP | 3213727 A1 | 9/2017 |
| EP | 3226946 A1 | 10/2017 |
| GB | 2219679 A | 12/1989 |
| GB | 2225951 A | 6/1990 |
| GB | 2308306 B | 9/1999 |
| GB | 2343628 A1 | 5/2000 |
| GB | 2465742 A | 6/2010 |
| GB | 2486968 B | 2/2015 |
| GB | 2542093 A | 3/2017 |
| GB | 2561193 B | 9/2020 |
| JP | 04-074882 A | 3/1992 |
| JP | 06-152077 A | 5/1994 |
| JP | 09-010184 A | 1/1997 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2009519751 A | 5/2009 |
| JP | 2014-033745 A | 2/2014 |
| JP | 2014-054368 A | 3/2014 |

(56) References Cited

FOREIGN PATENT DOCUMENTS

| | | |
|---|---|---|
| JP | 2014-507182 A | 3/2014 |
| KR | 101056989 B1 | 8/2011 |
| KR | 10-2012-0003987 A | 1/2012 |
| KR | 200485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007070266 A1 | 6/2007 |
| WO | 2007098762 A1 | 9/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/112912 A2 | 9/2009 |
| WO | 2009107011 A1 | 9/2009 |
| WO | 2011/003421 A1 | 1/2011 |
| WO | 2011/004165 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012084987 A2 | 6/2012 |
| WO | 2013/013197 A1 | 1/2013 |
| WO | 2013095231 A1 | 6/2013 |
| WO | 2014/004207 A1 | 1/2014 |
| WO | 2014/086369 A1 | 6/2014 |
| WO | 2015007284 A1 | 1/2015 |
| WO | 2015/014774 A1 | 2/2015 |
| WO | 2015/084462 A1 | 6/2015 |
| WO | 2015/094064 A1 | 6/2015 |
| WO | WO-2015173395 A1 * | 11/2015 ........... A61B 5/0079 |
| WO | 2015187366 A1 | 12/2015 |
| WO | 2016132738 A1 | 8/2016 |
| WO | 2016/166731 A1 | 10/2016 |
| WO | 2016162038 A1 | 10/2016 |
| WO | 2016192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017074505 A1 | 5/2017 |
| WO | 2017/088153 A1 | 6/2017 |
| WO | 2017088053 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019094635 A1 | 5/2019 |
| WO | 2019120432 A1 | 6/2019 |
| WO | 2019/161863 A1 | 8/2019 |
| WO | 2019161859 A1 | 8/2019 |
| WO | 2019161860 A1 | 8/2019 |
| WO | 2019174693 A1 | 9/2019 |
| WO | 2019174695 A1 | 9/2019 |
| WO | 2019213623 A1 | 11/2019 |
| WO | 2020035121 A1 | 2/2020 |

OTHER PUBLICATIONS

International Search Report and Written Opinion received for PCT Patent Application No. PCT/DK2019/050059, mailed on Apr. 16, 2019, 11 pages.

* cited by examiner

Tigger times of first electrode pair [h]

ACCESSORY DEVICES OF A MEDICAL SYSTEM, AND RELATED METHODS FOR CHANGING A MEDICAL APPLIANCE BASED ON FUTURE OPERATING STATE

CROSS-REFERENCE TO RELATED APPLICATION

This application is a U.S. 371 Patent Application of International Application No. PCT/DK2019/050059, filed 20 Feb. 2019, which claims priority to Denmark Provisional Application No. PA 2018 70109, filed 20 Feb. 2018, both of which are incorporated herein by reference in their entireties for all purposes.

The present disclosure relates to an ostomy system, devices thereof and method for monitoring an ostomy appliance. The ostomy appliance system comprises an ostomy appliance and an ostomy monitor device. In particular, the present disclosure relates to communicating a future operating state of an ostomy appliance, so as to e.g. change an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
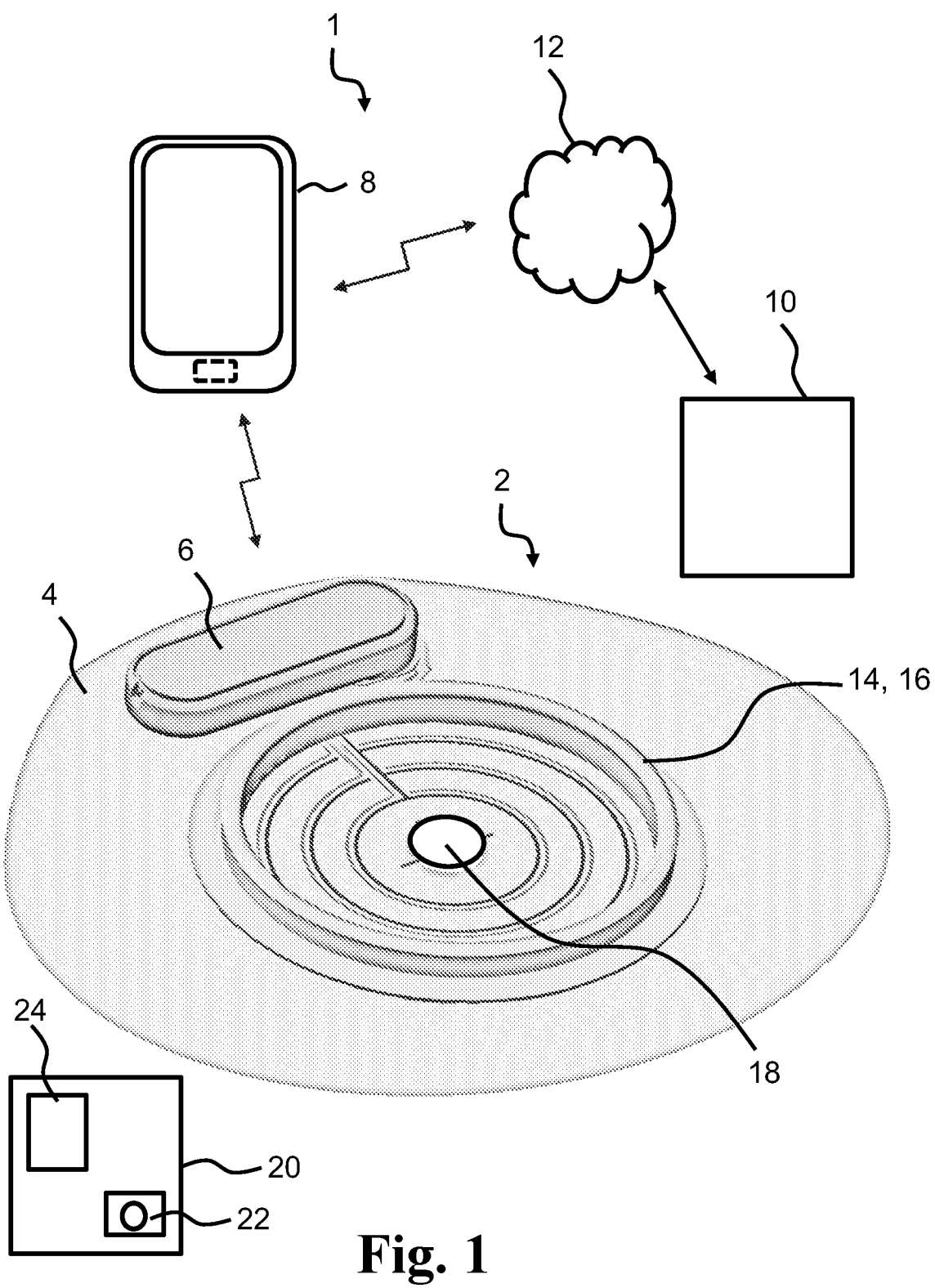
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

An ostomy system comprising an ostomy appliance and a monitor device, the ostomy appliance comprising a base plate is disclosed, wherein the monitor device is a monitor device as described herein.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of erosion and/or swelling in the adhesive material provided for attaching the base plate to the skin surface of a user. Depending on the nature of the erosion/swelling pattern in the adhesive, the ostomy system and devices thereof enable providing information to the user about the operating state of the base plate, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

A base plate for an ostomy appliance is disclosed, the base plate comprising a first adhesive layer with a proximal side configured for attachment of the base plate to the skin surface of a user, the first adhesive layer having a stomal opening with a center point; and a plurality of electrodes including a ground electrode, a first electrode, and a optionally a second electrode, the ground electrode comprising a ground connection part, the first electrode comprising a first connection part, and the second electrode comprising a second connection part, wherein the ground electrode forms a ground for the first electrode and/or the second electrode.

The base plate comprises a first adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer has a stomal opening with a center point or is at least prepared for forming a stomal opening with a center point. A base plate with three electrodes having sensing parts with contact to the first adhesive layer allows for determining erosion/swelling properties or characteristics of the first adhesive layer and/or determining a degree of erosion and/or swelling of the first adhesive layer.

It is an advantage of the present disclosure that an optimum or improved use of an ostomy appliance is provided. In particular, the present disclosure facilitates that a base plate is not changed too early (leading to increased cell-stripping from the skin and increased risk of skin damage and further leading to increased costs and/or material waste) nor too late (leading to adhesive failure, leakage and/or skin damage from the aggressive output). Accordingly, the user or a health care professional is able to monitor and plan the use of the ostomy appliance.

Further, determination of erosion/swelling and classification of operating states of the ostomy appliance is useful in helping to reduce the risk of a user experiencing leakage from an ostomy appliance. Further, determination of degrees of erosion/swelling and classification of operating states of the ostomy appliance is further useful in helping reduce the risk of skin damage to a user. In particular, determination of degrees of erosion and/or swelling according to the present disclosure may help provide a clear distinction or differentiation between adhesive failure, leakage of output, which is harmful to the skin, and a sweating ostomate.

The present disclosure provides a simple, efficient, and easy-to-use ostomy appliance system with a high degree of comfort for a user.

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is configured to overlap a (sensing) part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap (sensing) parts of an electrode and the primary second sensor point openings configured to overlap (sensing) parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap (sensing) parts of an electrode and the secondary second sensor point openings configured to overlap (sensing) parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap (sensing) parts of an electrode and the tertiary second sensor point openings configured to overlap (sensing) parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene.

The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground or reference for the first electrode. The ground electrode may comprise a second electrode part. The second electrode part of the ground electrode may form a ground or reference for the second electrode. The ground electrode may comprise a third electrode part. The third electrode part of the ground electrode may form a ground or reference for the third electrode. The ground electrode may comprise a fourth electrode part. The fourth electrode part of the ground electrode may form a ground or reference for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

An electrode may comprise a sensing part or a plurality of sensing parts, i.e. the part(s) of an electrode that are used for sensing. The first electrode may comprise a first sensing part. The first sensing part may contact the first adhesive layer and is optionally arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part. The second sensing part may contact the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate with a ground electrode, a first electrode, a second electrode, and a third electrode allows for a failsafe base plate in case e.g. the first electrode is cut or otherwise destroyed during preparation of the base plate.

The base plate may comprise a fourth electrode comprising a fourth connection part. The ground electrode may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm The base plate may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be equal to or larger than the fourth radial distance. The fifth radial distance(s) may be in the range from 25 mm to 50 mm, such as about 30 mm.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The base plate may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer.

One or more electrodes may be formed, e.g. printed, on the distal side of the support layer. Thus, one or more electrodes may be arranged between the support layer and the first adhesive layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a (sensing) part of the ground electrode and/or a (sensing) part of the fourth electrode. A secondary sensor point opening may overlap a (sensing) part of the fourth electrode and/or a (sensing) part of the fifth electrode. A tertiary sensor point opening may overlap a (sensing) part of the fifth electrode and/or a (sensing) part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode.

The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes (connection parts) of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor and one or more interfaces. The monitor device may comprise a memory for storing ostomy data.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The present disclosure relates to a method, performed in an accessory device, for monitoring the current operating state and the future operating state of a base plate of an ostomy appliance (e.g. a base plate disclosed herein) so as to assist a timely change of an ostomy appliance. The method disclosed herein may be performed for anticipating change of a base plate to a user.

The accessory device comprises an interface configured to communicate with one or more devices of an ostomy system (e.g. an ostomy system disclosed herein). The interface comprises a display. The ostomy system comprises a monitor device, and/or the ostomy appliance configured to be placed on a skin surface of a user. The ostomy appliance comprises a base plate.

The method comprises obtaining monitor data from the monitor device; determining a current operating state of the ostomy appliance based on the monitor data; determining a future operating state of the ostomy appliance based on the monitor data and/or the current operating state; and displaying, on the display, a first user interface screen comprising a first primary user interface object representing the current operating state and/or a first secondary user interface object representing the future operating state.

The ostomy appliance comprises a base plate, such as a base plate disclosed herein. The ostomy appliance comprises an ostomy pouch. The base plate may comprise a first adhesive layer having a proximal side. During use, a proximal surface of the first adhesive layer adheres to the user's skin in the peristomal area and/or to additional seals, such as sealing paste, sealing tape and/or sealing ring. The base plate may comprise one or more electrodes configured to measure electrical properties of the first adhesive layer. The electrical properties may be indicative of a conductive path in the first adhesive layer, thereby indicative of the moisture level, and indicative of the condition of the ostomy appliance.

The monitor data may be indicative of a condition of the ostomy appliance. The condition of the ostomy appliance may refer to a level of a physical property of at least a part of the ostomy appliance, such as a level of moisture and/or temperature of at least a part of the ostomy appliance, such as a level of a physical property of at least a layer of the ostomy appliance, such as a level of moisture and/or temperature of at least a layer of the ostomy appliance, such as a level of a physical property of at least an adhesive layer of the ostomy appliance (e.g. a first adhesive layer proximal to the skin of the user). In one or more exemplary accessory devices, the interface is configured to obtaining the monitor data by obtaining the monitor data indicative of the condition comprising a moisture level of a first adhesive layer of the base plate and/or a moisture level of a proximal side of the first adhesive layer. The moisture level may be seen as representative of a conductive path in the first adhesive layer, such as across the first adhesive layer. The monitor data comprises e.g. data representative of the measurement of the electrical properties of the first adhesive layer. In other words, the condition may be seen as a condition of the first adhesive layer.

The method comprises obtaining (e.g. retrieving and/or receiving) monitor data from the monitor device.

The monitor data may comprise ostomy data and/or parameter data. The monitor device is configured to process the ostomy data and/or parameter data based on the ostomy data to determine monitor data that is transmitted to the accessory device. The ostomy data and/or parameter data may be indicative of resistance between electrodes of the base plate, capacitance and/or inductance between electrodes and/or any change thereof. For example, the ostomy data and/or parameter data may be indicative of a change in resistance, capacitance and/or inductance between electrodes. For example, the ostomy data and/or parameter data may comprise timing information, such as timestamped data or information from which timing is derivable.

The method comprises determining a current operating state of the ostomy appliance based on the monitor data, wherein the current operating state is indicative of a current adhesive performance of the ostomy appliance (e.g. of the base plate of the ostomy appliance).

An operating state in the present disclosure is indicative of the dynamic internal state of the ostomy appliance (e.g. of the base plate of the ostomy appliance currently being worn by the user) related to adhesive performance of the ostomy appliance. Adhesive performance of the ostomy appliance may be related to an internal condition of the ostomy appliance (e.g. of the base plate of the ostomy appliance), such as an internal condition of an adhesive layer of the ostomy appliance. The adhesive performance, and thereby the operating state may be affected by several factors, such as humidity, temperature, misplacement of the ostomy appliance on the stoma, and/or malfunction of the ostomy appliance. The adhesive performance, and thereby the operating state may be related to misplacement of the ostomy appliance on the stoma, and/or malfunction of the ostomy appliance. The one or more factors alone or in combination impact the adhesive performance of the ostomy appliance. Accordingly, the operating state may be varying in time.

Thus, there is a need for communicating not only the current operating state, but also the future operating state so as to plan and prevent any undesired situation caused by e.g. the ostomy appliance leaking, e.g. during a planned activity.

Adhesive performance may be indicative of wear property, e.g. wear time and/or wear comfort.

In one or more exemplary methods, an operating state is configured to indicate whether the ostomy appliance is properly operational based on its adhesive performance (e.g. wear property of the base plate, e.g. wear time and/or wear comfort).

For example, the operating state may be indicative of the severity and/or imminence of a leakage (e.g. low, medium, acute). The operating state may comprise Z operating states, where Z is an integer. The operating state may comprise a first operating state, a second operating state, a third operating state (e.g. good, check, change in X time/NOW).

The current operating state is indicative of a current adhesive performance of the ostomy appliance (e.g. of the base plate). The current operating state may be seen as the operating state at the latest reception time of monitor data. The current operating state may be seen as the operating state at the determination time at a time indicated in monitor data (e.g. at a latest time indicated in the monitor data, e.g. at a latest period of time up to the latest time).

Figure 19A:
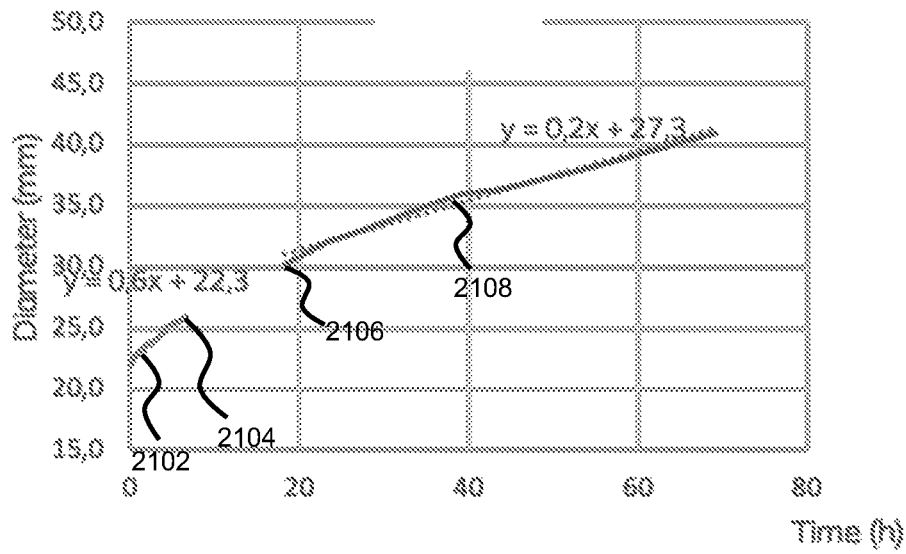
FIGS. 19A-19B are exemplary graphical representations of a whitening zone diameter as a function of time.
Figure 19B:
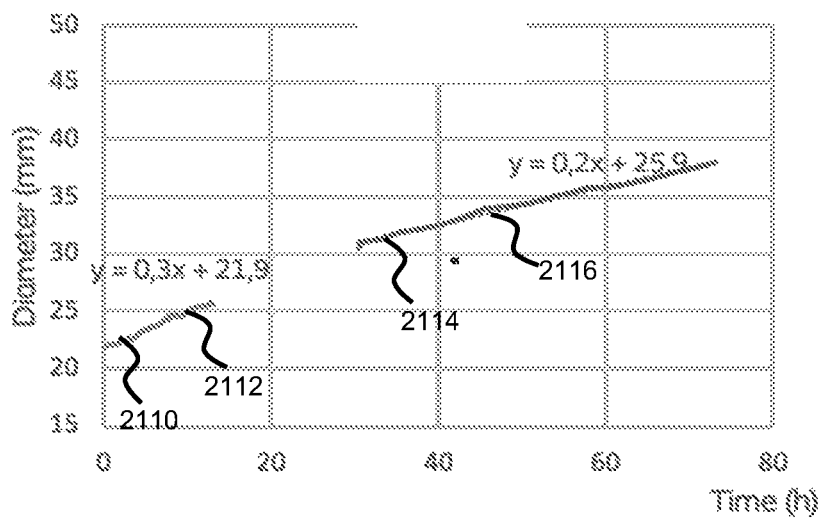

The method comprises determining a future operating state of the ostomy appliance (e.g. the future operating state of the base plate of the ostomy appliance) based on the monitor data and/or the current operating state. The future operating state is indicative of a future adhesive performance of the ostomy appliance (e.g. of the future adhesive performance of the base plate of the ostomy appliance). A future adhesive performance may be seen as a predictive adhesive performance, and/or an anticipated adhesive performance of the ostomy appliance in the future (e.g. the anticipated adhesive performance of the base plate of the ostomy appliance). The future operating state may be seen as an operating state that is anticipated to be reached after the current operating state. In other words, the future operating state may be seen as an operating state provided in advance of its occurrence (i.e. before it has happened). In one or more embodiments, the future operating state may be determined based on the current operating state by applying a applying a linear equation or a velocity factor as illustrated in FIGS. 19A-19B.

The future operating state may comprise at least one of: a wear time, a quality of adhesion, a moisture pattern representation. The current operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. A quality of adhesion may comprise a metric indicative of erosion of a layer of the base plate, such as of the first adhesive layer, a moisture pattern representation.

The method comprises displaying, on the display of the accessory device, a first user interface screen comprising a first primary user interface object representing the current operating state and/or a first secondary user interface object representing the future operating state. In one or more exemplary methods, the first user interface screen comprises a lock screen of the accessory device, and/or a home screen of the accessory device. In one or more exemplary methods, displaying the first user interface screen comprises displaying a first notification. The first notification may comprise the first primary user interface object representing the current operating state and/or the first secondary user interface object representing the future operating state.

The display of the first user interface screen comprising the first primary user interface object representing the current operating state and/or the first secondary user interface object representing the future operating state may be performed on the accessory device when the accessory device is a first operating mode (i.e. where the accessory device has an ostomy user application running) and/or a second operating mode (i.e. where the accessory device does not have an ostomy user application running).

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user, and created by the user. A user interface object may comprise a prompt.

The first primary user interface object representing the current operating state and/or the first secondary user interface object representing the future operating state may be part of a widget, such as a widget displayed in a widget user interface screen. The first primary user interface object representing the current operating state and the first secondary user interface object representing the future operating state may displayed in a reduced size in the widget.

A user interface screen refers herein to a graphical representation comprising a collection of user interface objects. A user interface screen comprises one or more user interface objects.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

It is an advantage of the present disclosure that a user of an ostomy appliance or a health care professional is able to control the current and future operating state of the ostomy appliance and thereby plan the use of the ostomy appliance in his/her daily life. The disclosed methods enable an accessory device to foresee and predict a potential risk of future leakage by determining one or more current and future operating states based on monitor data. Thus, communication of the one or more current and future operating states of the ostomy appliance helps reducing the risk of a user experiencing leakage (e.g. faecal material leakage coming out from the ostomy appliance) from an ostomy appliance in a planned activity.

A reduction of the risk of leakage in turn helps in reducing risks of skin damage to a user (as it supports the prevention of leakage due to e.g. adhesive erosion, malfunctions and misplacement of the ostomy appliance on the stoma).

In particular, determination and communication of future operating state(s), and possibly with the current operating state, according to the present disclosure, is performed based on monitor data indicative of a condition of the ostomy appliance which may not be visible to the user (because it is under or within the base plate of the ostomy appliance).

Further, it is seen that the present disclosure provides a clear distinction or differentiation between the following events in the present and the future: adhesive failure, leakage (incl. partial leakage) of faecal material which is harmful to the skin, and a sweating ostomate.

The present disclosure provides an efficient, and readily accessible user interface for monitoring and prediction of performance of an ostomy appliance with an improved degree of comfort for a user while allowing to derive future operating states based on monitor data that is not accessible or visible by the user or the health care professional. In other words, the disclosed method allows to anticipate and indicate the dynamic internal of the ostomy appliance to a user, which supports the user in coordinating the use of the ostomy appliance with the planning of daily life activities.

The method may comprise detecting a first input selecting any of the first primary user interface object and secondary user interface object, and in response to detecting the first input, opening an ostomy user application, (e.g. an ostomy user application installed on the accessory device). For example, detection of first input that corresponds to selection any of the first primary user interface object and secondary user interface object triggers the launch and opening of the ostomy user application installed on the accessory device.

The method may comprise: in response to opening the ostomy user application, displaying a second user interface screen comprising a second primary user interface object representing the current operating state of the ostomy appliance and a second secondary user interface object representing the future operating state. The second primary user interface object representing the current operating state of the ostomy appliance may be derived from the first primary user interface object (e.g. may have a graphical representation derived from the graphical representation of the first primary user interface object (e.g. increased or decreased in size, resolution; providing more precise information regarding the respective operating states)).

In one or more exemplary methods, the method comprises displaying one or more user interface objects requesting the user to indicate whether the displayed current operating state (especially if indicative of leakage) corresponds to the operating state perceivable by the user (e.g. a "yes, there is a leakage" user interface object, and "no, all good") so as to confirm the determination and display of the current operating state or so as to remedy an erroneous determination and display. The method may comprise detecting a user input (by selecting the user interface object or by receiving an utterance comprising: a "yes" or the word "leakage" or a "no" or the like) to determine whether the current operating state has been determined correctly.

In one or more exemplary methods, obtaining monitor data from a monitor device comprising obtaining the monitor data over a period time. The period of time may comprise K time periods, such as a first time period, a second time period, and/or a third time period. The memory may be configured to store the monitor data over a set of time periods comprising K time periods, wherein K is an integer. A time period may be expressed in terms of seconds, minutes, days, months, and/or years. A time period may relate to a time period of usage of the currently worn ostomy appliance (e.g. of the currently worn base plate). Additionally, or alternatively, the time period may relate to a time period of usage of similar ostomy appliances (e.g. base plates) previously worn by the user.

In one or more exemplary methods, determining the current operating state of the ostomy appliance (e.g. of the disclosed base plate) is based on the monitor data received over a period of time (e.g. over a set of time periods).

In one or more exemplary methods, determining the future operating state of the ostomy appliance (e.g. of the disclosed base plate) is based on the monitor data received over a period of time (e.g. over a set of time periods).

In one or more exemplary methods, determining the current operating state of the ostomy appliance is based on one or more previous operating states, such as based on one or more operating states previously determined by the accessory device (i.e. prior to the currently being determined operating state). The one or more operating states previously determined by the accessory device may relate the similar ostomy appliances as the one currently worn by the user. Optionally, one or more operating states previously determined by the accessory device may relate the different ostomy appliances as the one currently worn by the user, which have the same base plate as the one currently worn by the user.

In one or more exemplary methods, determining the future operating state of the ostomy appliance based on one or more previous operating states, such as based on one or more (future and/or current) operating states previously determined by the accessory device. A velocity factor may characterize a velocity of propagation of moisture through the first adhesive layer, as illustrated in FIGS. 19A-19B. Velocity data associated with the product type may be retrieved by the accessory device. The memory of the accessory device may have the velocity data stored thereon, or may be configured to store the velocity data to determine a future operating state based on a current operating state and/or the monitor data.

In one or more exemplary methods, the time period includes a period of time up to and including the current time. The time period may include a time period from a start time of use of the ostomy appliance, to the current time. The time period may include a time window that periodically occurs, such as a morning time period, an afternoon time period, a night time period, a daily time period, a weekly time period etc . . . .

Determining the current operating state of the ostomy appliance and the future operating state of the ostomy appliance may be performed based on monitor data obtained for similar product types of ostomy appliances previously worn by the user. A product type may be associated with a velocity of propagation of moisture through the first adhesive layer, as illustrated in FIGS. 19A-19B. The accessory device may be configured to retrieve (e.g. from a server device, and/or from a memory module of the accessory device, and/or from the monitor device) velocity data associated with the product type. The accessory device may have the velocity data stored thereon, or may be configured to store the velocity data to determine a future operating state based on a current operating state and/or the monitor data.

Determining a current operating state of the ostomy appliance and a future operating state of the ostomy appliance may be based on a parameter characterizing a product type of the ostomy appliance (e.g. for similar product types of ostomy appliances previously worn by the user).

Determining a current operating state of the ostomy appliance and a future operating state of the ostomy appliance may be based on a base plate parameter characterizing a product type of the base plate (and optionally for base plate parameters characterizing (similar) product types of base plates previously worn by the user), a bag parameter characterizing a bag of the ostomy appliance (and optionally for bag parameters characterizing similar bags of ostomy appliances previously worn by the user), a ring parameter characterizing a ring type of the ostomy appliance (and optionally for ring parameters characterizing similar ring types of ostomy appliances previously worn by the user), a user attribute, wherein the user attribute comprises a user age, a user gender, a user metabolism, a user health condition, a user current activity level. A user attribute may also comprise a region or country of residence. A user metabolism may be characterized by a user metabolism parameter indicative of the general metabolism of a user. A user health condition may be characterized by a user health condition parameter indicative of a health condition of a user: current health condition, average health condition, health condition profile over time. For example, the health condition parameter may comprise a first health condition, and a second health condition.

Figure 20A:
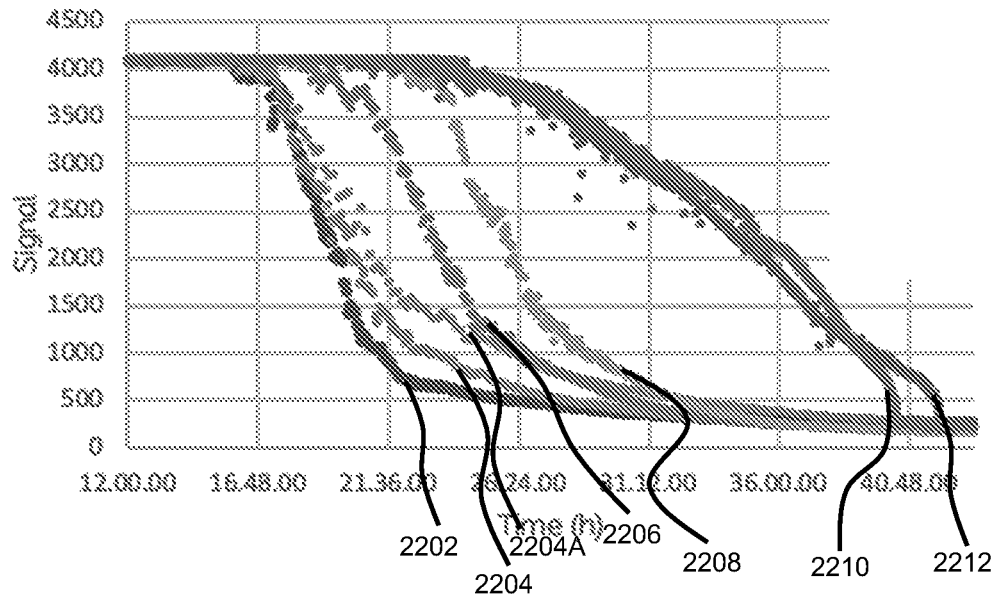
FIG. 20A is an exemplary graphical representation of first parameter data as a function of time for various semi-solid matter mixtures.
Figure 20B:
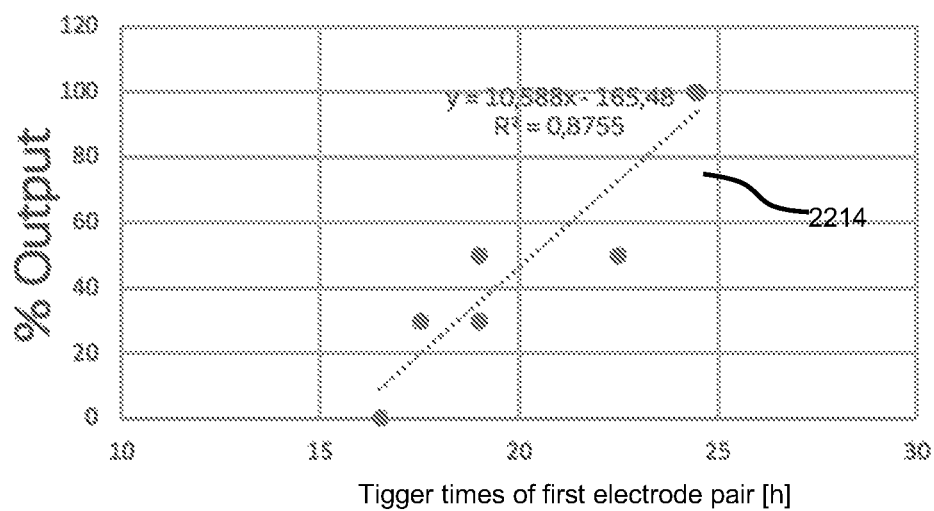
FIG. 20B is an exemplary graphical representation of first parameter data as a function of percentage of semi-solid matter in the mixture applied to the stomal opening.

A health condition I of a user may be indicative of the user being healthy, suffering from a permanent physical condition, suffering from a temporary physical condition. For example, if the health condition parameter indicates an inflammation, a future operating state may be determined to require an earlier change than if the health condition parameter indicates a healthy condition. For example, a user health condition may comprise an ostomy health condition such as ileostomy and/or colostomy. An ileostomist output may be more fluid than a colostomist output. A user health condition may be associated with a percentage of dilution of the output based on whether the user is an ileostomist or a colostomist. FIGS. 20A-20B illustrate dilution relation data between first parameter data and the dilution grade of an output mixture. The accessory device may be configured to retrieve dilution relation data associated with the user health condition. The accessory device may have the dilution relation data stored thereon, or may be configured to store the dilution relation data, so that the accessory device may determine a future operating state based on a current operating state and/or the monitor data using the dilution relation data.

A user activity level may be characterized by a user activity parameter indicative of an activity level of a user: current activity level, average activity level, activity level profile in time and/or in space. For example, the user activity parameter may comprise a first activity level, e.g. rest or sleep, and a second activity level, e.g. running or walking. An activity level of a user may be indicative of the user being stationary, sedentary, in motion, in exercising motion, in physical effort, resting or sleeping. A user activity parameter may comprise an activity level identifier and/or an activity level percentage. For example, if the user's activity level is high (e.g., when the user is running), a future operating state may be determined to require an earlier change than if the user is being less active. The reason being, inter alia, that the adhesion between the first adhesive layer and the skin surface of the user will likely degrade at a faster rate due to movement and, perhaps, increased perspiration when the user's activity level is high. Due to activity (e.g. sports, bending, movement), experimental results have shown that the operating state may be affected negatively by a reducing factor ranging from 2 to 10 compared to when the user has no or little activity (e.g. a sedentary user), For example, a wear time may be reduced by a factor of 2 to 10 due to an extensive activity. The disclosed accessory device is configured to select a factor ranging from 2 to 10 and to reduce (e.g. divide), by the selected factor, the current operating state when activity is detected, so as to determine the future operating state.

Determining a future operating state of the ostomy appliance may be based on a power capacity of a power unit of the monitor device.

Determining a future operating state of the ostomy appliance may be performed by applying a statistical analysis on the previous operating states, and/or on historic monitor data.

The method may comprise displaying, e.g. in the second user interface screen, third user interface objects representing previous operating states, the current operating state, and one or more future operating states mapped over a time window comprising elapsed time prior to the current time, current time and future time period after the current time. The second user interface screen may comprise a graph of a function or of a set that provides third user interface objects representing previous operating states, the current operating state and one or more future operating states over time, e.g. over a time window comprising elapsed time prior to the current time, current time and future time period after the current time.

The method may comprise displaying, on the display of the accessory device, the third user interface objects representing previous operating states, the current operating state, and one or more future operating states mapped over a time window comprising elapsed time prior to the current time, current time and future time period after the current time.

For example, the second user interface screen may comprise a graph of a function or of a set that provides third user interface objects representing the current remaining wear time and the one or more future remaining wear time vs. time, wherein a time axis comprises the current time, a past time period before the current time (e.g. a few hours or days) and a future time window after the current time (e.g. a few hours).

The method may comprise displaying, e.g. in the second user interface screen, a fifth user interface object indicative of the connection between the monitor device and the base plate. The fifth user interface object may indicate a connection state for the connection between the monitor device and the base plate (such as connected, not connected, searching, failed).

The method may comprise displaying, e.g. in the second user interface screen, a sixth user interface object indicative of battery status of the monitor device. The sixth user interface object may indicate a remaining battery time, and/or a remaining battery percentage (e.g. state of charge).

In one or more exemplary methods, the step of displaying is performed via the display of the accessory device.

The method may comprise displaying, on the display, a fourth user interface object. The method may comprise detecting a second input selecting the fourth user interface object. The method may comprise in response to detecting the second input, displaying a visual indicator indicating to the user to perform (e.g. and/or to initiate) a change of base plate. For example, in one or more exemplary methods, displaying the visual indicator indicating to the user to perform the change of base plate comprises displaying a first prompt indicating to the user to remove the monitor device from the used base plate.

In one or more exemplary methods, the visual indicator may comprise any one or more of the following prompts: one or more prompts to prepare products for change (e.g. cut base plate, scissors, bag, wipes, waste bag, removal spray, monitor device for change), one or more prompts to indicate that the products are ready, one or more prompts to remove the used base plate and/or used bag, one or more prompts to clean the peristomal area, one or more prompts to check the skin condition of the peristomal area, and one or more prompts to clean the used monitor device.

In one or more exemplary methods, the method comprises displaying one or more prompts (e.g. one or more user interface objects) requesting the user to indicate whether the task requested has been performed or the user is ready to move on the next task, and a user interface object to act upon (e.g. a "next" user interface object or a "yes" user interface object). The method may comprise detecting a user input (by selecting the user interface object to act upon or by receiving an utterance indicative of a "next" or a "yes") to confirm the performing of the task.

The method may comprise detecting, based on the monitor data, removal of the monitor device from the base plate; and updating accordingly the display of the fifth or sixth user interface object to indicate lack of connection between the monitor device and the base plate.

In one or more exemplary methods, displaying the visual indicator indicating to the user to perform the change of base plate comprises displaying a second prompt indicating to the user to apply a new base plate.

The method may comprise capturing an image of peristomal area of the user. The capturing may be performed in response to a capture prompt to capture the image, wherein the capture prompt instructs the user to capture an image of peristomal area.

In one or more exemplary methods, displaying the visual indicator indicating to the user to perform the change of base plate comprises displaying a third prompt indicating to the user to attach the monitor device to the new base plate.

The method may comprise detecting, based on the monitor data, attachment of the monitor device to the base plate, and updating accordingly the display of the fifth and/or sixth user interface object to indicate an established connection between the monitor device and the base plate.

The method may comprise determining whether the change of base plate satisfies a success criterion, and in accordance with the determination that the change of base plate satisfies the success criterion, displaying a seventh user interface object indicating that the ostomy system is operational.

In one or more exemplary methods, the success criterion comprises a primary success criterion, and when the primary success criterion is satisfied when the monitor device is connected properly to the base plate. The primary success criterion may require that the monitor device detects that a base plate is connected to the monitor device interface and communicates the state of connection accordingly. For example, the primary success criterion is satisfied when the monitor device has detected that a base plate is connected to the monitor device interface (in other words, when the monitor device interface indicates that a base plate is connected) and that the monitor devices communicates to the accessory device the corresponding state of connection to the base plate. The monitor device may further be configured to identify the base plate by a base plate identifier obtained via the monitor device interface, and therefore may be configured to communicate to the accessory device that state of connection and that the connected base plate is different (e.g. a new base plate) from the used base plate.

In one or more exemplary methods, the success criterion comprises a secondary success criterion, and wherein when the secondary success criterion is satisfied when the monitor device is connected properly to accessory device. The secondary success criterion may require that the accessory device detects a (successful) connection to the monitor device (e.g. a short-range (e.g. Bluetooth) connection, a WiFi connection, a cellular connection). For example, the primary success criterion is satisfied when the accessory device (or interface thereof) has detected the connection to the monitor device. The accessory device may further be configured to identify the monitor device by a monitor device identifier obtained via the monitor device interface, and therefore may be configured to determine whether the connected monitor device is different (e.g. a new monitor device) from the used monitor device.

The method may comprise storing one or more events related to any one or more of the prompts.

The method may comprise storing one or more current operating states.

The method may comprise storing one or more current future states.

In one or more exemplary methods, the success criterion is satisfied when the primary success criterion is satisfied, and when the secondary criterion is satisfied.

In one or more exemplary methods, the success criterion is satisfied when the primary success criterion is satisfied.

In one or more exemplary methods, displaying a seventh user interface object indicating that the ostomy system is operational comprises displaying the seventh user interface object indicative of the current operating state being operational on a home screen, and/or on a lock screen.

In one or more exemplary methods, displaying a seventh user interface object indicating that the ostomy system is operational comprises displaying the seventh user interface object in a third user interface screen of the ostomy user application.

The method may comprise obtaining an operating state of the ostomy appliance; determining whether the operating state satisfies a change criterion; and in accordance with the operating state satisfying a change criterion, performing the displaying of the first user interface screen comprising the first primary user interface object and the first secondary user interface object. The change criterion may be met when it is determined that the current operating state is indicative of a remaining wear time that is at or below a wear threshold (e.g. a time sufficient for operating a change of ostomy appliance).

The method may comprise determining a status of an ostomy inventory of the user, and displaying on a fourth user interface screen one or more user interface objects representative of the status. The status of the ostomy inventory may comprise inventory status related to one or more bags, inventory status related to one or more base plates, inventory status related to one or more rings.

The disclosure provides an accessory device, wherein the accessory device forms part of an ostomy system (e.g. the ostomy system disclosed herein). The accessory device comprises a memory; a processor; and an interface configured to communicate with one or more devices of the ostomy system. The one or more devices of the ostomy system comprise a monitor device, and/or an ostomy appliance configured to be placed on a skin surface of a user. The ostomy appliance comprises a base plate.

The interface is coupled to the processor and the memory. The interface comprises a display. The interface is configured to obtain monitor data from the monitor device. The processor is configured to determine a current operating state of the ostomy appliance based on the monitor data; to determine a future operating state of the ostomy appliance based on the monitor data and the current operating state; and to provide data for display, on the display, a first user interface screen comprising a first primary user interface object representing the current operating state and/or a first secondary user interface object representing the future operating state.

For example, the processor may be configured to determine the current operating state of the ostomy appliance based on the monitor data by determining one or more current moisture pattern types based on the monitor data, such as based on the ostomy data and/or the parameter data (e.g. first parameter data and second parameter data), such as based on measurements obtained by the electrodes, such as measurements of resistance, capacitance and/or inductance, such as timing information.

The processor may be configured to determine the future operating state based on the current operating state, and optionally any operating state prior to the determining of the future operating state.

In one or more exemplary methods and accessory devices, the first parameter data, the second parameter data, and the third parameter data may be indicative of resistance between the first electrode pair, the second electrode pair, and the third electrode pair, respectively. The first parameter data, the second parameter data, and the third parameter data may be indicative of voltage between the first electrode pair, the second electrode pair, and the third electrode pair, respectively (and thus indicative of resistance). The first parameter data, the second parameter data, and the third parameter data may be indicative of current between the first electrode pair, the second electrode pair, and the third electrode pair, respectively (and thus indicative of resistance).

The first parameter data, the second parameter data, and the third parameter data may be indicative of a rate of change in resistance between the first electrode pair, the second electrode pair, and the third electrode pair, respectively. In one or more exemplary monitor devices, the first parameter data, the second parameter data, and the third parameter data may be indicative of a rate of change in voltage between the first electrode pair, the second electrode pair, and the third electrode pair, respectively. In one or more exemplary monitor devices, the first parameter data, the second parameter data, and the third parameter data may be indicative of a rate of change in current between the first electrode pair, the second electrode pair, and the third electrode pair, respectively.

To determine a current and/or future operating state of the base plate of the ostomy appliance may comprise to determine an operating state (e.g. current and/or future operating state) from a set of operating states. In other words, to determine a current and/or future operating state may comprise selecting an operating state from a set of predefined operating states. The set of predefined operating states may comprise a number of operating states, such as at least two operating states, at least three operating states, at least four operating states, at least five operating states. The number of operating states may be in the range from four to twenty. In one or more exemplary accessory devices, the number of operating states in the set of predefined operating states is larger than ten, such as larger than 20 or even larger than 50.

In one or more exemplary methods and accessory devices, to determine an operating state of the base plate is performed if a determination trigger criterion is fulfilled. The determination trigger criterion may be based on the first parameter data, the second parameter data and/or the third parameter data. The determination trigger criterion may be fulfilled if parameter data changes, e.g. if a change in parameter data is larger than a change threshold.

In one or more exemplary methods and accessory devices, to determine a current and/or future operating state of the base plate is based on a first criteria set based on the first parameter data and/or the second parameter data, wherein the current and/or future operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary methods and accessory devices, to determine a current and/or future operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by or may at least comprise:

($P\_1\_1 < TH\_1\_1$),
($P\_2\_1 > TH\_1\_2$), and
($P\_3\_1 > TH\_1\_3$), wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion or radial swelling on the base plate. The first threshold values ($TH\_1\_1$, $TH\_1\_2$ and $TH\_1\_3$) may be the same or different, e.g. depending on the electrode configuration of the base plate. The first tertiary criterion ($P\_3\_1 < TH\_1\_3$) may be omitted in the first criteria set. The first operating state, e.g. indicative of low degree of radial erosion on the base plate may be indicative of a radial progression of moisture to the first electrode pair (but not to the second electrode pair and not to the third electrode pair) which corresponds to e.g. an un-alarming and/or normal radial progression of moisture.

In one or more exemplary embodiments, when the first parameter data, the second parameter data and the third parameter data are each respectively indicative of resistance between the first electrode pair, the second electrode pair and the third electrode pair respectively, the first threshold values ($TH\_1\_1$, $TH\_1\_2$ and $TH\_1\_3$) may correspond to first resistance threshold values. In one or more exemplary embodiments, the first primary threshold value $TH\_1\_1$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the first secondary threshold value TH_1_2 may correspond to the upper resistance threshold value. In one or more exemplary embodiments, the first tertiary threshold value TH_1_3 may correspond to the upper resistance threshold value. The first primary parameter P_1_1 may be indicative of the resistance between the first electrode pair (first electrode and first electrode part of the ground electrode) of the base plate. The first parameter data may comprise a first secondary parameter which may be derived from the first primary parameter, and/or a first tertiary parameter, which may be derived from the first primary parameter. A first secondary parameter P_1_2 may comprise or be a gradient derived from the first primary parameter. In one or more embodiments, a first primary parameter P_1_1 may be indicative of a voltage between the first electrode pair (first electrode and first electrode part of the ground electrode) of the base plate.

In one or more exemplary embodiments, when the first parameter data, the second parameter data and the third parameter data are each respectively indicative of voltage between the first electrode pair, the second electrode pair and the third electrode pair respectively, the first threshold values (TH_1_1, TH_1_2 and TH_1_3) may correspond to first voltage threshold values. In one or more exemplary embodiments, the first primary threshold value TH_1_1 may correspond to an upper voltage threshold value. An upper voltage threshold value may be set to a value less than 5 Volts, such as 3 Volts, such as 2, 86 Volts. In one or more exemplary embodiments, the first secondary threshold value TH_1_2 may correspond to the upper voltage threshold value. In one or more exemplary embodiments, the first tertiary threshold value TH_1_3 may correspond to the upper voltage threshold value.

The first criteria set may comprise e.g.
(P_4_1>TH_1_4)
wherein P_4_1 is a fourth primary parameter based on the fourth parameter data and indicative of the resistance, voltage, or current between the fourth electrode pair and TH_1_4 is a first quaternary threshold value, and wherein the first operating state is indicative of absence of fluid on the proximal side of the first adhesive layer of the base plate of the ostomy appliance. In one or more exemplary embodiments, the first quaternary threshold value TH_1_4 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the following additional criterion may be determined
(P_1_1<TH_low),
wherein P_1_1 is a first primary parameter based on the first parameter data, TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the first electrode pair by the moisture detected and there are no further changes expected by the first primary parameter. Moisture is likely to continue its progression.

In one or more exemplary embodiments, the following additional criterion may be determined
(P_2_1<TH_low),
wherein P_2_1 is a second primary parameter based on the second parameter data, TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the second electrode pair by the moisture detected and there are no further changes expected by the second primary parameter. Moisture is likely to continue its progression.

In one or more exemplary embodiments, the following additional criterion may be determined:
(P_3_1>TH_low),
P_3_1 is a third primary parameter based on the third parameter data, and TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the third electrode pair by the moisture detected and there are no further changes expected by the second primary parameter. Moisture is likely to continue its progression.

In one or more exemplary embodiments, one or more criteria of a criteria set, e.g. one or more first criteria of the first criteria set and/or one or more second criteria of the second criteria set, may be based on timing information or one or more delay parameters based on the parameter data. In one or more exemplary embodiments, one or more delay parameters or time differences related to different parameter data, e.g. related to the first parameter data and the second parameter data, are determined.

In one or more exemplary embodiments, one or more first criteria of the first criteria set may be based on timing information (e.g. one or more delay parameters of the parameter data and/or one or more times where a parameter crosses a threshold).

In one or more exemplary embodiments, the timing information may comprise a time difference D_1_2_1 between a time T1 where P_1_1 crosses a threshold, such as TH_1_1, and a time T2 where P_2_1 crosses a threshold, such as TH_1_2. Thus, delay parameter or time difference D_1_2_1 may be given as D_1_2_1=T2−T1.

In one or more exemplary embodiments, the timing information, e.g. used in the first criteria set, may comprise a time difference D_2_3_1 between a time T2 where P_2_1 crosses a threshold, such as TH_1_2, and a time T3 where P_3_1 crosses a threshold, such as TH_1_3. Thus, delay parameter or time difference D_2_3_1 may be given as D_2_3_1=T3−T2.

In one or more exemplary embodiments, one or more criteria sets, such as the third criteria set and/or the second criteria set, may comprise any of:
D_1_2_1>Z
D_2_3_1>Z
Wherein Z is a time difference constant characterizing the progression of moisture (e.g. 3 h, e.g. 2 h). Different time difference constants may be employed in different criteria sets/for different time delays.

In one or more exemplary embodiments, one or more criteria sets, such as the second criteria set and/or the third criteria set may comprise any of:
D_1_2_1>Z
Wherein Z is a time difference constant characterizing the progression of moisture (e.g. 3 h, e.g. 2 h).

The second primary parameter may be indicative of the resistance between the second electrode pair (second electrode and second electrode part of the ground electrode) of the base plate. The second parameter data may comprise a second secondary parameter, and/or a second tertiary parameter, which may be derived from the second primary parameter. A second secondary parameter may be indicative of a voltage between the second electrode pair (second electrode and second electrode part of the ground electrode) of the base plate.

The third primary parameter may be indicative of resistance between the third electrode pair (third electrode and third electrode part of the ground electrode) of the base plate. The third parameter data may comprise a third secondary parameter, and/or a third tertiary parameter, which may be derived from the third primary parameter. A third secondary parameter may be indicative of a voltage between the second electrode pair (second electrode and second electrode part of the ground electrode) of the base plate.

In one or more exemplary methods and accessory devices, to determine a current and/or future operating state of the base plate is based on a second criteria set based on the second parameter data and/or the third parameter data, wherein the current and/or future operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary methods and accessory devices, to determine a current and/or future operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by or at least may comprise:

(P_1_1<TH_2_1),
(P_2_1<TH_2_2), and
(P_3_1>TH_2_3)

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion or radial swelling on the base plate. The second threshold values (TH_2_1, TH_2_2 and TH_2_3) may be the same or different, e.g. depending on the electrode configuration of the base plate. The second primary criterion (P_1_1<TH_2_1) and/or the second tertiary criterion (P_3_1>TH_2_3) may be omitted in the second criteria set. The second operating state indicative of medium degree of radial erosion on the base plate may be indicative of a radial progression of moisture to the first electrode pair and the second electrode pair (and not the third electrode pair). The second operating state indicative of medium degree of radial erosion on the base plate may be indicative of a radial progression of moisture to the first electrode pair and to the second electrode pair.

In one or more exemplary embodiments, when the first parameter data, the second parameter data and the third parameter data are each respectively indicative of resistance between the first electrode pair, the second electrode pair and the third electrode pair respectively, the second threshold values (TH_2_1, TH_2_2 and TH_2_3) may correspond to second resistance threshold values. In one or more exemplary embodiments, the second primary threshold value TH_2_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the second secondary threshold value TH_2_2 may correspond to the upper resistance threshold. In one or more exemplary embodiments, the second tertiary threshold value TH_2_3 may correspond to the upper resistance threshold value. In one or more exemplary embodiments, the second primary threshold value TH_2_1 may correspond to a medium resistance threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, when the first parameter data, the second parameter data and the third parameter data are each respectively indicative of voltage between the first electrode pair, the second electrode pair and the third electrode pair respectively, the second threshold values (TH_2_1, TH_2_2 and TH_2_3) may correspond to second voltage threshold values. In one or more exemplary embodiments, the second primary threshold value TH_2_1 may correspond to an upper voltage threshold value. An upper voltage threshold value may be set to a value less than 5 Volts, such as 3 Volts, such as 2.86 Volts. In one or more exemplary embodiments, the second secondary threshold value TH_2_2 may correspond to the upper voltage threshold value. In one or more exemplary embodiments, the second tertiary threshold value TH_2_3 may correspond to the upper voltage threshold value. In one or more exemplary embodiments, the second primary threshold value TH_2_1 may correspond to a medium voltage threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, the second criteria set may comprise any of:

D_1_2_1>Z

Wherein Z is a time difference constant characterizing the progression of moisture (e.g. 3 h, e.g. 2 h).

In one or more exemplary methods and accessory devices, to determine a current and/or future operating state of the base plate is based on a default criteria set based on the first parameter data, wherein the current and/or future operating state is determined to be the default operating state if the default criteria set is satisfied, and in accordance with a determination that the current and/or future operating state is the default operating state, transmit a default monitor signal comprising monitor data indicative of the default operating state of the ostomy appliance.

The default criteria set may be given by or at least may comprise:

(P_1_1>TH_D_1),
(P_2_1>TH_D_2), and
(P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion or radial swelling on the base plate. The default threshold values (TH_D_1, TH_D_2 and TH_D_3) may be the same or different, e.g. depending on the electrode configuration of the base plate. In one or more exemplary embodiments, when the first parameter data, the second parameter data and the third parameter data are each respectively indicative of resistance between the first electrode pair, the second electrode pair and the third electrode pair respectively, the default threshold values (TH_D_1, TH_D_2 and TH_D_3) may correspond to default resistance threshold values. In one or more exemplary embodiments, the second primary threshold value TH_D_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the default secondary threshold value TH_D_2 may correspond to the upper resistance threshold. In one or more exemplary embodiments, the default tertiary threshold value TH_D_3 may correspond to the upper resistance threshold value.

In one or more exemplary embodiments, when the first parameter data, the second parameter data and the third parameter data are each respectively indicative of voltage between the first electrode pair, the second electrode pair and the third electrode pair respectively, the default threshold values (TH_D_1, TH_D_2 and TH_D_3) may correspond to default voltage threshold values. In one or more exemplary embodiments, the default primary threshold value TH_D_1 may correspond to an upper voltage threshold value. An upper voltage threshold value may be set to a value less than 5 Volts, such as 3 Volts, such as 2.86 Volts. In one or more exemplary embodiments, the default secondary threshold value TH_D_2 may correspond to the upper voltage threshold value. In one or more exemplary embodiments, the default tertiary threshold value TH_D_3 may correspond to the upper voltage threshold value.

In one or more exemplary methods and accessory devices, to determine a current and/or future operating state of the base plate is based on a third criteria set based on the third parameter data, wherein the current and/or future operating state is determined to be the third operating state if the third criteria set is satisfied, and in accordance with a determination that the current and/or future operating state is the third operating state, transmit a third monitor signal comprising monitor data indicative of the third operating state of the ostomy appliance.

In one or more exemplary methods and accessory devices, the third operating state of the base plate corresponds to a situation wherein the first adhesive layer of the base plate has experienced a third degree of radial erosion or radial swelling, e.g. the first adhesive layer is eroded to the third radial distance of the third electrode pair.

The third criteria set may be given by or at least may comprise:
(P_1_1<TH_3_1),
(P_2_1<TH_3_2), and
(P_3_1<TH_3_3)

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion or radial swelling on the base plate. The third threshold values (TH_3_1, TH_3_2 and TH_3_3) may be the same or different, e.g. depending on the electrode configuration of the base plate. The third primary criterion (P_1_1<TH_3_1) and/or the third secondary criterion (P_2_1<TH_3_2) may be omitted in the third criteria set. The third operating state indicative of high degree of radial erosion on the base plate may be indicative of high likelihood of leakage, e.g. on the proximal side of the base plate, e.g. within a time period e.g. within the next 20 minutes. The third operating state may indicate a radial progression of moisture to the first electrode pair, the second electrode pair, and the third electrode pair.

In one or more exemplary embodiments, when the first parameter data, the second parameter data and the third parameter data are each respectively indicative of resistance between the first electrode pair, the second electrode pair and the third electrode pair respectively, the third threshold values (TH_3_1, TH_3_2 and TH_3_3) may correspond to third resistance threshold values. In one or more exemplary embodiments, the third primary threshold value TH_3_1 may correspond to an upper resistance threshold value. In one or more exemplary embodiments, the third secondary threshold value TH_3_2 may correspond to an upper resistance threshold value. In one or more exemplary embodiments, the third tertiary threshold value TH_3_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the third primary threshold value TH_3_1 may correspond to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. In one or more exemplary embodiments, the third secondary threshold value TH_3_2 may correspond to a medium resistance threshold. A medium resistance threshold value may be set to a value less than 10 Mega-Ohms, such as 5 Mega-Ohms, such as 3 Mega-Ohms, such as 2 Mega-Ohms, such as 1 Mega-Ohms. In one or more exemplary embodiments, the third tertiary threshold value TH_3_3 may correspond to the upper resistance threshold. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, when the first parameter data, the second parameter data and the third parameter data are each respectively indicative of voltage between the first electrode pair, the second electrode pair and the third electrode pair respectively, the third threshold values (TH_3_1, TH_3_2 and TH_3_3) may correspond to third voltage threshold values. In one or more exemplary embodiments, the third primary threshold value TH_3_1 may correspond to an upper voltage threshold value. In one or more exemplary embodiments, the third secondary threshold value TH_3_2 may correspond to an upper voltage threshold value. In one or more exemplary embodiments, the second tertiary threshold value TH_2_3 may correspond to the upper voltage threshold value.

In one or more exemplary embodiments, the third primary threshold value TH_3_1 may correspond to a lower voltage threshold value. In one or more exemplary embodiments, a lower voltage threshold value may be set to a value which is less than 1 Volt, such as 0.5 Volt, such as 0.25 Volts, such as 0.22 Volts. In one or more exemplary embodiments, the third secondary threshold value TH_3_2 may correspond to a medium voltage threshold value. A medium voltage threshold value may be set to a value less than 2 Volts, such as 1.5 Volts. In one or more exemplary embodiments, the second tertiary threshold value TH_2_3 may correspond to the upper voltage threshold value.

In one or more exemplary embodiments, the third criteria set may comprise any of:
D_1_2_1<Z
D_2_3_1<Z Wherein Z is a time difference constant characterizing the progression of moisture (e.g. 3 h, e.g. 2 h), a time difference D_1_2_1 between a time T1 where P_1_1 crosses TH_1_1 and a time T2 where P_2_1 crosses TH_1_2, and a time difference D_2_3_1 between a time T2 where P_2_1 crosses TH_1_2 and a time T3 where P_3_1 crosses TH_1_3.

In one or more exemplary monitor devices, the ostomy data comprises fourth ostomy data from a fourth electrode pair of the base plate. To apply a processing scheme may comprise to obtain fourth parameter data based on the fourth ostomy data, and determine an operating state of the base plate of the ostomy appliance based on the fourth parameter data. The accessory device may be configured to, in accordance with a determination that the operating state is a fourth operating state, transmit a fourth monitor signal comprising monitor data indicative of the fourth operating state of the ostomy appliance.

In one or more exemplary embodiments, the fourth operating state of the base plate corresponds to a situation, wherein the fourth electrode pair detects fluid, such as output, between the proximal surface of first adhesive layer and the skin of the user at a fourth radial distance, and thus there is a high risk of leakage from the ostomy appliance in the fourth operating state.

The fourth criteria set may be given by or at least may comprise:
(P_4_1<TH_4_4)

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance. In one or more exemplary embodiments, the fourth quaternary threshold value TH_4_4 may correspond to an upper resistance threshold value.

In one or more exemplary embodiments, a fifth operating state of the base plate corresponds to a situation, wherein the fourth electrode pair detects fluid, such as sweat, between the proximal surface of first adhesive layer and the skin of the user at a fourth radial distance, and thus there is a no leakage from the ostomy appliance in the fifth operating state.

The fifth operating state may be determined in accordance with a determination that one or more fifth criterion of a fifth criteria set are satisfied.

The fifth criteria set may be given by or at least may comprise:
(P_4_1<TH_5_1)
(P_4_2<TH_5_2)
(P_4_3<TH_5_3)
(∇P_4_1<V)
(∇P_4_2<V) and
(∇P_4_3<V)

Wherein P_4_1 is a fourth primary parameter based on the fourth parameter data and indicative of the resistance between the fourth electrode pair, P_4_2 is a fourth secondary parameter indicative of the resistance between the fourth electrode and the fifth electrode, P_4_3 is a fourth tertiary parameter based on the fourth parameter data and indicative of the resistance between the fifth electrode pair and TH_5_1 is a fifth primary threshold value, TH_5_2 is a fifth secondary threshold value, TH_5_3 is a fifth tertiary threshold value and ∇P_4_1 is gradient of P_4_1, ∇P_4_2 is gradient of P_4_2, ∇P_4_3 is gradient of P_4_3, and V is a gradient limit (e.g. 80%). In one or more exemplary embodiments, the fifth primary threshold value TH_5_1 may correspond to an upper resistance threshold value. In one or more exemplary embodiments, TH_5_2 may correspond to an upper resistance threshold value. In one or more exemplary embodiments, TH_5_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The fifth operating state may refer to presence of sweat detected by the fourth parameter data indicating moisture detected omnidirectionally from the stomal opening and uniformly.

In one or more exemplary monitor devices, the sixth operating state of the base plate corresponds to a situation, wherein the fourth electrode pair detects fluid, such as output, between the proximal surface of first adhesive layer and the skin of the user at a fourth radial distance, and thus there is a sudden leakage from the ostomy appliance in the sixth operating state.

A sixth operating state may be determined in accordance with a determination that one or more sixth criteria of a sixth criteria set are satisfied by the fourth parameter data.

The sixth criteria set may comprise a sixth primary criterion, wherein the sixth primary criterion may comprise:
(P_4_1<TH_6_1) and
(∇P_4_1>V)

The sixth criteria set may comprise a sixth secondary criterion, wherein the sixth secondary criterion may comprise:
(P_4_2<TH_6_2) and
(∇P_4_2>V)

The sixth criteria set may comprise a sixth tertiary criterion, wherein the sixth tertiary criterion may comprise:
(P_4_3<TH_6_3) and
(∇P_4_3>V)

Wherein P_4_1 is a fourth primary parameter based on the fourth parameter data and indicative of the resistance between the fourth electrode pair, P_4_2 is a fourth secondary parameter indicative of the resistance between the fourth electrode and the fifth electrode, P_4_3 is a fourth tertiary parameter indicative of the resistance between the fifth electrode pair (fifth electrode and ground electrode) and TH_6_1 is a sixth primary threshold value, TH_6_2 is a sixth secondary threshold value TH_6_3 is a sixth tertiary threshold value, and ∇P_4_1 is gradient of P_4_1, ∇P_4_2 is gradient of P_4_2, ∇P_4_3 is gradient of P_4_3, and V is a gradient limit (e.g. 80%). In one or more exemplary embodiments, the sixth primary threshold value TH_6_1 may correspond to an upper resistance threshold value. In one or more exemplary embodiments, TH_6_2 may correspond to an upper resistance threshold value. In one or more exemplary embodiments, TH_6_3 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The sixth operating state may refer to presence of output detected by the fourth parameter data indicating a sudden leak, e.g. a developing leak. In one or more exemplary embodiments, when the time T is below X minutes from the placement of the base plate, where X is between 5 to 60 minutes, and when any of P_1_1, P_2_1, P_3_1 in average over T are below a default threshold value corresponding to an upper resistance threshold value, this indicates that any of the first electrode pair, the second electrode pair, and the third electrode pair is cut (e.g. cut by the user when preparing the base plate for placement around the stoma). In one or more exemplary embodiments, when the time T is below X minutes from the placement of the base plate, where X is between 5 to 60 minutes, and when any of P_4_1, P_4_2, P_4_3 in average over T are below a default threshold value corresponding to an upper resistance threshold value, this indicates an instant leakage, e.g. presence of output on the proximal side.

In one or more exemplary embodiments, any of the first criteria set, the second criteria set, the third criteria set, the fourth criteria set, the default criteria set, the fifth criteria set, the sixth criteria set may be used to define one or more further criteria sets, and thereby to determine one or more operating states.

In one or more exemplary embodiments, different criteria sets may be used to determine the same operating state.

For example, the processor may be configured to determine the future operating state of the ostomy appliance based on the monitor data by determining one or more future moisture pattern types based on the monitor data, such as based on the ostomy data and/or the parameter data (e.g. first parameter data and second parameter data), such as based on measurements obtained by the electrodes, such as measurements of resistance, capacitance and/or inductance, such as timing information. The moisture pattern type is optionally indicative of adhesive condition (e.g. failure) of the base plate and/or leakage risk of the ostomy appliance and/or indicative of the risk of skin damage to the user of the ostomy system.

For example, the processor may be configured to determine the future operating state of the ostomy appliance determining one or more future moisture pattern types based on the first parameter data and second parameter data (and optionally a third parameter). For example, to determine one or more future moisture pattern types may comprise to select a moisture pattern type from a set of predefined moisture pattern types based on a trend identified in the monitor data over a period of time. The set of predefined moisture pattern types may comprise a number M of moisture pattern types, such as at least three moisture pattern types, at least four moisture pattern types, at least five moisture pattern types. The number M of moisture pattern types may be in the range from four to twenty. For example, to determine one or more future moisture pattern types may comprise to compare the first parameter data and/or the second parameter data, to determine whether the first parameter data and/or the second parameter data satisfy one or more criteria, and to identify a future moisture pattern type based on the determination.

In one or more accessory devices, to determine the current operating state of the ostomy appliance and/or the future operating state based on the monitor data comprises to derive the current operating state of the ostomy appliance and/or the future operating state based on the one or more moisture pattern types, such as a first moisture pattern type, a second moisture pattern type, and/or a third moisture pattern type.

It may be envisaged that the processor may be configured to determine the future operating state of the ostomy appliance by deriving a trend or a function of an operating state and/or the monitor data over the time period, e.g. for the similar ostomy appliances as the one currently worn by the user, or for similar base plates as the currently worn one.

The present disclosure relates to an ostomy system comprises an ostomy appliance with a base plate disclosed herein, a monitor device disclosed herein, and an accessory device disclosed herein configured to perform any of the methods disclosed herein.

The present disclosure relates to a computer readable storage medium storing one or more programs, the one or more programs comprising instructions, which when executed by an accessory device with an interface, a memory and a processor causing the accessory device to perform any of the methods disclosed herein.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device.

Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
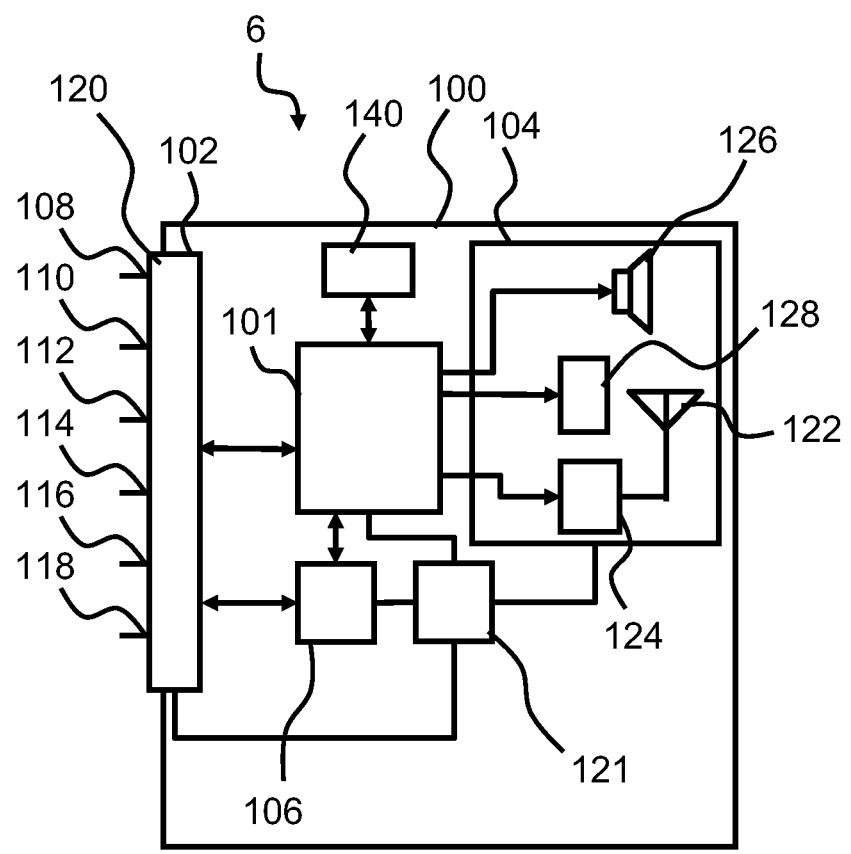
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

Figure 3:
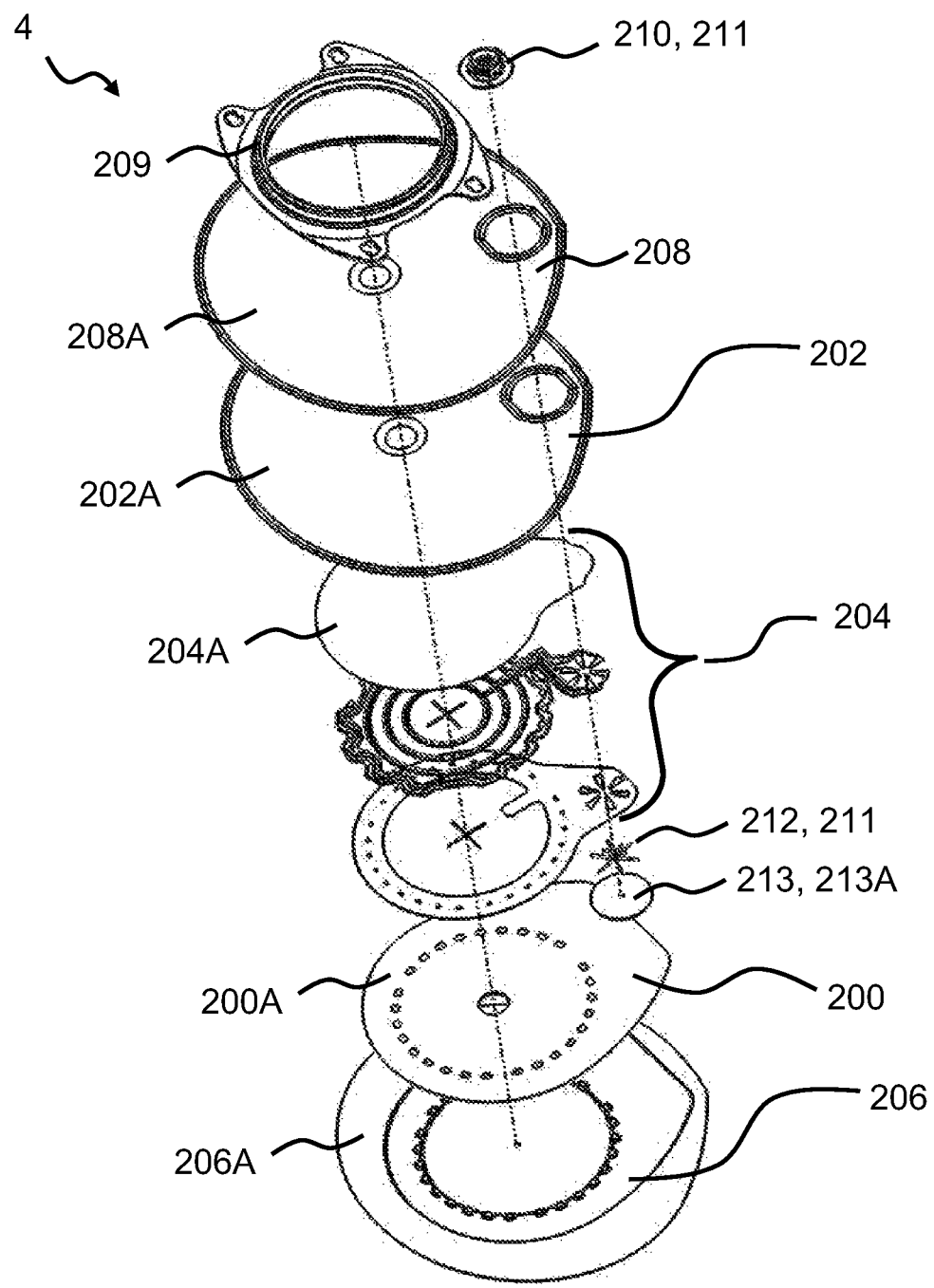
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
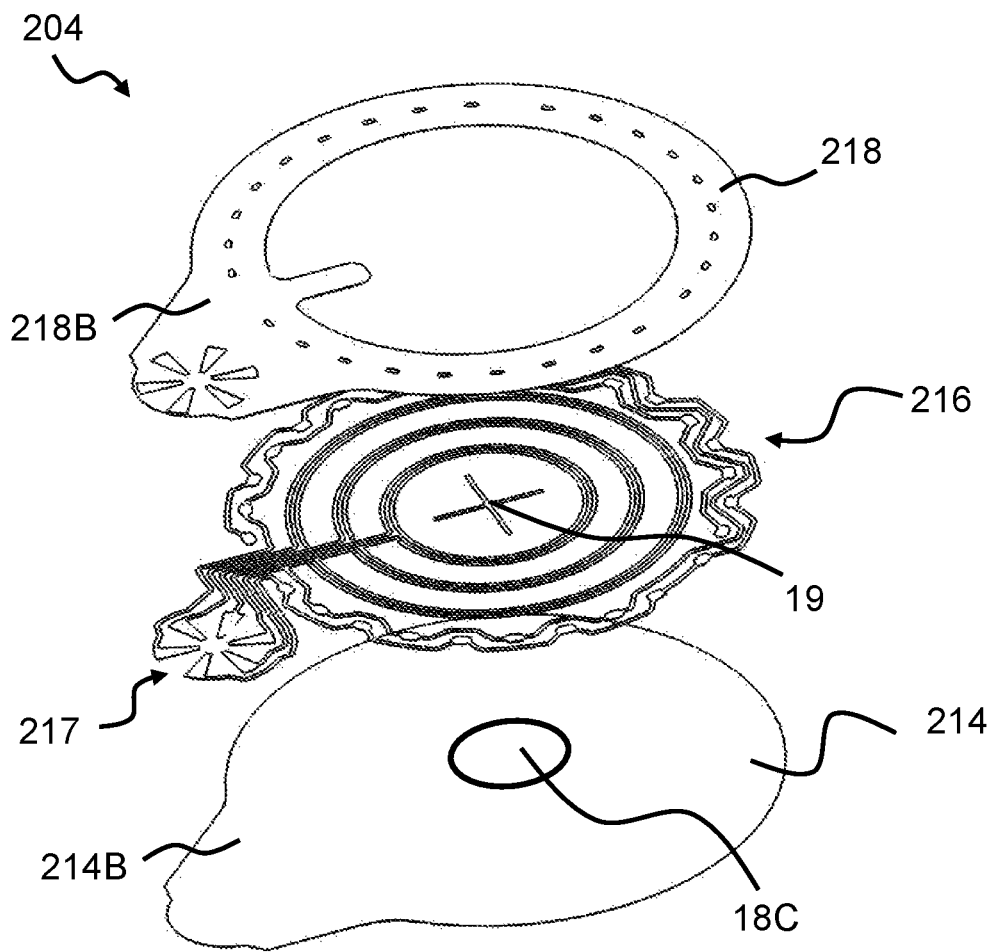
FIG. 4 is an exploded view of an exemplary electrode assembly.

FIG. 4 illustrates an exploded view of an exemplary electrode assembly 204 of a base plate. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
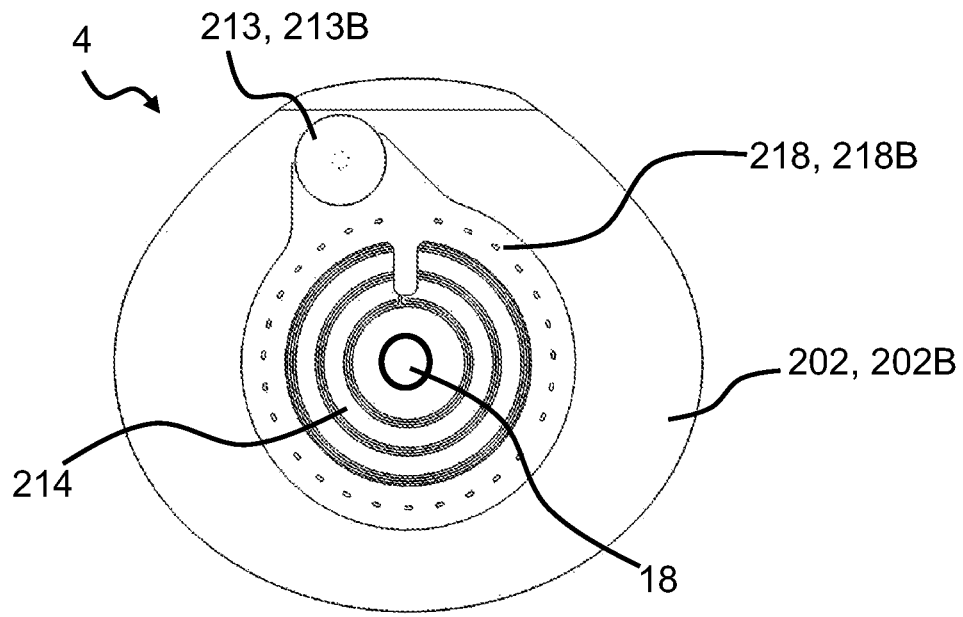
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
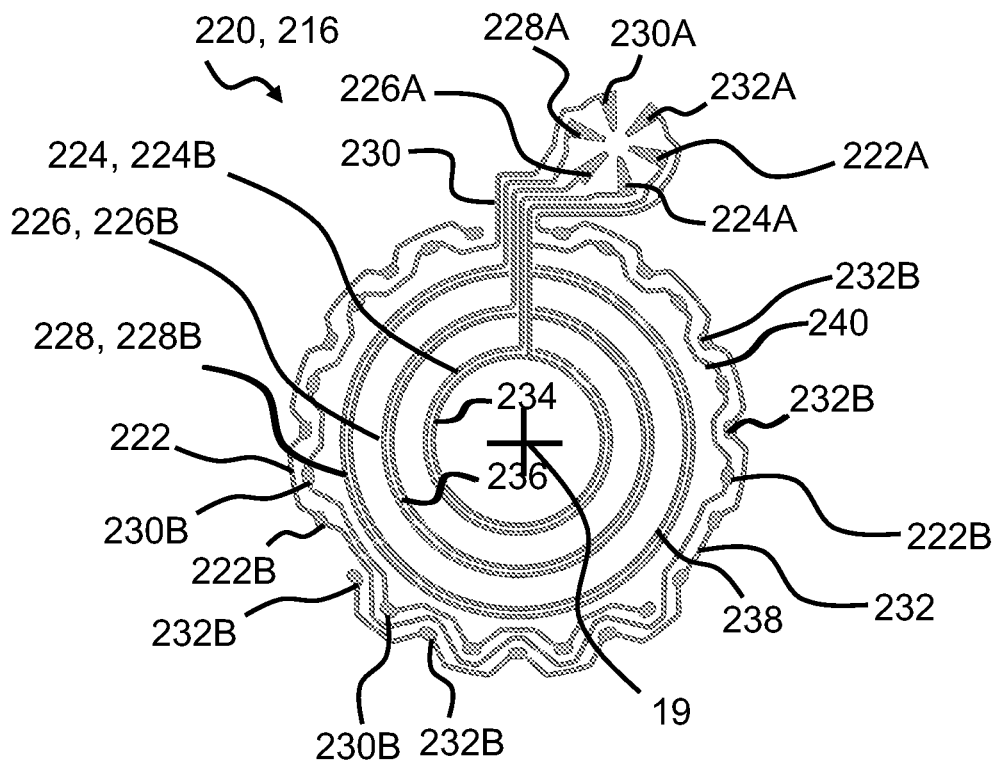
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 224 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

The first sensing part 224B extends circularly at least 330 degrees around the stomal opening at a first radial distance R1 from the center point 19. The first radial distance R1 may be around 14 mm. In one or more embodiments, the first radial distance R1 may be around 13 mm, such as 12.5 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 between sensing part of first electrode and first electrode part is about 1 mm.

The second sensing part 226B extends circularly at least 330 degrees around the stomal opening at a second radial distance R2 from the center point 19. The second radial distance R2 may be 18 mm. In one or more embodiments, the second radial distance R2 may be 17 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 between sensing part of second electrode and second electrode part is about 1 mm.

The third sensing part 228B extends circularly at least 330 degrees around the stomal opening at a third radial distance R3 from the center point 19. The third radial distance R3 is about 26 mm. In one or more embodiments, the third radial distance R3 is 21 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 between sensing part of third electrode and third electrode part is about 1 mm.

The ground electrode 222 comprises a fourth electrode part 240 for forming a ground or reference for the fourth electrode 230 and the fifth electrode 232. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point (such as a leakage radius R5 which may be around 32 mmm from the center point). The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm.

Figure 7:
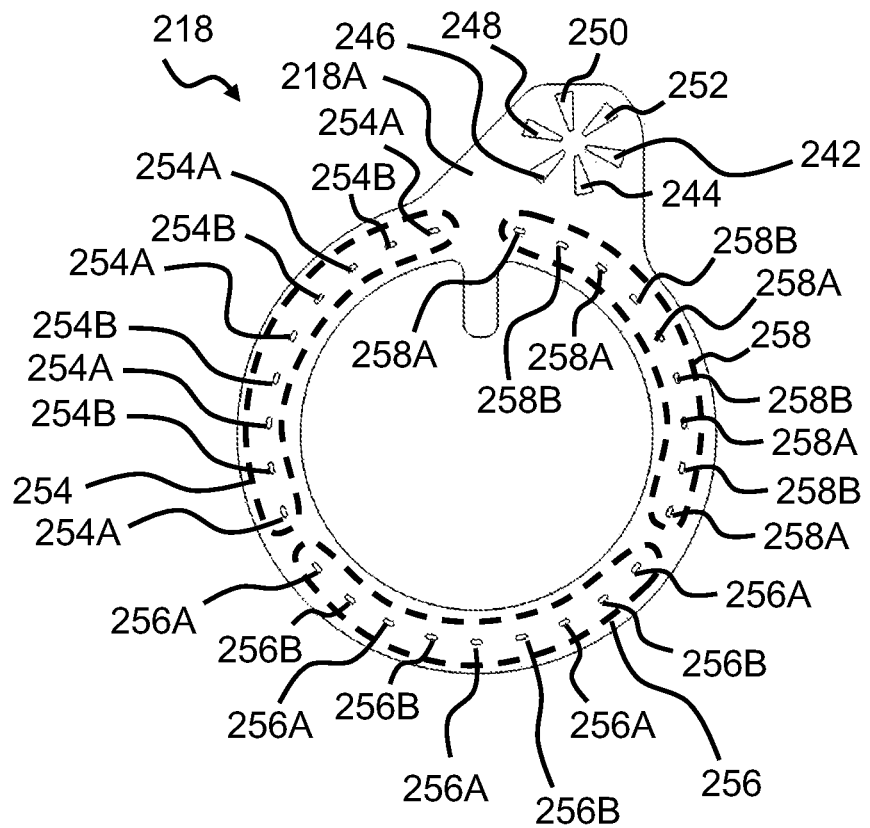
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
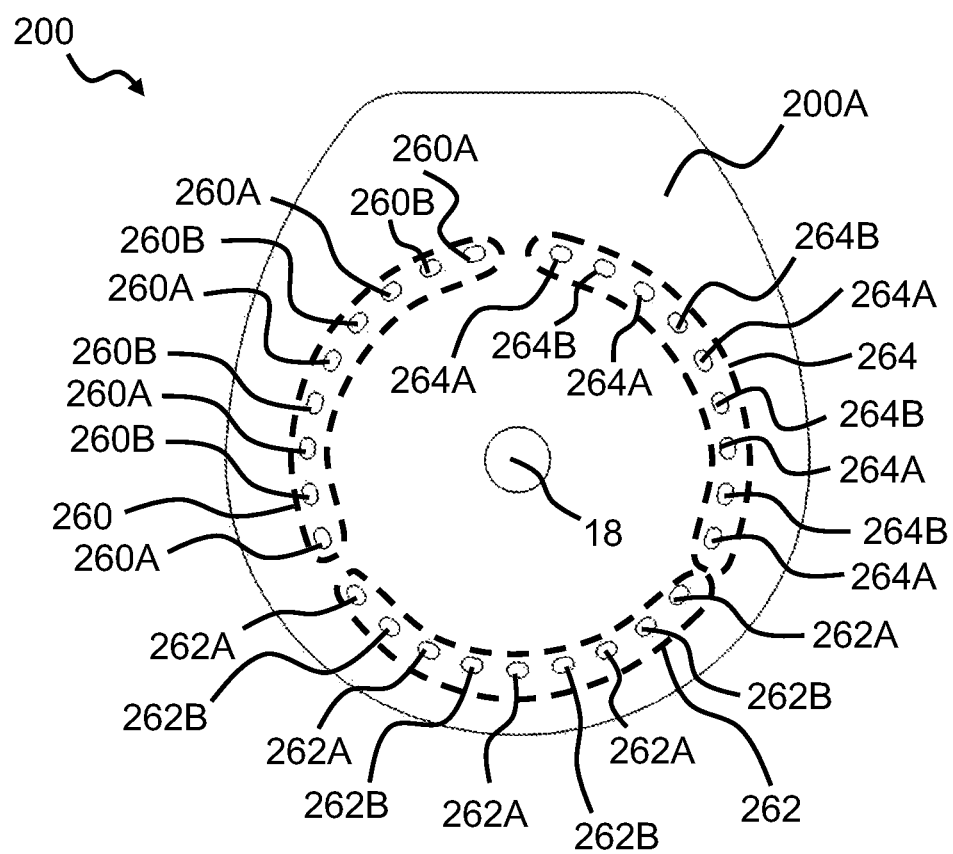
FIG. 8 is a distal view of an exemplary first adhesive layer.
Figure 9:
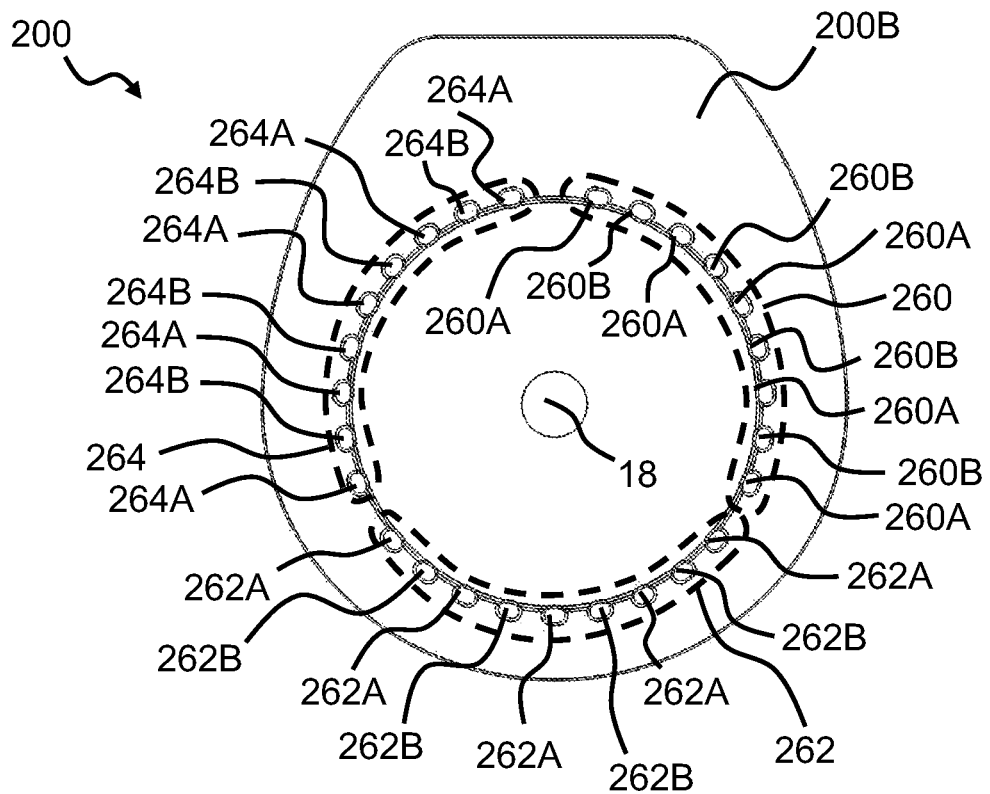
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary masking element, five primary first sensor point openings 260A each configured to overlap a part of the ground electrode 222. The primary sensor point openings 260 comprise, in the illustrated exemplary masking element, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary masking element, five secondary first sensor point openings 262A each configured to overlap a part of the fifth electrode 232. The secondary sensor point openings 262 comprise, in the illustrated exemplary masking element, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary masking element, five tertiary first sensor point openings 264A each configured to overlap a part of the fifth electrode 232. The tertiary sensor point openings 264 comprise, in the illustrated exemplary masking element, four tertiary second sensor point openings 264B each configured to overlap a part of the ground electrode 222. FIG. 9 is a proximal view of the first adhesive layer of FIG. 8.

Figure 10:
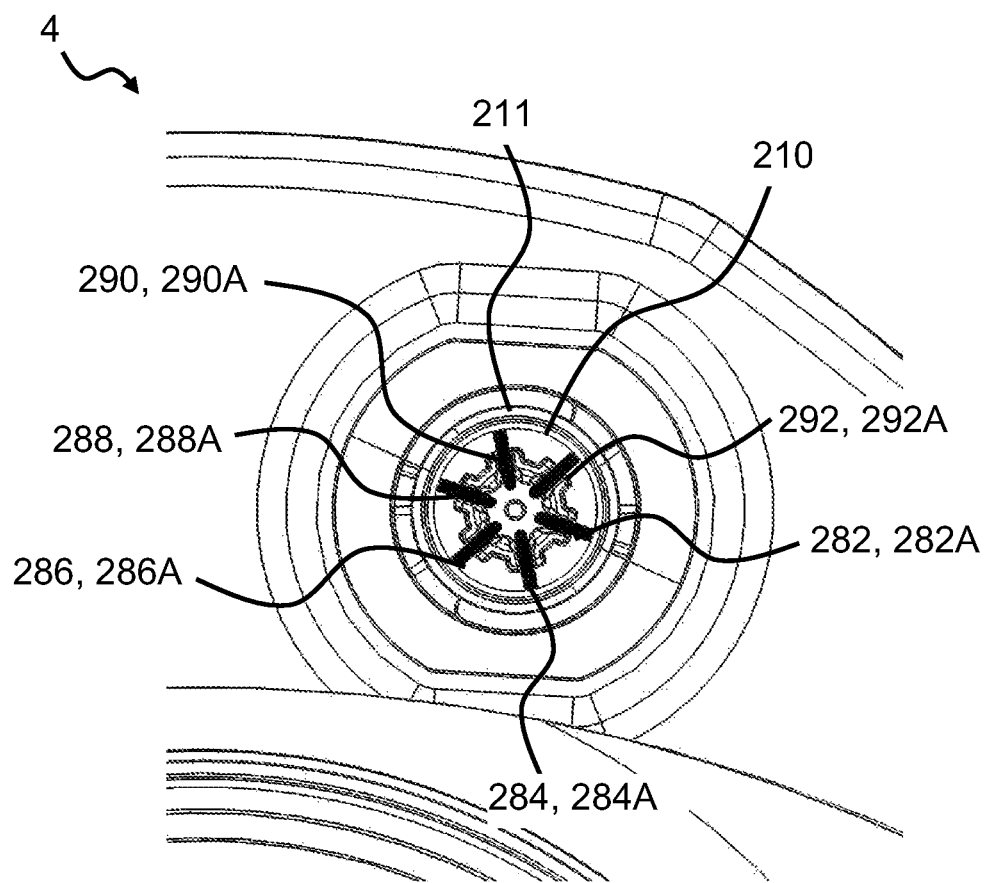
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 221/monitor interface comprises a plurality of terminals formed by respective terminal elements for forming respective electrical connections with respective terminals of the monitor device.

The plurality of terminals of the first connector 211/monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

Figure 11:
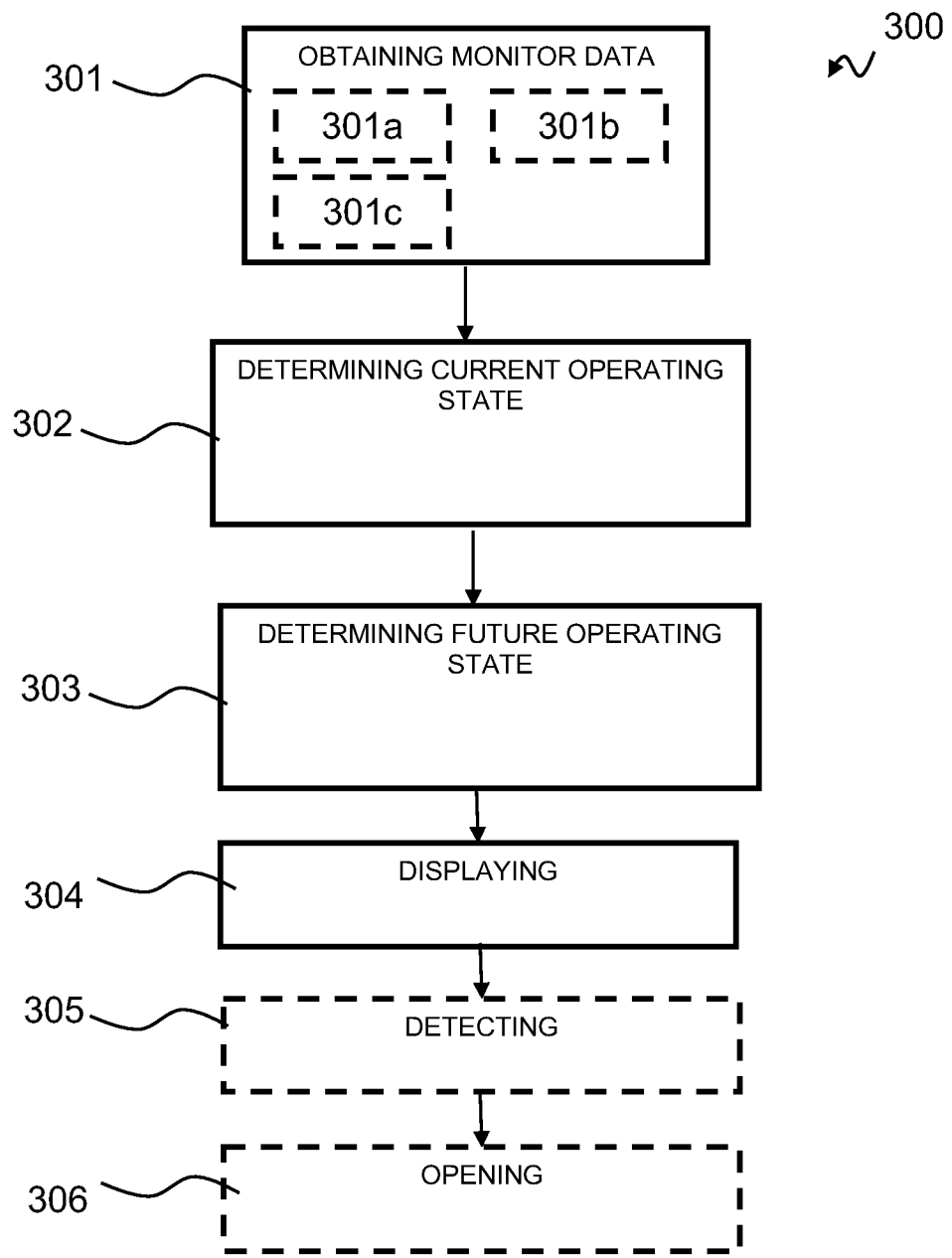
FIG. 11 illustrates an exemplary method according to the present disclosure.

FIG. 11 is a flow diagram of an exemplary method according to this disclosure. The method 300 is performed in an accessory device (e.g. accessory device of FIG. 1 and of FIG. 12). The method 300 is performed for providing (e.g. communicating, e.g. displaying) a future operating state of an ostomy appliance, such as of the disclosed base plate. This permits a monitoring of the disclosed ostomy system, e.g. monitoring of an operating state of an ostomy appliance, e.g. monitoring together a current operating state and a future operating state of an ostomy appliance. The method 300 may be performed for changing the ostomy appliance based on the current operating state and the future operating state of the ostomy appliance determined.

The accessory device 8 is configured to communicate with one or more devices of an ostomy system (e.g. ostomy system 1 of FIG. 1). As illustrated in FIG. 1, the ostomy system 1 comprises a monitor device 6, and/or an ostomy appliance 2 configured to be placed on a skin surface of a user.

The ostomy appliance 2 comprises a base plate 4 disclosed herein. The ostomy appliance comprises an ostomy pouch. The base plate 4 may comprise a first adhesive layer having a proximal side. During use, a proximal surface of the first adhesive layer adheres to the user's skin in the peristomal area and/or to additional seals, such as sealing paste, sealing tape and/or sealing ring. The base plate 4 may comprise one or more electrodes configured to measure electrical properties of the first adhesive layer. The electrical properties may be indicative of a conductive path in the first adhesive layer, thereby indicative of the moisture level, and indicative of the condition of the ostomy appliance 2.

The method 300 comprises obtaining 301 monitor data from the monitor device.

The method 300 comprises determining 302 a current operating state of the ostomy appliance based on the monitor data. The current operating state is indicative of current adhesive performance of the ostomy appliance.

The method 300 comprises determining 303 a future operating state of the ostomy appliance based on the monitor data and the current operating state. The future operating state is indicative of future (e.g. foreseen, predicted) adhesive performance of the ostomy appliance, and communicating the current operating state and the future operating state.

Obtaining 301 monitor data from the monitor device may comprise retrieving 301b and/or receiving 301a the monitor data from the monitor device.

Obtaining 301 monitor data from the monitor device may comprise obtaining 301c the monitor data over a time period.

The method 300 comprises determining 302 a current operating state of the ostomy appliance based on the monitor data. The current operating state is indicative of current adhesive performance of the ostomy appliance. The current operating state may comprise at least one of: a wear time, a quality of adhesion, a moisture pattern representation. Determining 302 may comprise determining the current operating state of the ostomy appliance based on the monitor data received over the time period. The time period may include a time period up to and possibly including a current time. The period of time may include a time period from a start time of use of any ostomy appliances, to the current time of determination of the current and/or future operating states. The time period may include a time period from a start time of use of the ostomy appliance, to the current time.

The method 300 comprises determining 303 a future operating state of the ostomy appliance based on the monitor data and optionally the current operating state. The future operating state is indicative of future adhesive performance of the ostomy appliance. The future operating state may comprise at least one of: a wear time, a quality of adhesion, a moisture pattern representation. Determining 303 may comprise determining the future operating state of the ostomy appliance based on the monitor data received over the time period.

Determining 302 or 303 may comprise determining the corresponding operating state of the ostomy appliance based on one or more previous operating states.

Determining 302 or 303 may comprise determining a current operating state of the ostomy appliance and a future operating state of the ostomy appliance based on one or more of: a parameter characterizing a product type of the ostomy appliance, a base plate parameter characterizing a product type of the base plate, a bag parameter characterizing a bag of the ostomy appliance, a ring parameter characterizing a ring type of the ostomy appliance, a power capacity of the monitor device and a user attribute.

Determining 302 or 303 may be performed by a statistical analysis to the previous operating states, and/or to historic monitor data.

The method comprises displaying 304, on the display of the accessory device, a first user interface screen comprising a first primary user interface object representing the current operating state and/or a first secondary user interface object representing the future operating state. The method may comprise displaying 304, on the display of the accessory device, a first user interface screen comprising a first secondary user interface object representing the future operating state. Displaying 304 the first user interface screen may comprise displaying a first notification.

The method 300 may comprise detecting 305 a first input selecting any of the first primary user interface object and secondary user interface object. The method 300 may comprise in response to detecting the first input, opening 306 an ostomy user application, (e.g. an ostomy user application installed on the accessory device). The method 300 may comprise: in response to opening the ostomy user application, displaying a second user interface screen comprising a second primary user interface object representing the current operating state of the ostomy appliance and a second secondary user interface object representing the future operating state Determining 302 the current operating state of the ostomy appliance (e.g. of the disclosed base plate) may be based on the monitor data received over a period of time (e.g. over a set of time periods). Determining 303 the future operating state of the ostomy appliance (e.g. of the disclosed base plate) may be based on the monitor data received over a period of time (e.g. over a set of time periods). The time period may include a period of time up to and including the current time. The time period may include a time period from a start time of use of the ostomy appliance, to the current time. The time period may include a time window that periodically occurs, such as a morning time period, an afternoon time period, a night time period, a daily time period, a weekly time period etc . . . .

Determining 303 the future operating state of the ostomy appliance (e.g. at a given time) may be based on previous operating states determined for a corresponding time window.

The method may comprise displaying, e.g. in the second user interface screen, third user interface objects representing previous operating states, the current operating state, and one or more future operating states mapped over a time window comprising elapsed time prior to the current time, current time and future time period after the current time.

The method 300 may comprise displaying, e.g. in the second user interface screen, a fifth user interface object indicative of the connection between the monitor device and the base plate.

The method 300 may comprise displaying, e.g. in the second user interface screen, a sixth user interface object indicative of battery status of the monitor device. The sixth user interface object may indicate a remaining battery time, and/or a remaining battery percentage (e.g. state of charge).

The method may comprise displaying, on the display, a fourth user interface object. The method may comprise detecting a second input selecting the fourth user interface object. The method may comprise in response to detecting the second input, displaying a visual indicator indicating to the user to perform (e.g. and/or to initiate) a change of base plate. For example, in one or more exemplary methods, displaying the visual indicator indicating to the user to perform the change of base plate comprises displaying a first prompt indicating to the user to remove the monitor device from the used base plate.

The method 300 may comprise detecting, based on the monitor data, removal of the monitor device from the base plate; and updating accordingly the display of the fifth or sixth user interface object to indicate lack of connection between the monitor device and the base plate. In one or more exemplary methods, displaying the visual indicator indicating to the user to perform the change of base plate comprises displaying a second prompt indicating to the user to apply a new base plate.

The method 300 may comprise capturing an image of peristomal area of the user. In one or more exemplary methods, displaying the visual indicator indicating to the user to perform the change of base plate comprises displaying a third prompt indicating to the user to attach the monitor device to the new base plate.

The method 300 may comprise detecting, based on the monitor data, attachment of the monitor device to the base plate, and updating accordingly the display of the fifth and/or sixth user interface object to indicate an established connection between the monitor device and the base plate.

The method 300 may comprise determining whether the change of base plate satisfies a success criterion, and in accordance with the determination that the change of base plate satisfies the success criterion, displaying a seventh user interface object indicating that the ostomy system is operational. In one or more exemplary methods, the success criterion comprises a primary success criterion, and when the primary success criterion is satisfied when the monitor device is connected properly to the base plate. The success criterion may comprise a secondary success criterion, and wherein when the secondary success criterion is satisfied when the monitor device is connected properly to accessory device.

The method may comprise storing one or more events related to any one or more of the displaying of the prompts and of the displaying of the user interface objects.

The method may comprise storing one or more current operating states as determined in the present disclosure.

The method may comprise storing one or more future operating states as determined in the present disclosure.

In one or more exemplary methods, the success criterion is satisfied when the primary success criterion is satisfied, and when the secondary success criterion is satisfied. In one or more exemplary methods, the success criterion is satisfied when the primary success criterion is satisfied.

In one or more exemplary methods, displaying a seventh user interface object indicating that the ostomy system is operational comprises displaying the seventh user interface object indicative of the current operating state being operational on a home screen, and/or on a lock screen. The ostomy system being operational may refer to the ostomy system being properly set, including the monitor device being properly connected to the accessory device and to the base plate. For example, the ostomy system is operational when the ostomy system is properly configured and installed such that the monitor device monitors the base plate, and/or the accessory device monitors the base plate In one or more exemplary methods, displaying a seventh user interface object indicating that the ostomy system is operational comprises displaying the seventh user interface object in a third user interface screen of the ostomy user application.

The method 300 may comprise obtaining an operating state of the ostomy appliance (e.g. a current operating state and/or a future operating state, e.g. by performing the determining 302 and/or 303); determining whether the operating state (e.g. the current operating state and/or the future operating state) satisfies a change criterion; and in accordance with the operating state satisfying a change criterion, performing the displaying of the first user interface screen comprising the first primary user interface object and the first secondary user interface object. The change criterion may be met when it is determined that the operating state (e.g. the current operating state and/or the future operating state (e.g. very near future operating state, e.g. within 1 h, 45 min, 30 min, e.g. 15 min, e.g. within 10 min, e.g. within 5 min from the current time)) is indicative of a remaining wear time that is at or below a wear threshold (e.g. a time sufficient for operating a change of ostomy appliance, e.g. 45 min, e.g. 30 min, e.g. 20 min, e.g. 15 min, e.g. 10 min). The change criterion may be based on the first parameter data, the second parameter data and/or the third parameter data as disclosed herein. The change criterion may be fulfilled if parameter data changes, e.g. if a change in parameter data is larger than a change threshold, which may be indicative of imminent leakage to come.

The method 300 may comprise determining a status of an ostomy inventory of the user, and displaying, e.g. on a fourth user interface screen, one or more user interface objects representative of the status. The status of the ostomy inventory may comprise inventory status related to one or more bags, inventory status related to one or more base plates, inventory status related to one or more rings.

Figure 12:
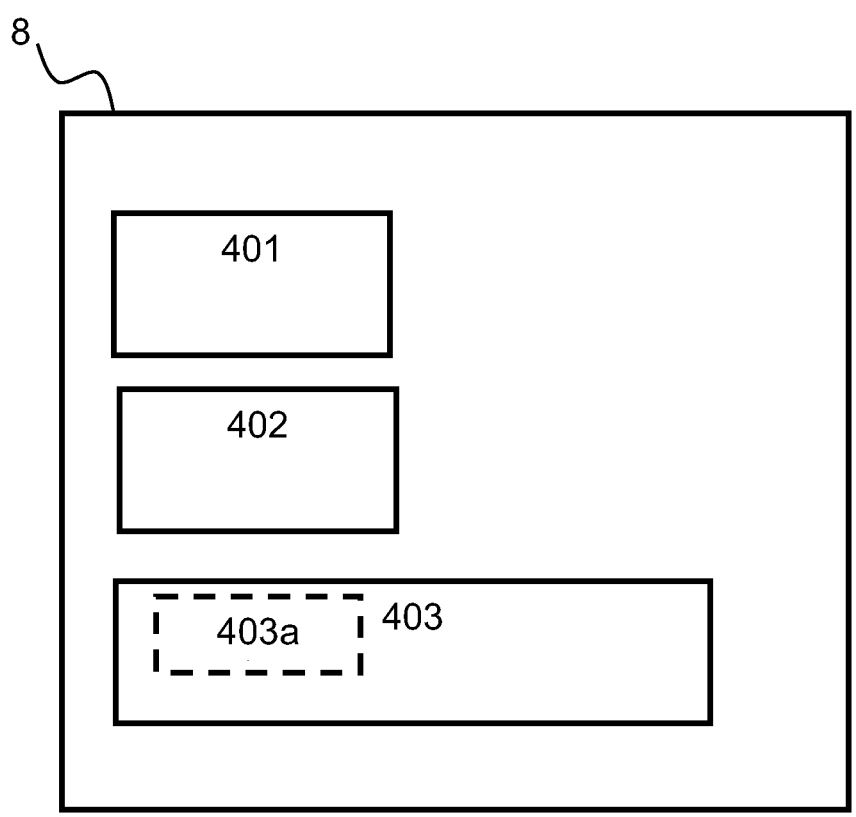
FIG. 12 illustrates an exemplary accessory device according to the present disclosure.

FIG. 12 is a block diagram illustrating an exemplary accessory device 8 according to the present disclosure. The accessory device 8 forms part of an ostomy system and is capable of determining of the current and/or future operating states of an ostomy appliance to be placed on a user's skin, in particular of determining and displaying a future operating state. The accessory device 8 comprises a memory 401; a processor 402 coupled to the memory 401; and an interface 403 coupled to the processor 402.

The interface 403 is configured to communicate with one or more devices of the ostomy system. The one or more devices comprise a monitor device disclosed herein, and/or an ostomy appliance configured to be placed on a skin surface of a user or on any additional seals. The ostomy appliance comprises a base plate. The base plate may comprise a first adhesive layer having a proximal side. During use, a proximal surface of the first adhesive layer adheres to the user's skin in the peristomal area and/or to additional seals, such as sealing paste, sealing tape and/or sealing ring. The base plate may comprise one or more electrodes configured to measure electrical properties of the first adhesive layer. The electrical properties may be indicative of a conductive path in the first adhesive layer, thereby indicative of the moisture level, and indicative of the condition of the ostomy appliance.

The interface 403 is configured to obtain monitor data from the one or more devices, such as to receive or retrieve the monitor data from the monitor device. The monitor data may be indicative of a condition of the ostomy appliance, such as a condition of a proximal side of a layer of the ostomy appliance (e.g. a first adhesive layer of the base plate) that is directed towards the skin surface.

The interface 403 comprises a display 403a, and a transceiver module. The display 403a is configured to display user interface screens including one or more user interface objects. The display 403a may be configured to detect contact, such as touch input, from the user. The display 403a may be a touch-sensitive display. The display 403a may comprise a touch-sensitive surface.

The processor 402 may be configured to determine a current operating state and a future operating state of the ostomy appliance based on the monitor data obtained. The current operating state may be indicative of adhesive performance of the ostomy appliance (e.g. of the base plate).

The processor 402 is configured to determine a future operating state of the ostomy appliance (e.g. the future operating state of the base plate of the ostomy appliance) based on the monitor data. The future operating state is indicative of a future (e.g. predicted future, foreseen future) adhesive performance of the ostomy appliance (e.g. of the future (e.g. predicted future, foreseen future) adhesive performance of the base plate of the ostomy appliance).

The current operating state may comprise at least one of: a wear time, a quality of adhesion, and a moisture pattern representation. The future operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time.

The processor 402 may be configured to determine the current operating state and/or the future operating state by determining a moisture pattern type. The moisture pattern type may be based on monitor data comprising one or more, such as all, of first monitor data, second monitor data, and third monitor data, such as first parameter data, second parameter data and the third parameter data. The first primary parameter data may be indicative of the resistance between the first electrode pair (first electrode and first electrode part of the ground electrode) of the base plate. The second primary parameter data may be indicative of the resistance between the second electrode pair (second electrode and second electrode part of the ground electrode) of the base plate. The third primary parameter data may be indicative of resistance between the third electrode pair (third electrode and third electrode part of the ground electrode) of the base plate.

The adhesive performance of the ostomy appliance is, inter alia, indicative of or comprises adhesive failure of the base plate and/or leakage risk of the ostomy appliance and/or indicative of the risk of skin damage to the user of the ostomy system. For example, determination of a moisture pattern type may comprise selecting a moisture pattern type from a set of predefined moisture pattern types (e.g. comprising four to twenty moisture pattern types).

The processor 402 may be configured to determine one or more future moisture pattern types by comparing the first parameter data and/or the second parameter data, by determining whether the first parameter data and/or the second parameter data satisfy one or more criteria, and identifying a future moisture pattern type based on the determination.

For example, determining one or more moisture pattern types comprises determining whether at least one of the first parameter data, the second parameter data, and optionally the third parameter data meets first criteria related to moisture pattern, and the moisture pattern type is set to the first moisture pattern type if the first criteria related to moisture pattern are met. For example, the first criteria may comprise a first primary criterion based on the first parameter data, a first secondary criterion based on the second parameter data, and optionally a first tertiary criterion based on the third parameter data. For example, the first criteria related to moisture pattern may be given by e.g. or at least may comprises:

(P_1_1<TH_1_1),
(P_2_1<TH_1_2) and
(P_3_1<TH_1_3), wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value and wherein the first moisture pattern type may be indicative of operating state with high risk (e.g. high severity and/or high imminence) of leakage.

In one or more exemplary accessory devices, determining one or more moisture pattern types comprises determining whether at least one of the first parameter data, the second parameter data, and the third parameter data meets second criteria related to moisture pattern, and the moisture pattern type is set to the second type if the second criteria are met. For example, the second criteria related to moisture pattern may be given by e.g. or at least may comprise:

(P_1_1>TH_2_1),
(P_2_1>TH_2_2), and
(P_3_1>TH_2_3)

wherein P_1_1 is a first primary parameter based on the first parameter data, TH_2_1 is a second primary threshold value, P_2_1 is a second primary parameter based on the second parameter data, TH_2_2 is a second secondary threshold value, P_3_1 is a third primary parameter based on the third parameter data, TH_2_3 is a second tertiary threshold value, and wherein the second moisture pattern type is indicative of operating state with low risk (e.g. low severity and/or low imminence) of leakage.

In one or more exemplary accessory devices, determining one or more moisture pattern types comprises determining whether at least one of the first parameter data, the second parameter data, and the third parameter data meets third criteria related to moisture pattern. The moisture pattern type may be set to the third moisture pattern type if the third criteria related to moisture pattern are met. In one or more exemplary methods, the second criteria are given by or at least may comprise:

(P_1_1>TH_2_1),
(P_2_1>TH_2_2), and
(P_3_1>TH_2_3), wherein P_1_1 is a first primary parameter, optionally indicative of resistance between respective electrodes, based on the first parameter data, TH_2_1 is a second primary threshold value, P_2_1 is a second primary parameter, optionally indicative of resistance between respective electrodes, based on the second parameter data, TH_2_2 is a second secondary threshold value, P_3_1 is a third primary parameter, optionally indicative of resistance between respective electrodes, based on the third parameter data, TH_2_3 is a second tertiary threshold value, and wherein the second moisture pattern type is indicative of operating state with low risk (e.g. low severity and/or low imminence) of leakage.

In one or more exemplary accessory devices, determining one or more moisture pattern types comprises determine a moisture pattern type if a determination trigger criterion is fulfilled. The determination trigger criterion may be based on the first parameter data, the second parameter data and/or the third parameter data. The determination trigger criterion may be fulfilled if parameter data changes, e.g. if a change in parameter data is larger than a change threshold.

In one or more exemplary accessory devices, determining one or more moisture pattern types based on the monitor data comprises comparing first parameter data and second parameter data. In one or more exemplary methods, determining one or more moisture pattern types based on the monitor data comprises identifying a moisture pattern type based on the comparison. In one or more exemplary accessory devices, determining one or more moisture pattern types based on the monitor data comprises comparing first parameter data, second parameter data, and third parameter data. In one or more exemplary accessory devices, determining one or more moisture pattern types based on the monitor data comprises identifying a moisture pattern type based on the comparison. For example, an exemplary criterion, such as one or more of a first criterion (of the first criteria), a second criterion (of the second criteria) and a third criterion (of the third criteria), may be based on a difference and/or rate between parameter data and/or parameters derived from parameter data. For example, determining a moisture pattern comprises determining a first tertiary parameter, also denoted P_1_3, indicative of a time delay between changes in the first parameter data and the second parameter data, such as a time delay between the first parameter data reaching (or being below) a first threshold and the second parameter data reaching (or being below) a second threshold. A high time delay (P_1_3>TH_D_1) may be indicative of leakage of faecal material (and thus high risk of skin damage), while a low time delay (P_1_3<TH_D_1) may be indicative of the ostomate perspiring or sweating. One or more criteria may be based on the first tertiary parameter. For example, determining a moisture pattern comprises determining a third tertiary parameter, also denoted P_3_3, indicative of a time delay between changes in the third parameter data and the fourth parameter data, such as a time delay between the third parameter data reaching (or being below) a third threshold and the fourth parameter data reaching (or being below) a fourth threshold. A high time delay (P_3_3>TH_D_3) may be indicative of leakage of faecal material (and thus high risk of skin damage), while a low time delay (P_3_3<TH_D_1) may be indicative of the ostomate perspiring or sweating. One or more criteria may be based on the third tertiary parameter.

The processor 402 is configured to provide data for display, on the display 403a, a first user interface screen comprising a first primary user interface object representing the current operating state and/or a first secondary user interface object representing the future operating state.

The processor 402 is configured to perform any of the methods step disclosed herein.

The processor 402 is configured to provide data for display, on the display 403a, any of the user interfaces of FIGS. 13a-e.

The processor 402 is configured to provide data for transmission of one or more current and/or operating states via the interface 403, to the user, and/or to any other accessory devices in possession of the user.

FIG. 13a-e show exemplary user interfaces displayed on an exemplary accessory device for providing both the current and future operating states of an ostomy appliance (e.g.

a base plate disclosed herein) and for assisting change of the base plate based on the current operating state according to the present disclosure.

Figure 13A:
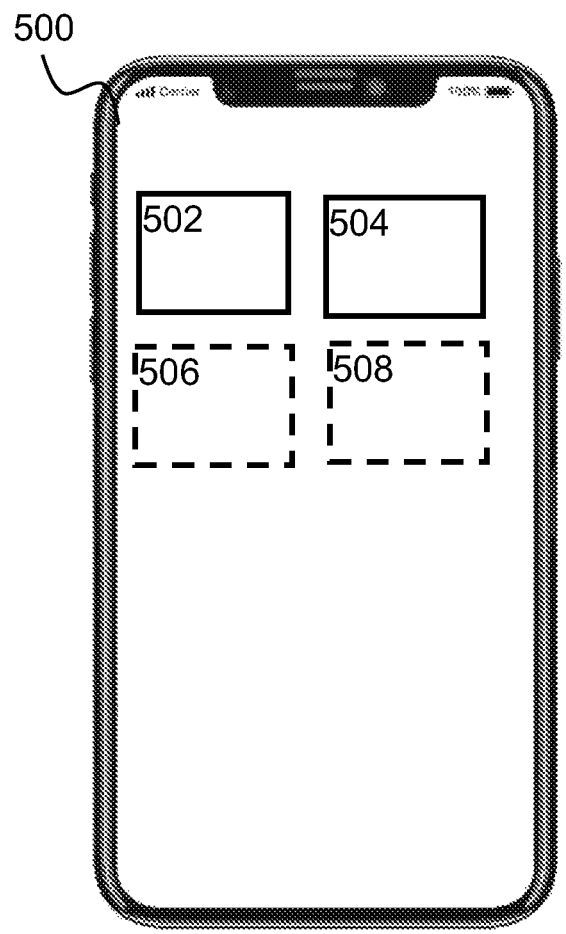
FIGS. 13a-e illustrate exemplary user interfaces according to the present disclosure.

FIG. 13a shows an exemplary user interface for monitoring or communicating the current and future operating states of an ostomy appliance. The user interface comprises a first user interface screen 500 comprising a plurality of user interface objects, e.g. a first primary user interface object 502 representing the current operating state, a first secondary user interface object 504 representing the future operating state. The first user interface screen 500 may comprise additional user interface objects 506, 508 representing previous operating states.

The first user interface screen 500 may comprise a lock screen of the accessory device, and/or a home screen of the accessory device.

A first input selecting any of the first primary user interface object 502 and secondary user interface object 504 may be detected by the accessory device, and in response to detecting the first input, the accessory device launches or opens an ostomy user application, (e.g. an ostomy user application installed on the accessory device). For example, detection of first input that corresponds to selection any of user interface objects 502, 504, 506, 508 triggers the launch and opening of the ostomy user application installed on the accessory device, as shown in corresponding user interface screens of FIGS. 13b-e.

Figure 13B:
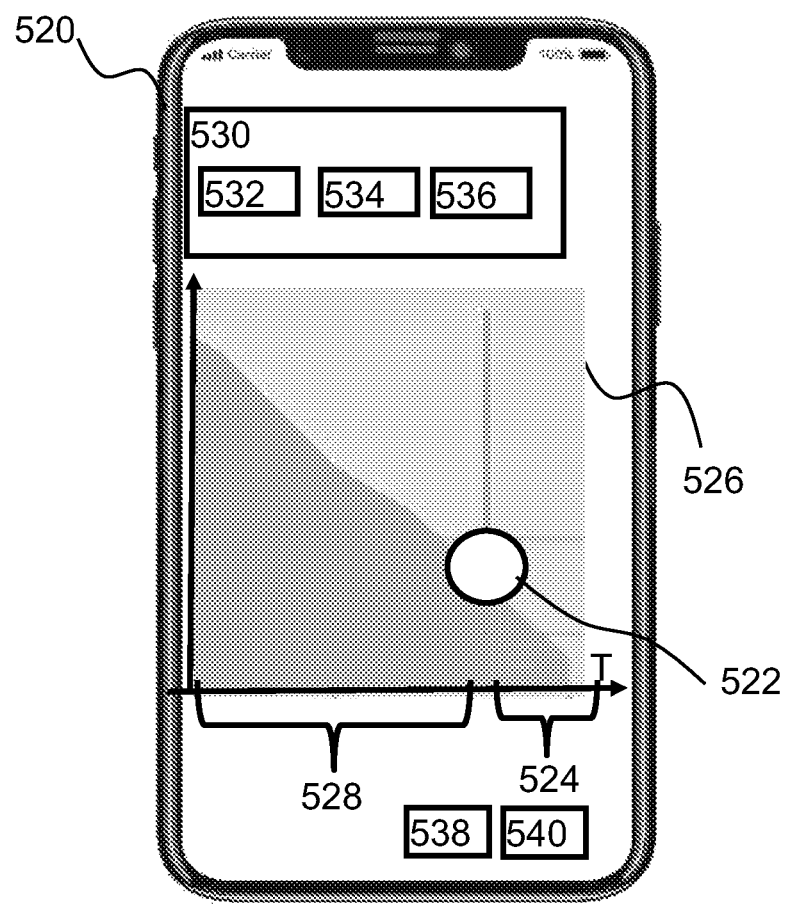

FIG. 13b shows an exemplary user interface of an ostomy user application comprising a second user interface screen 520. The second user interface screen 520 comprises a second primary user interface object 522 representing the current operating state of the ostomy appliance and a second secondary user interface object 524 representing the future operating states. The second primary user interface object 522 representing the current operating state of the ostomy appliance may be a graphical variation of the first primary user interface object 502 (e.g. increased or decreased in size, resolution; providing more precise information regarding the respective operating states). The second secondary user interface object 524 representing the future operating state of the ostomy appliance may be a graphical variation of the first secondary user interface object 504 (e.g. increased or decreased in size, resolution; providing more precise information regarding the respective operating state), e.g. to provide some continuity in the man-machine interaction.

The second user interface screen 520 comprises user interface object 526 representative of a graph of a function or of a set that provides third user interface objects 528 representing previous operating states, second primary user interface object 522 representing the current operating state and second secondary user interface object 524 representative of one or more future operating states over time T, e.g. over a time window comprising at least of part of an elapsed time prior to the current time, current time and a future time period after the current time. The graph comprises values indicative of operating states in the y-axis. The operating state may comprise wear time such as remaining wear time.

The second user interface screen 520 may comprise a user interface object 530 representing a summary status of the base plate comprising an elapsed wear time user interface object 532 and a recommendation user interface object 534. The elapsed wear time user interface object 532 may be an indicator of the elapsed wear time for the presently worn ostomy appliance, such as the presently worn base plate. The elapsed wear time user interface object 532 may comprise a day indicator and an hour indicator (e.g. 2 Days and 15 h). The recommendation user interface object 534 may be a text prompt in the like of: "Your base plate is worn, Change is recommended," "Everything is fine, no problems detected".

The second user interface screen 520 comprising the second primary user interface object 522 representing the current operating state of the ostomy appliance and the second secondary user interface object 524 representing the future operating state is displayed in response to opening the ostomy user application.

The second user interface screen 520 may be seen as one of the user interface screen displayed by the ostomy user application.

The second primary user interface object 522 representing the current operating state of the ostomy appliance may have a graphical representation derived from the graphical representation of the first primary user interface object 502 (e.g. increased or decreased in size, resolution; providing more precise information regarding the respective operating states).

The second user interface screen 520 may comprise a user interface object 536 to access user settings of the user ostomy application.

The second user interface screen 520 may comprise a fifth user interface object 538 indicative of the connection between the monitor device and the base plate. The fifth user interface object 538 may indicate a connection state for the connection between the monitor device and the base plate (such as connected, not connected, searching, failed connection).

The second user interface screen 520 may comprise a sixth user interface object 540 indicative of battery status of the monitor device. The sixth user interface object 540 may indicate a remaining battery time, and/or a remaining battery percentage (e.g. state of charge).

The user interface object 530 representing a summary status of the base plate may serve as the fourth user interface object. Detecting a second input selecting the fourth user interface object 530 and in response to detecting the second input, the accessory device is configured to display a visual indicator indicating to the user to perform (e.g. and/or to initiate) a change of base plate (e.g. in user interface screen 550 of FIG. 13c).

Figure 13C:
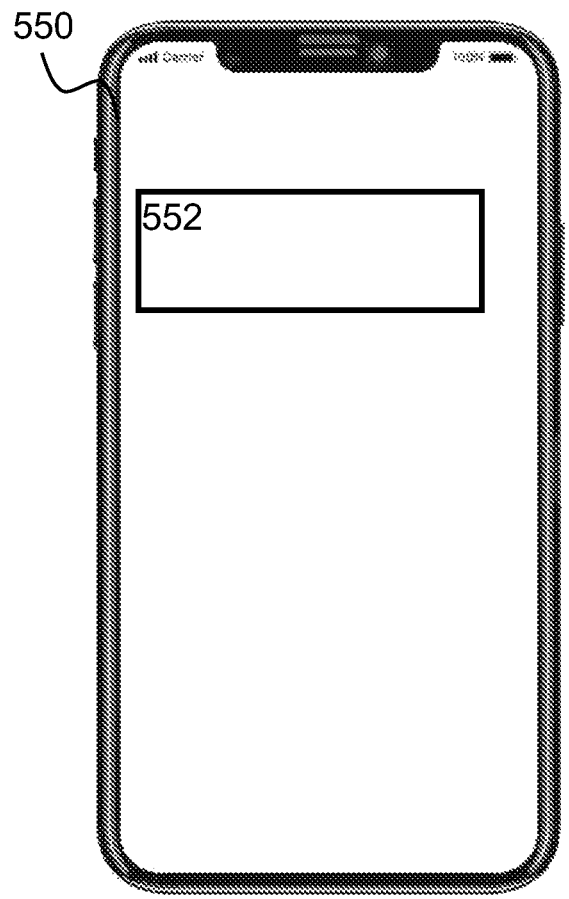

FIG. 13c shows exemplary user interface of an ostomy user application comprising a user interface screen 550. The user interface screen 550 comprises a visual indicator indicating to the user to perform (e.g. and/or to initiate) a change of base plate (e.g. in user interface screen 550 of FIG. 13c). The visual indicator may be a first prompt 552. The first prompt 552 may comprise a text prompt in the line of "change base plate" or "change your ostomy appliance".

Figure 13D:
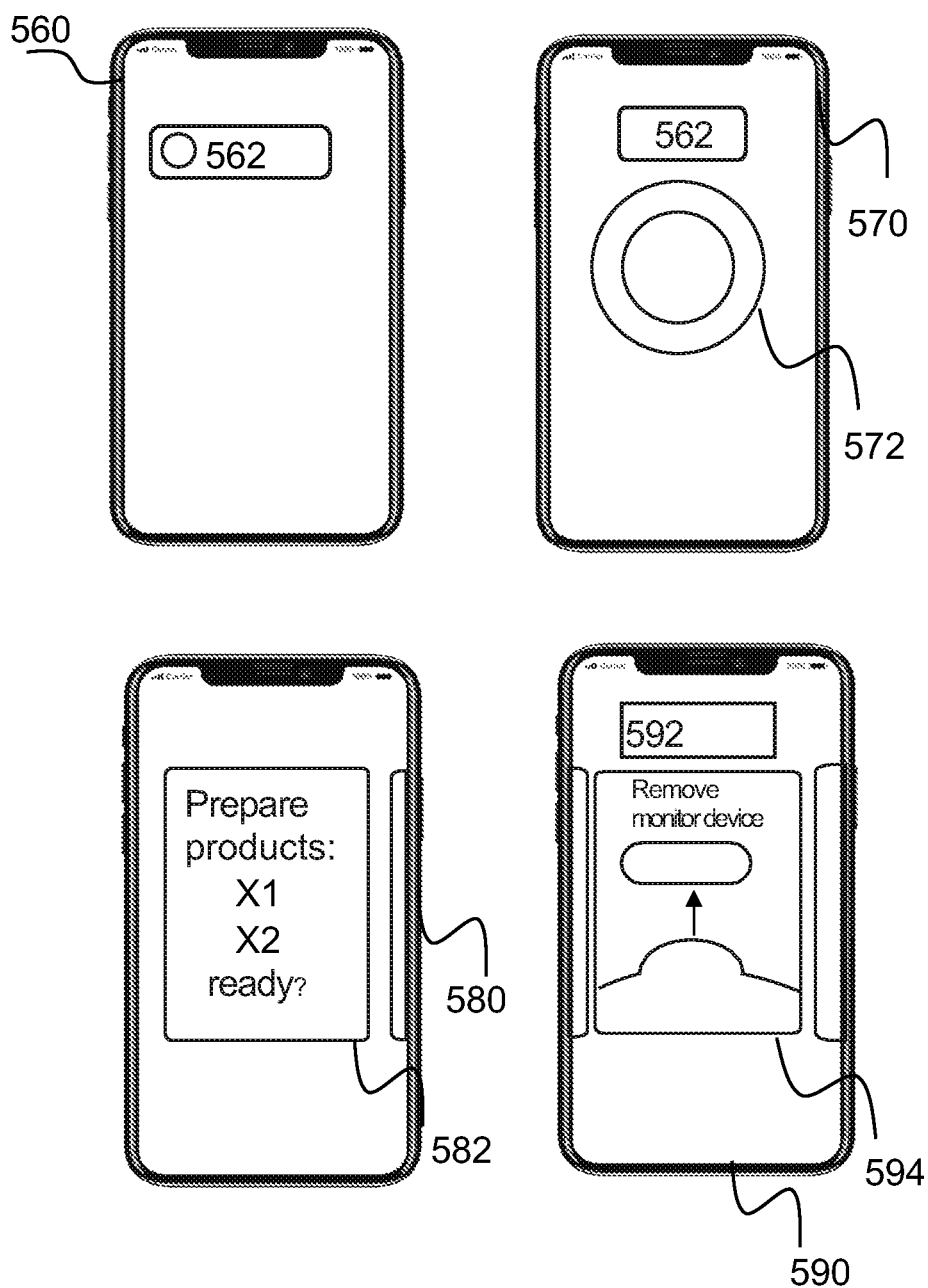

FIG. 13d shows exemplary user interfaces of an ostomy user application comprising a user interface screen 560, 570, 580, and 590.

User interface screen 560 includes a user interface object 562 prompting the user to change base plate. The user interface object 562 may be displayed on the lock screen as shown in user interface screen 560 and/or within the user ostomy application as shown in user interface screen 570. In other words, the user interface screen 560 may be a lock screen. The user interface screen 560 may be a home screen. The user interface screen 570 is one of the user interface screens of the user ostomy application. The user interface screen 570 may comprise a user interface object 572 indicative of current and/or future operating state.

The user interface screen 580 comprises a prompt 582 to prepare accessory products for change: X1, X2 (e.g. cut base plate, scissors, bag, wipes, waste bag, removal spray, monitor device for change) and to check on whether the accessory products are ready.

The user interface screen 590 comprises a prompt 592 requesting to start the change of base plate by removing the monitor device and a prompt 594 to remove the monitor device along with a picture to guide the user.

Figure 13E:
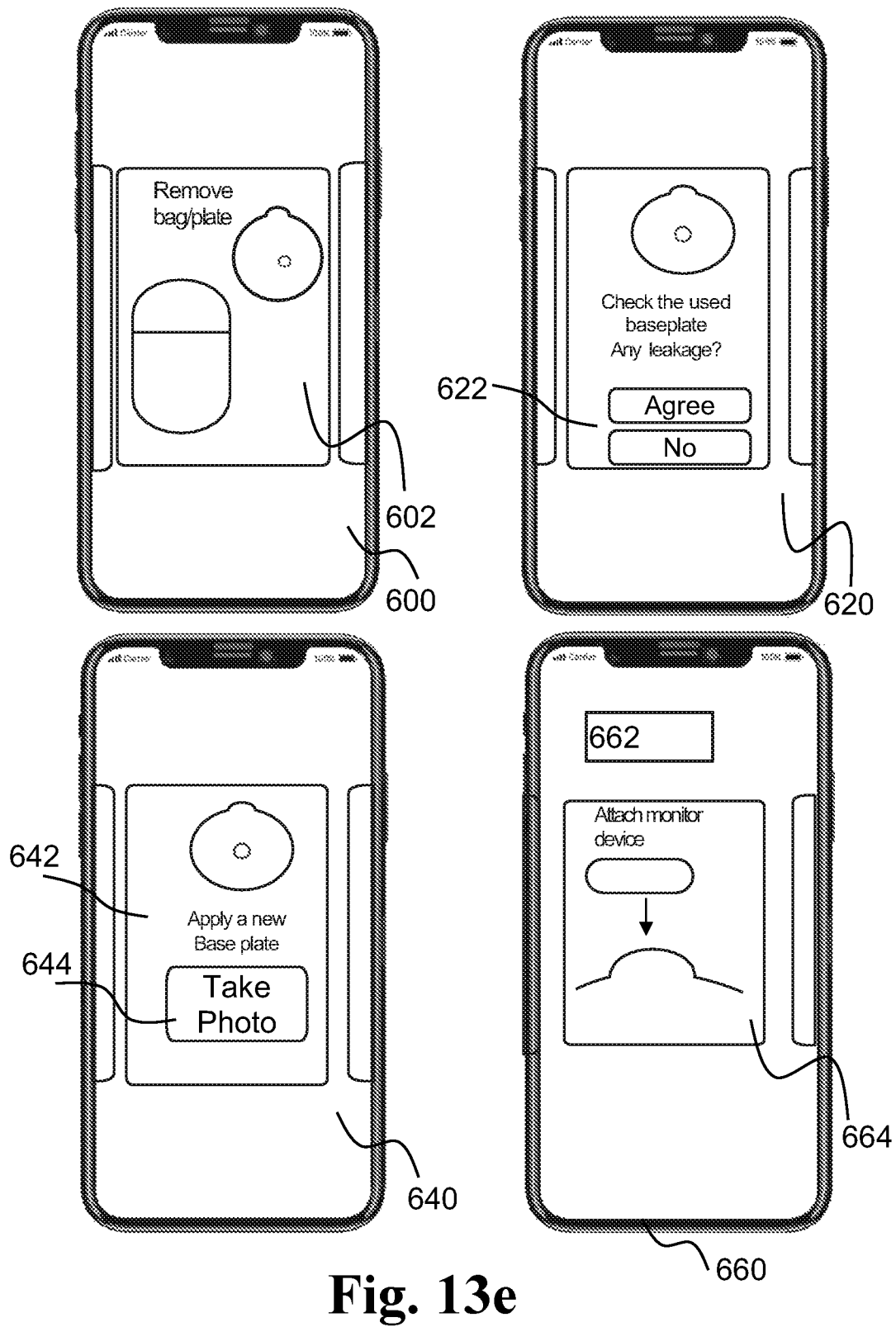

The user interface screen 590 may be followed by user interface screens that include a prompt to remove the used base plate and/or used bag (e.g. user interface screen 600 of FIG. 13*e*).

FIG. 13*e* shows exemplary user interfaces of an ostomy user application comprising a user interface screen 600, 620, 640 and 660.

The user interface screen 600 includes a user interface object 602, indicating to remove the used base plate and/or used bag.

The user interface screen 620 includes a user interface object 622, requesting the user to indicate whether the displayed current operating state determined as leakage corresponds to the operating state perceivable by the user (e.g. an "agree" user interface object, and "no") when the base plate is removed so as to confirm the determination and display of the current operating state or so as to remedy an erroneous determination and display thereof.

The user interface object 622, may be a user interface object requesting the user to indicate whether the displayed future operating state determined as imminent predicted leakage corresponds to the immediate operating state perceivable by the user (e.g. an "agree" user interface object, and "no") when the base plate is removed so as to confirm the determination and display of the future operating state or so as to remedy an erroneous determination and display thereof.

The user interface screen 620 may be followed by user interface screens including one or more prompts to clean the peristomal area, one or more prompts to check the skin condition of the peristomal area, and one or more prompts to clean the used monitor device.

The user interface screen 640 includes a user interface object or second prompt 642 indicating to the user to apply a new base plate and a user interface object 644 which is an affordance that enables the capture of an image so that the user can capture an image of peristomal area by selecting the affordance 644 (e.g. when the accessory device detects a user input related to affordance 644, the accessory device may open a digital viewfinder).

The user interface screen 660 includes a user interface object 662 and a third prompt 664 to indicate to the user to attach the monitor device to the new base plate.

Figure 14:
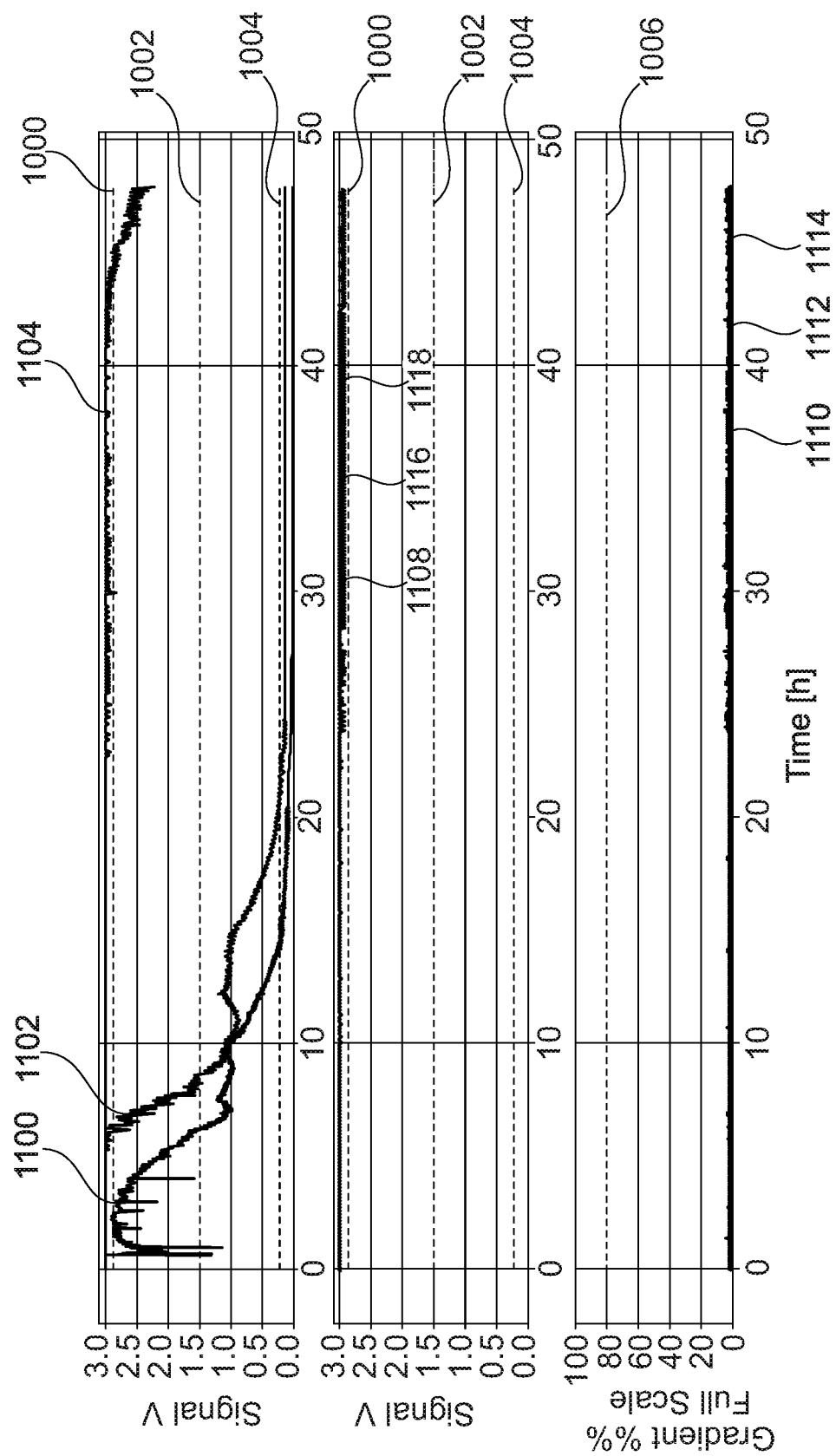
FIG. 14 is an exemplary graphical representation of parameter data as a function of time.

FIG. 14 shows an exemplary graphical representation of parameter data as a function of time. In this example, the parameter data in the y-axis is in Volts and time is in the x-axis. Curve 1100 shows, as a function of time, first parameter data indicative of voltage measured by the first electrode pair of the base plate. Curve 1102 shows, as a function of time, second parameter data indicative of voltage measured by the second electrode pair of the base plate. Curve 1104 shows, as a function of time, third parameter data indicative of voltage measured by the third electrode pair of the base plate. Curves 1108, 1116, 1118 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1110, 1112, 1114 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 14 shows the upper voltage threshold value represented as curve 1000, the medium voltage threshold value represented as curve 1002, the lower voltage threshold value represented as curve 1004, and curve 1006 is a gradient limit.

Curves 1108, 1116, 1118 as well as curves 1110, 1112, 1114 show that no moisture is detected at the proximal side of the first adhesive layer by the fourth electrode pair.

At a time less than 5 h, curve 1100 shows that moisture is detected by the first electrode pair as the first parameter data crosses the upper voltage threshold value while curve 1102 shows that moisture is not detected by the second electrode pair as the second parameter data has not crossed the upper voltage threshold value. At this stage, it is determined that the ostomy appliance is in a first operating state.

At time between 5 h and 10 h, curve 1102 shows that moisture is detected by the second electrode pair as the second parameter data crosses the upper voltage threshold value. At this stage, it is determined that the ostomy appliance is in a second operating state.

At time around 45 h, curve 1104 shows that moisture is detected by the third electrode pair as the third parameter data crosses the upper voltage threshold value. At this stage, it is determined that the ostomy appliance is in a third operating state.

Figure 15:
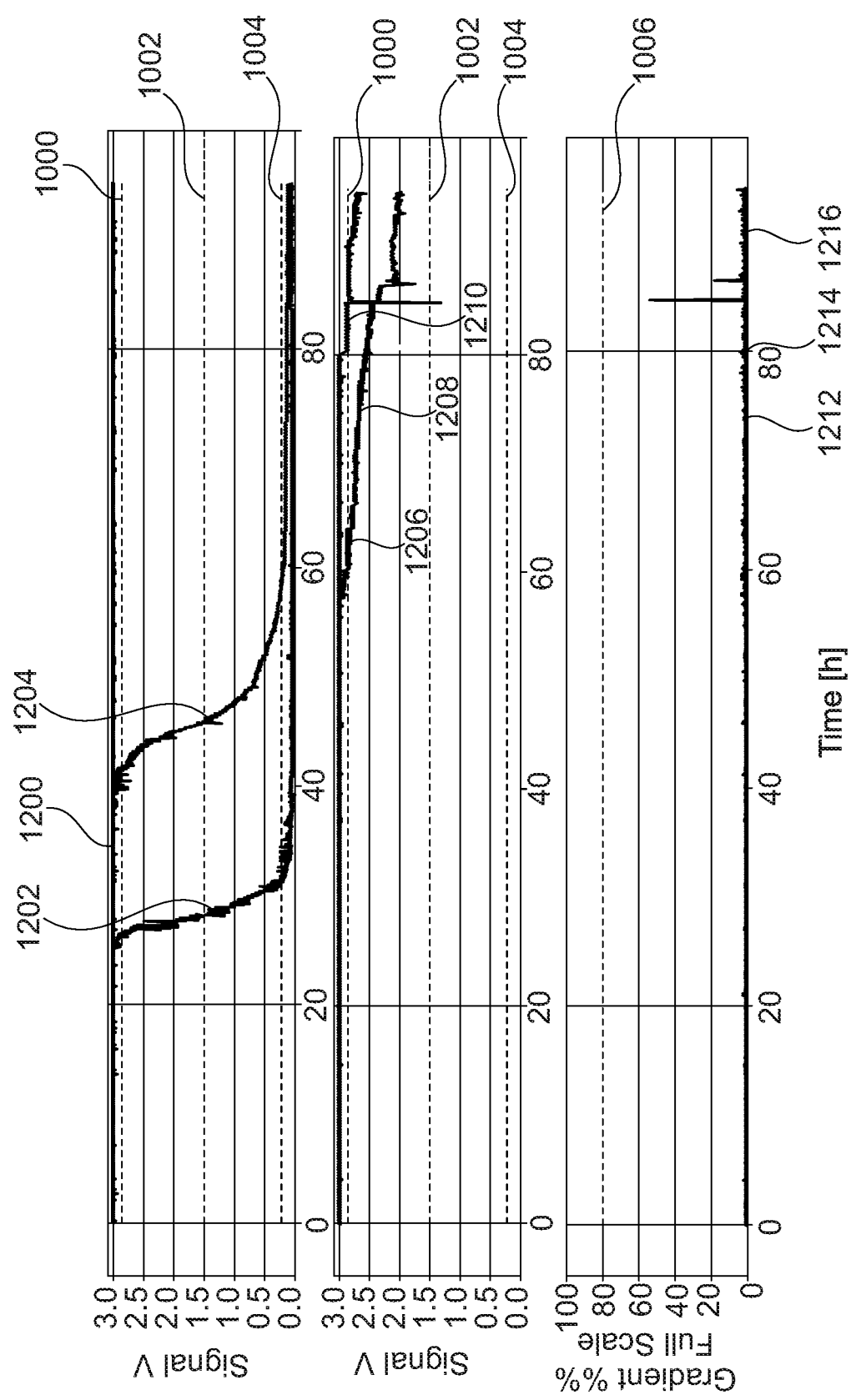
FIG. 15 is an exemplary graphical representation of parameter data as a function of time.

FIG. 15 shows an exemplary graphical representation of parameter data as a function of time. In this example, the parameter data in the y-axis is in Volts and time is in the x-axis. Curve 1202 shows, as a function of time, first parameter data indicative of voltage measured by the first electrode pair of the base plate. Curve 1204 shows, as a function of time, second parameter data indicative of voltage measured by the second electrode pair of the base plate. Curve 1200 shows, as a function of time, third parameter data indicative of voltage measured by the third electrode pair of the base plate. Curves 1206, 1208, 1210 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1212, 1214, 1216 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 15 shows the upper voltage threshold value represented as curve 1000, the medium voltage threshold value represented as curve 1002, the lower voltage threshold value represented as curve 1004, and curve 1006 represents a gradient limit.

Curves 1206, 1208, 1210 as well as curves 1212, 1214, 1216 show that moisture is detected at the proximal side of the first adhesive layer by the fourth electrode pair, the fourth and fifth electrode, and the fifth electrode pair at a time starting at 60*h* until 90*h*. As the three electrode pairs are triggered as shown by the decreases shown by 1206, 1208,

1210 and as the curves 1212, 1214, 1216 show a gradient below 80%, this is indicative of the presence of sweat at the proximal side of the first adhesive layer.

At a time of 30 min, curve 1202 shows that moisture is detected by the first electrode pair as the first parameter data crosses the upper voltage threshold value while curve 1204 shows that moisture is not detected by the second electrode pair as the second parameter data has not crossed the upper voltage threshold value. At this stage, it is determined that the ostomy appliance is in a first operating state.

At time around 40 h, curve 1204 shows that moisture is detected by the second electrode pair as the second parameter data crosses the upper voltage threshold value. At this stage, it is determined that the ostomy appliance is in a second operating state.

Figure 16:
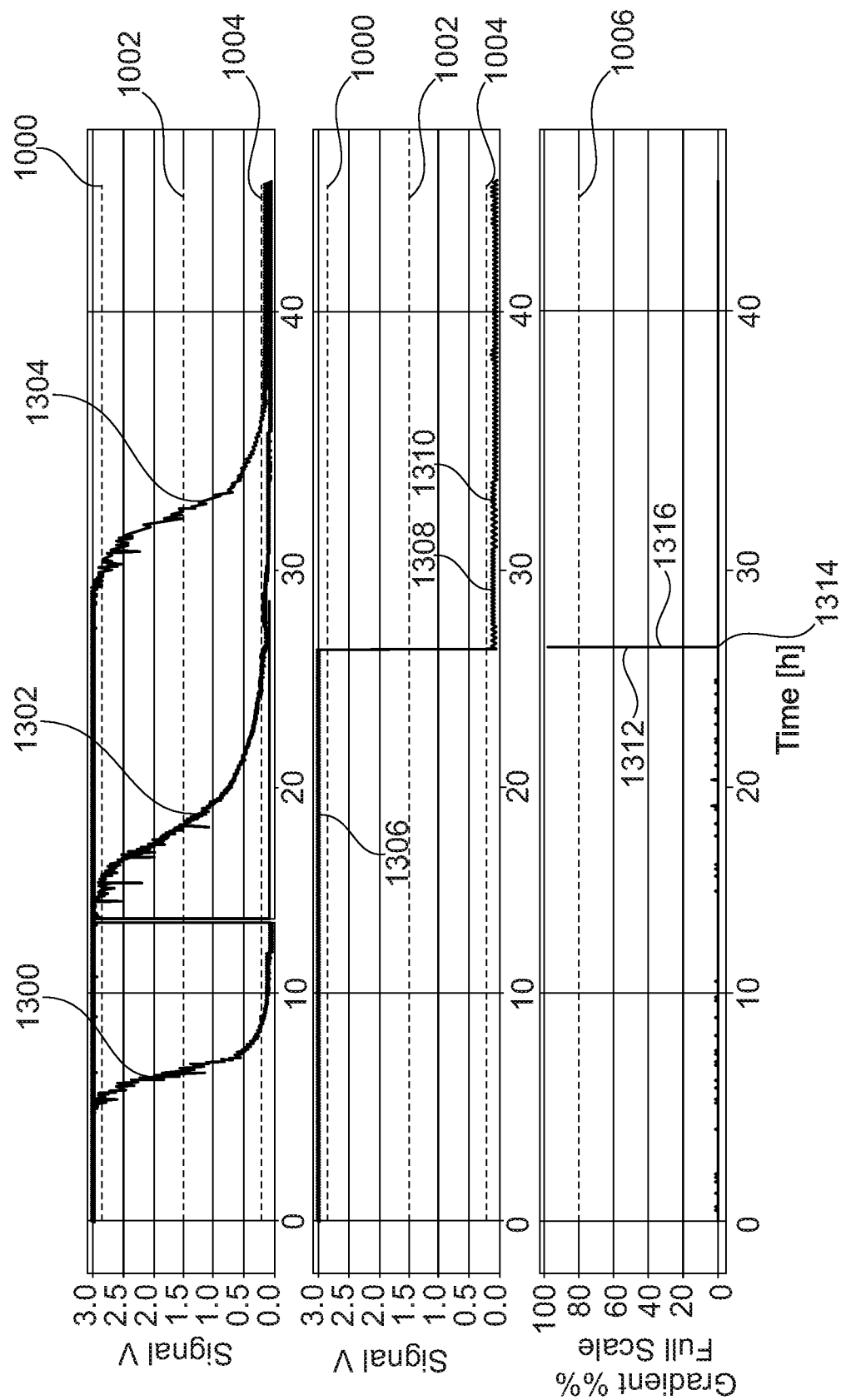
FIG. 16 is an exemplary graphical representation of parameter data as a function of time.

FIG. 16 shows an exemplary graphical representation of parameter data as a function of time. In this example, the parameter data in the y-axis is in Volts and time is in the x-axis. Curve 1300 shows, as a function of time, first parameter data indicative of voltage measured by the first electrode pair of the base plate. Curve 1302 shows, as a function of time, second parameter data indicative of voltage measured by the second electrode pair of the base plate. Curve 1304 shows, as a function of time, third parameter data indicative of voltage measured by the third electrode pair of the base plate. Curves 1306, 1308, 1310 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1312, 1314, 1316 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 16 shows the upper voltage threshold value represented as curve 1000, the medium voltage threshold value represented as curve 1002, the lower voltage threshold value represented as curve 1004, and curve 1006 is a gradient limit.

Curves 1306, 1308, 1310 as well as curves 1312, 1314, 1316 show that moisture is detected at the proximal side of the first adhesive layer by the fourth electrode pair at a time starting at around 25 h. As leakage electrodes (i.e. the fourth electrode pair, the fourth and fifth electrode, and the fifth electrode pair) are trigger as shown by the decreases shown by 1306, 1308, 1310 and as curve 1312, 1314, 1316 show a gradient above 80%, this is indicative of the presence of output at the proximal side of the first adhesive layer. This indicate severe leakage. It may be determined that the ostomy appliance is in a sixth operating state.

At a time of 5 h, curve 1300 shows that moisture is detected by the first electrode pair as the first parameter data crosses the upper voltage threshold value while curve 1302 shows that moisture is not detected by the second electrode pair as the second parameter data has not crossed the upper voltage threshold value. At this stage, it is determined that the ostomy appliance is in a first operating state.

At time around 15 h, curve 1302 shows that moisture is detected by the second electrode pair as the second parameter data crosses the upper voltage threshold value. At this stage, it is determined that the ostomy appliance is in a second operating state.

At time around 30 h, curve 1304 shows that moisture is detected by the third electrode pair as the third parameter data crosses the upper voltage threshold value. In an example where the curves 1306, 1308, 1310 had not dropped below corresponding thresholds, curve 1304 indicates that moisture has reached the third electrode pair, and the present disclosure enables determining that the ostomy appliance is in a third operating state.

Figure 17:
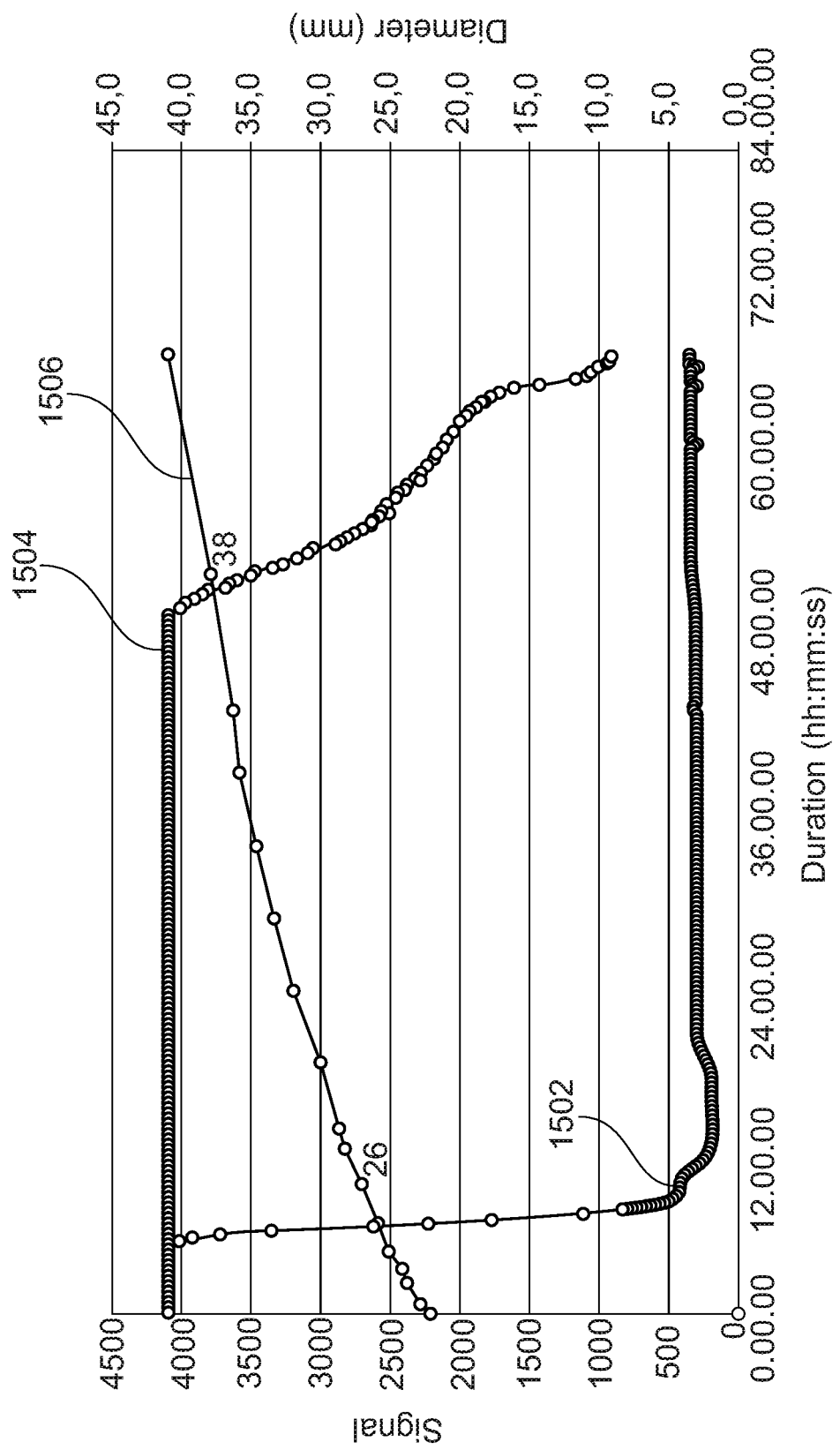
FIG. 17 is an exemplary graphical representation of parameter data as a function of time and a whitening zone diameter as a function of time.

FIG. 17 shows an exemplary graphical representation of parameter data as a function of time and a whitening zone diameter (e.g. related to a radial thickness of a whitening ring surrounding the stomal opening) as a function of time. FIG. 17 illustrates the moisture propagation in the first adhesive layer as a function of time, and illustrates a correlation between parameter data detected by the first electrode pair and the second electrode pair of the base plate and actual moisture on the proximal surface of the first adhesive layer of the base plate. The actual moisture propagation in the first adhesive layer may appear as a whitening zone (e.g. a white ring around the stomal opening) in the first adhesive layer. Moisture affects the first adhesive layer in that the moisture reacts with the composition of the first adhesive layer to form the white ring around the stomal opening, and thereby reduces adhesive performance of the base plate. FIG. 17 is obtained by experiments where water is applied from the stomal opening of the base plate to follow, using the electrodes of the base plate, the radial propagation of moisture leading to radial erosion of the first adhesive layer of the base plate.

Curve 1502 shows, as a function of time, first parameter data indicative of voltage measured by the first electrode pair of the base plate. Curve 1504 shows, as a function of time, second parameter data indicative of voltage measured by the second electrode pair of the base plate. Curve 1506 shows a diameter of the white ring as a function of time. The first parameter data shows a decrease in e.g. voltage measured by the first electrode pair over time. It is also seen that the voltage of the second electrode pair drops at a later time than when the first parameter data shows a decrease in e.g. voltage dropped. This correlates well with the diameter of the white ring which goes from around 25-26 mm when the first electrode pair is triggered (e.g. first parameter data shows a decrease) to 38 mm when the second electrode pair is triggered (second parameter data shows a decrease). This corresponds substantially to the location of the first electrode pair at twice the first radial distance R1, and of the second electrode pair at twice the second radial distance R2.

It is noted that various regions and countries have various routines and recommendations to support optimal use of an ostomy appliance. For example, in regions of Europe, it may be indicated to the user that an ostomy appliance with a base plate as disclosed herein is an optimal state (corresponding to a first operating state) when the radial thickness of the whitening ring is between 0-15 mm (for a user not in compliance with a preferred use), such as between 0-7 mm (for a user in compliance with a preferred use), such as between 0-5 mm (recommended by a nurse).

For example, in Europe, it may be indicated to the user that an ostomy appliance with a base plate as disclosed herein is in suboptimal state (corresponding to a second operating state) and thereby indicate a consideration to change the base plate when the radial thickness of the whitening ring is such as between 5-10 mm (recommended by a nurse), between 7 mm and 10 mm (for a user in compliance with a preferred use), and/or between 15 mm and 30 mm (for a user not in compliance with a preferred use).

For example, in Europe, it may be indicated to the user that an ostomy appliance with a base plate as disclosed herein is in a poor state (corresponding to a third operating state) and indicate a request to change the base plate when the radial thickness of the whitening ring is more than 10 mm (recommended by a nurse), such as more than 15 mm (for a user in compliance with a preferred use), such as more than 30 mm (for a user not in compliance with a preferred use).

For example, in other regions (e.g. America), it may be indicated to the user that an ostomy appliance with a base plate as disclosed herein is an optimal state (corresponding to a first operating state) when the radial thickness of the whitening ring is between 0-20 mm (for a user not in compliance with a preferred use), such as between 0-10 mm (for a user in compliance with a preferred use), such as between 0-10 mm (recommended by a nurse).

For example, in other regions (e.g. America), it may be indicated to the user that an ostomy appliance with a base plate as disclosed herein is in suboptimal state (corresponding to a second operating state) and thereby indicate a consideration to change the base plate when the radial thickness of the whitening ring is such as between 10 mm and 20 mm (recommended by a nurse), between 10 mm and 20 (for a user in compliance with a preferred use), and/or between 20 mm and 40 mm (for a user not in compliance with a preferred use).

For example, in other regions (e.g. America), it may be indicated to the user that an ostomy appliance with a base plate as disclosed herein is in a poor state (corresponding to a third operating state) and indicate a request to change the base plate when the radial thickness of the whitening ring is more than 20 mm (recommended by a nurse), such as more than 20 mm (for a user in compliance with a preferred use), such as more than 40 mm (for a user not in compliance with a preferred use).

The disclosed methods, ostomy appliances, monitor devices, and accessory devices allow to accommodate the regional preferences of user in their use of the ostomy appliance so as to adjust thresholds for the operating states to the regional preference or use.

Figure 18A:
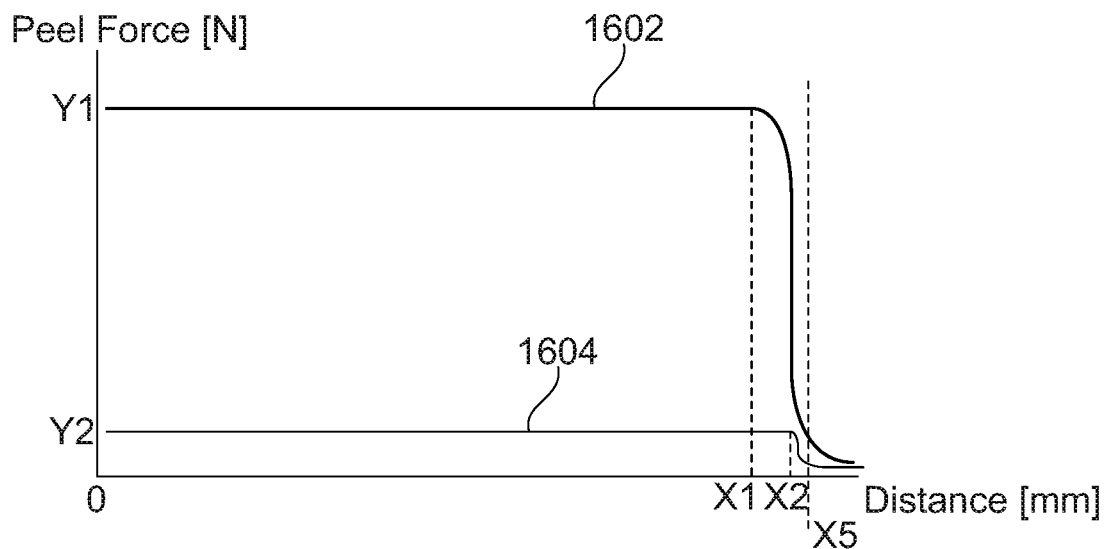
FIGS. 18A-18B are exemplary graphical representations of peel force as a function of a peeling distance travelled by a peeling action exercising the peel force on a first adhesive layer of a base plate.
Figure 18B:
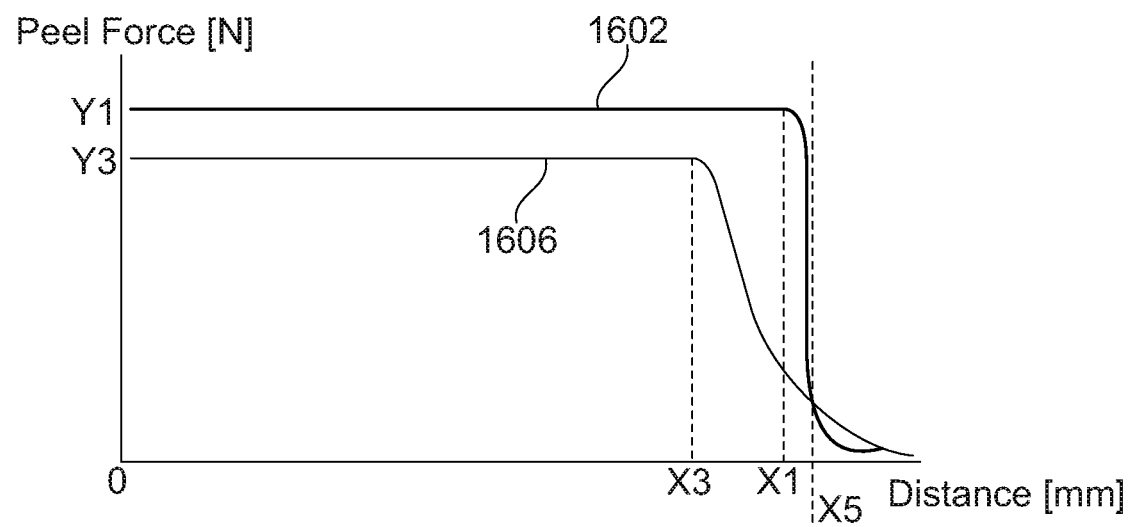
Figure 18B:
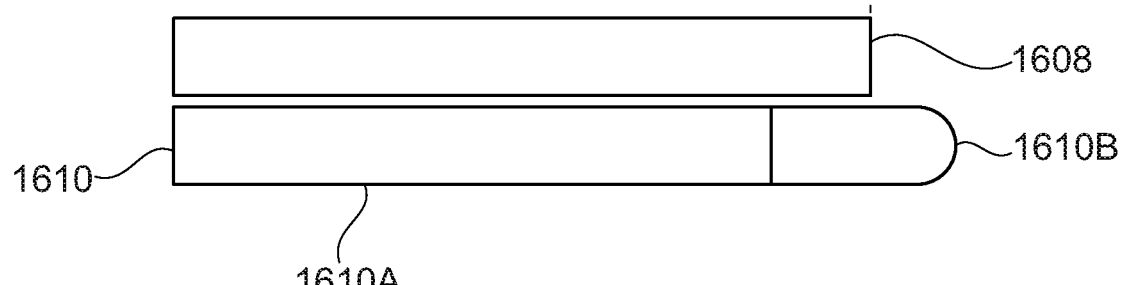

FIGS. 18A-18B shows exemplary graphical representations of peel force as a function of a peeling distance travelled by a peeling action exercising the peel force (e.g. perpendicularly to the proximal (or distal) surface of the first adhesive layer) on a first adhesive layer of a base plate disclosed herein. The peel force relates to a required force to peel the first adhesive layer off the skin surface. The peeling distance is with respect to one end of the first adhesive layer where the peel force starts to be exercised. The peeling distance relates to the size or length of the first adhesive layer and thereby may relate to a size or length of a portion the first adhesive layer affected by moisture and of a portion of the first adhesive layer not affected by moisture. The peel forces illustrated in FIGS. 18A-18B are representative of adhesive performance of the first adhesive layer of the base plate to the skin surface.

Composition of the first adhesive layer of the base plate as disclosed herein in one or more embodiments is formulated to provide adhesion of the base plate to the skin surface of the user when the base plate is worn and to maintain a dry and healthy skin surface. Avoiding maceration of skin when occluding the skin with an adhesive is done by transporting sweat away from the skin and into the first adhesive layer by means of e.g. hydrocolloid types and adhesive (e.g. hydrocolloid adhesives) forming part of an absorbing element of the first adhesive layer.

For example, when the absorbing element is in contact with moisture, (e.g. water, sweat, urine or faeces), the absorbing element absorb the moisture. This reduces the adhesion of the first adhesive layer to the skin.

For example, the first adhesive layer goes from a dry adhesive state with acceptable adhesive performance (e.g. acceptable adhesion and cohesion) in to a wet adhesive state (e.g. reduced or non adhesion and low cohesion gel).

Curve 1602 of FIGS. 18A and 18B shows a peel force applied to the first adhesive layer as a function of a peeling distance travelled by a peeling action exercising the peel force on the first adhesive layer in a dry adhesive state, (e.g. not affected by moisture). The peel force is expressed in Newtons while the peeling distance is expressed in mm. The length of the first adhesive layer in dry adhesive state is illustrated by X5, corresponding to length of the first adhesive layer 1608 in dry adhesive state.

Curve 1602 shows that the peel force applied to the first adhesive layer in a dry adhesive state is equal to Y1 when the peeling distance is less than X1. At X1, the peeling force drops as the peeling distance increases towards X5 and the end of the first adhesive layer.

Curve 1604 of FIG. 18A shows a peel force applied to the first adhesive layer as a function of a peeling distance travelled by a peeling action exercising the peel force on the first adhesive layer in a wet adhesive state, (e.g. affected by moisture to the point of reaching a completely wet adhesive state, where the first adhesive layer has become a gel).

Curve 1604 shows that when the peeling distance is less than X2, the peel force applied to the first adhesive layer in a wet adhesive state is equal to Y2 which has much lower value than Y1. This shows that the adhesive performance of the first adhesive layer is reduced when the first adhesive layer is in a wet adhesive state. At X2, the peeling force drops as the peeling distance increases until the end of the first adhesive layer. It is noted that X2 is larger than X1, because the first adhesive layer in a wet adhesive state extends in volume, and thus in length due to the gelling of the components of the first adhesive layer.

The peel experiment illustrated in FIG. 18A shows a loss of adhesive performance when the first adhesive is in a wet adhesive state.

Curve 1606 of FIG. 18B shows a peel force applied to the first adhesive layer as a function of a peeling distance travelled by a peeling action exercising the peel force on the first adhesive layer illustrated 1610 which comprises a first portion 1610A in a dry adhesive state and a second portion 1610B in a wet adhesive state, (e.g. affected by moisture to the point of reaching a completely wet adhesive state, where the first adhesive layer has become a gel).

Curve 1606 shows that when the peeling distance is less than X3, the peel force applied to the first adhesive layer in a wet adhesive state is equal to Y3 which has lower value than Y1. This shows that the adhesive performance of the first adhesive layer is reduced when the first adhesive layer comprises a portion in a wet adhesive state. At X3, the peeling force drops as the peeling distance increases until the end of the first adhesive layer. It is noted that X3 corresponds to the length of the portion 1610A in dry adhesive state.

The peel experiment illustrated in FIG. 18B shows a loss of adhesive performance when the first adhesive is partly in a wet adhesive state.

Accordingly, FIGS. 18A-18B demonstrate that the operating state determined based on monitor data is indicative of adhesive performance of the base plate.

FIGS. 19A-19B show exemplary graphical representations of a whitening zone diameter (e.g. related to a radial thickness of a whitening ring surrounding the stomal opening) as a function of time. FIGS. 19A-19B illustrates the moisture propagation in the first adhesive layer as a function of time, and illustrates a diametral velocity of the moisture propagation on the proximal surface of the first adhesive layer of the base plate. The actual moisture propagation in the first adhesive layer may appear as a whitening zone (e.g. a white ring around the stomal opening) in the first adhesive layer. FIGS. 19A-19B show measurements of a diameter of the whitening zone as a function of time as moisture propagates. Moisture affects the first adhesive layer in that the moisture reacts with the composition of the first adhesive layer to form the white ring around the stomal opening, and thereby reduces adhesive performance of the base plate.

FIG. 19A is obtained by experiments where water is applied from the stomal opening of the base plate of a first type to measure a velocity of the radial propagation of moisture leading to radial erosion of the first adhesive layer of the base plate of the first type.

FIG. 19B is obtained by experiments where water is applied from the stomal opening of the base plate of a second type to measure a velocity the radial propagation of moisture leading to radial erosion of the first adhesive layer of the base plate of the second type. The second type is different from the first type, in that the composition of the first adhesive layer may be different than the first adhesive layer of the second type when compared to the first type.

Curve 2104 shows, as a function of time, a diameter of the white ring of a base plate of the first type measured from a cut for a stomal opening to the first electrode pair.

Curve 2102 shows a linear approximation of curve 2104, and thereby characterizes the velocity from the cut to the first electrode pair. The linear approximation may be formulated as a linear equation of the type $Y=v01*X+A$, where Y is the diameter of the white ring in millimetres (mm), X is time in hours, v01 is a diametral velocity of propagation of moisture in the base plate of the first type from the cut to the first electrode pair, and A relates to the diameter of the cut. In the experiment illustrated in FIG. 16A, v01=0.6 mm/h and A is 22 (i.e. the cut for the stomal opening has a diameter of 22 mm). Other experiments have shown that v01 may be in the range of 0.5 mm/h to 0.7 mm/h, with an average diametral velocity v01 of 0.65 mm/h for moisture to propagate from the cut to the first electrode pair. To obtain radial velocity V01 for moisture to propagate from the cut to the first electrode pair from the results of FIG. 16A, the diametral velocity v01 is to be divided by two: V01=0.3 mm/h for the illustrated experiment. In one or more embodiments, the radial velocity may range from 0.25 to 0.35 mm/h.

Curve 2106 shows, as a function of time, a diameter of the white ring of a base plate of the first type measured from the first electrode pair to the second electrode pair.

Curve 2108 shows a linear approximation of curve 2106, and thereby characterizes the velocity from the first electrode pair to the second electrode pair. The linear approximation may be formulated as a linear equation of the type $Y=v12*X+B$, where Y is the diameter of the white ring in millimetres (mm), X is time in hours, v12 is a diametral velocity of propagation of moisture in the base plate of the first type from the first electrode pair to the second electrode pair, and B relates to approximate location of the first electrode pair from the center of the stomal opening. In the experiment illustrated in FIG. 19A, v12=0.2 mm/h and B is 27.3 mm (i.e. the first electrode pair is place around 27.3 mm). Other experiments have shown that v12 may be in the range of 0.15 mm/h to 0.22 mm/h, with an average diametral velocity of 0.18 mm/h for moisture to propagate from the first electrode pair to the second electrode pair. To obtain radial velocity V12 for moisture to propagate from the first electrode pair to the second electrode pair from the results of FIG. 19A, the diametral velocity v12 is to be divided by two: V12=0.1 mm/h for the illustrated experiment.

Curve 2112 shows, as a function of time, a diameter of the white ring of a base plate of the second type measured from a cut for a stomal opening to the first electrode pair.

Curve 2110 shows a linear approximation of curve 2112, and thereby characterizes the velocity from the cut to the first electrode pair. The linear approximation may be formulated as a linear equation of the type $Y=v01*X+A$, where Y is the diameter of the white ring in millimetres (mm), X is time in hours, v01 is a diametral velocity of propagation of moisture in the base plate of the second type from the cut to the first electrode pair, and A relates to the diameter of the cut. In the experiment illustrated in FIG. 16B, v01=0.3 mm/h and A is 21.9 (i.e. the cut for the stomal opening has a diameter of 21.9 mm). Other experiments have shown that v01 may be in the range of 0.2 mm/h to 0.32 mm/h, with an average diametral velocity v01 of 0.275 mm/h for moisture to propagate from the cut to the first electrode pair. To obtain radial velocity V01 for moisture to propagate from the cut to the first electrode pair from the results of FIG. 19B, the diametral velocity v01 is to be divided by two: V01=0.15 mm/h for the illustrated experiment. In one or more embodiments, the radial velocity may range from 0.1 to 0.15 mm/h.

Curve 2114 shows, as a function of time, a diameter of the white ring of a base plate of the second type measured from the first electrode pair to the second electrode pair.

Curve 2116 shows a linear approximation of curve 2114, and thereby characterizes the velocity from the first electrode pair to the second electrode pair. The linear approximation may be formulated as a linear equation of the type $Y=v12*X+B$, where Y is the diameter of the white ring in millimetres (mm), X is time in hours, v12 is a diametral velocity of propagation of moisture in the base plate of the second type from the first electrode pair to the second electrode pair, and B relates to approximate location of the first electrode pair from the center of the stomal opening. In the experiment illustrated in FIG. 19B, v12=0.2 mm/h and B is 25.9 mm (i.e. the first electrode pair is place around 25.9 mm). Other experiments have shown that v12 may be in the range of 0.15 mm/h to 0.22 mm/h, with an average diametral velocity of 0.1 mm/h for moisture to propagate from the first electrode pair to the second electrode pair. To obtain radial velocity V12 for moisture to propagate from the first electrode pair to the second electrode pair from the results of FIG. 16B, the diametral velocity v12 is to be divided by two: V12=0.2 mm/h for the illustrated experiment. In one or more embodiments, the radial velocity may range from 0.075 to 0.1 mm/h.

The experiments illustrated in FIGS. 19A-19B correspond substantially with the location of the first electrode pair at twice the first radial distance R1, and of the second electrode pair at twice the second radial distance R2.

The present disclosure exploits the derivable velocities (e.g. velocity data) to determine a future operating state based on monitor data and/or current operating state.

FIG. 20A shows an exemplary graphical representation of first parameter data as a function of time. In this example, the parameter data in the y-axis is in millivolts and time is in the x-axis.

FIG. 20A is obtained by experiments where semi-solid matter with various degrees of dilution is applied from the stomal opening of the base plate to follow, using the first electrode pair of the base plate, the radial propagation of moisture leading to radial erosion of the first adhesive layer of the base plate. Dilution is performed with tap water and semi-solid matter.

The exemplary results of FIG. 20A illustrates and mimics how the moisture content of the output would affect the first parameter data and thereby the operating state. This is done by mixing a semi-solid matter with water to various dilution factors. The content of moisture in real life changes the viscosity of the output and is affected by one or more factors: nutrition (type of food eaten by user, water intake, etc.), medication (e.g. vitamins/supplements, prescriptions, etc.), and health data (e.g. medical conditions of the user, diseases, ostomist, ileostomist, etc.).

Curve 2202 shows, as a function of time, first parameter data indicative of voltage measured by the first electrode pair of the base plate when a mixture of 0% semi-solid matter and 100% tap water is applied from the stomal opening of the base plate.

Curve 2204 shows, as a function of time, first parameter data indicative of voltage measured by the first electrode pair of the base plate when a mixture of 30% semi-solid matter and 70% tap water is applied. Curve 2204A shows, as a function of time, first parameter data indicative of voltage measured by the first electrode pair of the base plate when a mixture of 30% semi-solid matter and 70% tap water is applied.

Curve 2206 shows, as a function of time, first parameter data indicative of voltage measured by the first electrode pair of the base plate when a mixture of 30% semi-solid matter and 70% tap water is applied.

Curve 2208 shows, as a function of time, first parameter data indicative of voltage measured by the first electrode pair of the base plate when a mixture of 50% semi-solid matter and 50% tap water is applied.

Curve 2210 shows, as a function of time, first parameter data indicative of voltage measured by the first electrode pair of the base plate when a mixture of 100% semi-solid matter and 0% tap water is applied.

Curve 2212 shows, as a function of time, first parameter data indicative of voltage measured by the first electrode pair of the base plate when a mixture of 100% semi-solid matter and 0% tap water is applied.

It may be noted that the more diluted the semi-solid matter/output is the earlier the first electrode pair is triggered.

FIG. 20B shows exemplary graphical representations of first parameter data as a function of percentage of semi-solid matter in the mixture applied.

Curve 2214 shows a linear approximation relating the trigger times of the first electrode pair to the percentage of semi-solid matter, and thereby characterizes how the viscosity of the semi-solid matter affects the propagation of moisture in the first adhesive layer. The curve 2214 represents a linear equation with a coefficient of 10.6 with an approximation precision of 87% for the exemplary results. This supports a determination of a future operating state based one or more of: nutrition (type of food eaten by user, water intake, etc.), medication (e.g. vitamins/supplements, prescriptions, etc.), and health data (e.g. medical conditions of the user, diseases, ostomist, ileostomist, etc.).

It may be envisaged that a thin output may be detected based on the early triggering time of the first electrode pair and thereby the future operating state may be determined accordingly.

Due to activity (e.g. sports, bending, movement), experimental results have shown that the operating state may be affected negatively by a reducing factor ranging from 2 to 10 compared to when the user has no or little activity (e.g. a sedentary user), For example, a wear time may be reduced by a factor of 2 to 10 due to an extensive activity.

Embodiments of methods and products (accessory devices) according to the disclosure are set out in the following items:

1. A method, performed in an accessory device, for assisting change of a base plate of an ostomy appliance, wherein the accessory device comprises an interface configured to communicate with one or more devices of an ostomy system, the interface comprising a display, wherein the ostomy system comprises a monitor device, and/or the ostomy appliance configured to be placed on a skin surface of a user, wherein the ostomy appliance comprises a base plate, the method comprising:
    obtaining monitor data from the monitor device;
    determining a current operating state of the ostomy appliance based on the monitor data;
    determining a future operating state of the ostomy appliance based on the monitor data and/or the current operating state; and
    displaying, on the display, a first user interface screen comprising a first primary user interface object representing the current operating state and/or a first secondary user interface object representing the future operating state.

2. Method according to item 1, the method comprising:
    detecting a first input selecting any of the first primary and secondary user interface object;
    in response to detecting the first input, opening an ostomy user application.

3. Method according to item 3, the method comprising:
    in response to opening the ostomy user application, displaying a second user interface screen comprising a second primary user interface object representing the current operating state of the ostomy appliance and a second secondary user interface object representing the future operating state.

4. Method according to any of previous items, wherein obtaining monitor data from a monitor device comprising obtaining the monitor data over a time period.

5. Method according to items 4, wherein determining the current operating state of the ostomy appliance and the future operating state of the ostomy appliance is based on the monitor data received over a time period.

6. Method according to any of the previous items, wherein determining the current operating state of the ostomy appliance and the future operating state of the ostomy appliance is based on one or more previous operating states.

7. Method according to any of items 4-6, wherein the time period includes time period up to and including the current time.

8. Method according to item 3, the method comprising:
    displaying in the second user interface screen third user interface objects representing previous operating states, the current operating state, and one or more future operating states mapped over a time window comprising elapsed time prior to the current time, current time and future time period after the current time.

9. Method according to any of items 3-8, the method comprising:
displaying in the second user interface screen a fifth user interface object indicative of the connection between the monitor device and the base plate.

10. Method according to any of items 3-8, the method comprising:
displaying in the second user interface screen a sixth user interface object indicative of battery status of the monitor device.

11. Method according to any of the previous items, the method comprising:
displaying, on the display, a fourth user interface object;
detecting a second input selecting the fourth user interface object;
in response to detecting the second input, displaying a visual indicator indicating to the user to perform a change of base plate.

12. Method according to item 11, wherein displaying the visual indicator indicating to the user to perform the change of base plate comprises displaying a first prompt indicating to the user to remove the monitor device from the used base plate.

13. Method according to any of the previous items, the method comprising:
detecting, based on the monitor data, removal of the monitor device from the base plate,
updating accordingly the display of the fifth or sixth user interface object to indicate lack of connection between the monitor device and the base plate.

14. Method according to any of items 11-13, wherein displaying the visual indicator indicating to the user to perform the change of base plate comprises displaying a second prompt indicating to the user to apply a new base plate.

15. Method according to any of items 11-14, the method comprising capturing an image of peristomal area of the user.

16. Method according to any of items 11-15, wherein displaying the visual indicator indicating to the user to perform the change of base plate comprises displaying a third prompt indicating to the user to attach the monitor device to the new base plate.

17. Method according to any of the previous items, the method comprising:
detecting, based on the monitor data, attachment of the monitor device to the base plate,
updating accordingly the display of the fifth or sixth user interface object to indicate an established connection between the monitor device and the base plate.

18. Method according to any of the previous items, the method comprising:
determining whether the change of base plate satisfies a success criterion, and in accordance with the determination that the change of base plate satisfies the success criterion, displaying a seventh user interface object indicating that the ostomy system is operational.

19. Method according to item 18, wherein the success criterion comprises a primary success criterion, and wherein when the primary success criterion is satisfied when the monitor device is connected properly to the base plate.

20. Method according to any of items 18-19, wherein the success criterion comprises a secondary success criterion, and wherein when the secondary success criterion is satisfied when the monitor device is connected properly to accessory device.

21. Method according to any of items 18-20, wherein the success criterion is satisfied when the primary success criterion is satisfied, and when the secondary success criterion is satisfied.

22. Method according to any of items 18-21, wherein displaying a seventh user interface object indicating that the ostomy system is operational comprises displaying the seventh user interface object on a home screen, and/or on a lock screen.

23. Method according to any of items 18-22, wherein displaying a seventh user interface object indicating that the ostomy system is operational comprises displaying the seventh user interface object in a third user interface screen of the ostomy user application.

24. Method according to any of the previous items, wherein the first user interface screen comprises a lock screen of the accessory device, and/or a home screen of the accessory device.

25. Method according to any of the previous items, wherein displaying the first user interface screen comprises displaying a first notification.

26. Method according to any of the previous items, the method comprising:
obtaining an operating state of the ostomy appliance;
determining whether the operating state satisfies a change criterion; and
in accordance with the operating state satisfying a change criterion, performing the displaying of the first user interface screen comprising the first user primary interface object and the first secondary user interface object.

27. Method according to any of the previous items, the method comprising:
determining a status of an ostomy inventory of the user, and
displaying on a fourth user interface screen one or more user interface objects representative of the status.

28. An accessory device, wherein the accessory device forms part of an ostomy system, the accessory device comprising:
a memory;
a processor; and
an interface configured to communicate with one or more devices of the ostomy system, the one or more devices comprising a monitor device, and/or an ostomy appliance configured to be placed on a skin surface of a user;
wherein the ostomy appliance comprises a base plate;
wherein the interface is coupled to the processor and the memory,
wherein the interface comprises a display;
wherein the interface is configured to obtain monitor data from the monitor device;
wherein the processor is configured to:
determine a current operating state of the ostomy appliance based on the monitor data;
determine a future operating state of the ostomy appliance based on the monitor data and the current operating state; and
to provide data for display, on the display, a first user interface screen comprising a first primary user interface object representing the current operating state and/or a first secondary user interface object representing the future operating state.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Further, in some embodiments, any two or more of the first, second, third user interface screens are the same user interface screen. In other embodiments, any two or more of the first, second, third user interface screens are different.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 1 ostomy system
2 ostomy appliance
4 base plate
6 monitor device
8 accessory device
10 server device
12 network
14 coupling member
16 coupling ring
18 stoma-receiving opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
218 masking element
218A distal surface of masking element
218B proximal surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element 286A second terminal
288 third terminal element
288A third terminal
290 fourth terminal element
290A fourth terminal
292 fifth terminal element
292A fifth terminal
300 method performed at accessory device
301 obtaining monitor data
301a receiving monitor data
301b retrieving monitor data
301c obtaining monitor data over a time period
302 determining current operating state
303 determining future operating state
304 displaying, on the display of the accessory device, a first user interface screen comprising a first primary user interface object representing the current operating state and/or a first secondary user interface object representing the future operating state
305 detecting a first input selecting any of the first primary user interface object and secondary user interface object
306 opening an ostomy user application in response to detecting the first input
401 memory of accessory device
402 processor of accessory device
403 interface of accessory device
403a display of accessory device
500 first user interface screen
502 first primary user interface object
504 first secondary user interface object
506 additional user interface object representing a first previous operating state
508 additional user interface object representing a second previous operating state
520 second user interface screen
522 second primary user interface object
524 second secondary user interface object
526 user interface object representative of a graph
528 third user interface objects
530 user interface object representing a summary status of the base plate
532 elapsed wear time user interface object
534 recommendation user interface object
536 user interface object to access user settings of the user ostomy application
538 fifth user interface object
540 sixth user interface object
550 user interface screen
552 first prompt
560 user interface screen
562 user interface object prompting the user to change the base plate
570 user interface screen
572 user interface object indicative of current and/or future operating state
580 user interface screen
582 prompt to prepare products for change
590 user interface screen
592 prompt requesting to start by removing the monitor device
594 prompt requesting to remove the monitor device
600 user interface screen
602 user interface object indicating prompt to remove the used base plate and/or used bag
620 user interface screen
622 user interface object
640 user interface screen
642 second prompt indicating to the user to apply a new base plate
644 a user interface object which is an affordance to capture an image
660 user interface screen
662 user interface object to indicate to the user to attach the monitor device to the new base plate
664 third prompt to indicate to the user to attach the monitor device to the new base plate
1000 curve representing the upper voltage threshold value
1002 curve representing the medium voltage threshold value
1004 curve representing the lower voltage threshold value
1006 curve representing a gradient limit
1100 curve showing, as a function of time, first parameter data indicative of voltage measured by the first electrode pair of the base plate
1102 curve showing, as a function of time, second parameter data indicative of voltage measured by the second electrode pair of the base plate
1104 curve showing, as a function of time, third parameter data indicative of voltage measured by the third electrode pair of the base plate
1108 curve showing, as a function of time, fourth primary parameter indicative of voltage measured by the fourth electrode pair of the base plate
1110 curve showing, as a function of time, a gradient of fourth primary parameter indicative of voltage gradient
1112 curve showing, as a function of time, a gradient of fourth secondary parameter indicative of voltage gradient measured
1114 curve showing, as a function of time, a gradient of fourth tertiary parameter indicative of voltage gradient measured
1116 curve showing, as a function of time, a fourth secondary parameter indicative of voltage measured
1118 curve showing, as a function of time, a fourth tertiary parameter indicative of voltage measured
1200 curve showing, as a function of time, third parameter data indicative of voltage measured by the third electrode pair of the base plate
1202 curve showing, as a function of time, first parameter data indicative of voltage measured by the first electrode pair of the base plate
1204 curve showing, as a function of time, second parameter data indicative of voltage measured by the second electrode pair of the base plate
1206 curve showing, as a function of time, a fourth primary parameter indicative of voltage measured by the fourth electrode pair of the base plate
1208 curve showing, as a function of time, a fourth secondary parameter indicative of voltage measured
1210 curve showing, as a function of time, a fourth tertiary parameter indicative of voltage measured
1212 curve showing, as a function of time, a gradient of fourth primary parameter indicative of voltage gradient measured by the fourth electrode pair of the base plate
1214 curve showing, as a function of time, a gradient of fourth secondary parameter data indicative of voltage gradient measured
1216 curve showing, as a function of time, a gradient of fourth tertiary parameter indicative of voltage gradient measured
1300 curve showing, as a function of time, first parameter data indicative of voltage measured by the first electrode pair of the base plate 1302 curve showing, as a function of time, second parameter data indicative of voltage measured by the second electrode pair of the base plate 1304 curve showing, as a function of time, third parameter data indicative of voltage measured by the third electrode pair of the base plate 1306 curve showing, as a function of time, a fourth primary parameter indicative of voltage measured by the fourth electrode pair of the base plate 1308 curve showing, as a function of time, a fourth secondary parameter indicative of voltage measured 1310 curve showing, as a function of time, a fourth tertiary parameter indicative of voltage measured 1312 curve showing, as a function of time, a gradient of fourth primary parameter indicative of voltage gradient measured by the fourth electrode pair of the base plate 1314 curve showing, as a function of time, a gradient of fourth secondary parameter indicative of voltage gradient measured 1316 curve showing, as a function of time, a gradient of fourth tertiary parameter indicative of voltage gradient measured 1502 curve showing, as a function of time, first parameter data indicative of voltage measured by the first electrode pair of the base plate 1504 curve showing, as a function of time, second parameter data indicative of voltage measured by the second electrode pair of the base plate 1506 curve showing a diameter of the white ring as a function of time 1602 curve showing peel force applied to the first adhesive layer in a dry adhesive state as a function of peeling distance 1604 a peel force applied to the first adhesive layer as a function of a peeling distance travelled by a peeling action exercising the peel force on the first adhesive layer in a wet adhesive state 1606 a peel force applied to the first adhesive layer as a function of a peeling distance travelled by a peeling action exercising the peel force on the first adhesive layer partially wet 1608 length of the first adhesive layer 1608 in dry adhesive state 1610 the first adhesive layer which comprises a first portion in a dry adhesive state and a second portion in a wet adhesive state 1610A a first portion in a dry adhesive state 1610B a second portion in a wet adhesive state 2104 curve showing a function of time, a diameter of the white ring of a base plate of the first type measured from a cut for a stomal opening to the first electrode pair 2102 a linear approximation of curve 2104

2106 curve showing, as function of time, a diameter of the white ring of a base plate of the first type measured from the first electrode pair to the second electrode pair 2108 a linear approximation of curve 2106

2110 a linear approximation of curve 2112

2112 curve showing, as function of time, a diameter of the white ring of a base plate of the second type measured from a cut for a stomal opening to the first electrode pair 2114 curve showing, as a function of time, a diameter of the white ring of a base plate of the second type measured from the first electrode pair to the second electrode pair 2116 a linear approximation of curve 2114

2202 curve showing, as a function of time, first parameter data 2204 curve showing, as a function of time, first parameter data 2204A curve showing, as a function of time, first parameter data indicative of voltage measured by the first electrode pair of the base plate when a mixture of 30% semi-solid matter and 70% tap water is applied 2206 curve showing, as a function of time, first parameter data indicative of voltage measured by the first electrode pair of the base plate when a mixture of 30% semi-solid matter and 70% tap water is applied 2208 curve showing, as a function of time, first parameter data indicative of voltage measured by the first electrode pair of the base plate when a mixture of 50% semi-solid matter and 50% tap water is applied 2210 curve showing, as a function of time, first parameter data indicative of voltage measured by the first electrode pair of the base plate when a mixture of 100% semi-solid matter and 0% tap water is applied 2212 curve showing, as a function of time, first parameter data indicative of voltage measured by the first electrode pair of the base plate when a mixture of 100% semi-solid matter and 0% tap water is applied 2214 curve showing a linear approximation relating the trigger times of the first electrode pair to the percentage of semi-solid matter

The invention claimed is:

1. A method, performed in an accessory device, for a base plate of an ostomy appliance, wherein the accessory device comprises an interface configured to communicate with one or more devices of an ostomy system, the interface comprising a display, wherein the ostomy system comprises a monitor device, and/or the ostomy appliance configured to be placed on a skin surface of a user, wherein the ostomy appliance comprises the base plate, the method comprising:
    obtaining monitor data from the monitor device;
    determining a current operating state of the base plate based on the monitor data, the current operating state indicative of current adhesive performance of the base plate;
    determining a future operating state of the base plate based on the monitor data and/or the current operating state, the future operating state indicative of future adhesive performance of the base plate; and
    displaying, on the display, a first user interface screen comprising a first primary user interface object representing the current operating state and/or a first secondary user interface object representing the future operating state.

2. The method according to claim 1, the method comprising:
    detecting a first input selecting any of the first primary and secondary user interface object; and
    in response to detecting the first input, opening an ostomy user application.

3. The method according to claim 2, the method comprising:
    in response to opening the ostomy user application, displaying a second user interface screen comprising a second primary user interface object representing the current operating state of the base plate and a second secondary user interface object representing the future operating state.

4. The method according to claim 1, wherein obtaining monitor data from a monitor device comprising obtaining the monitor data over a time period.

5. The method according to claim 4, wherein determining the current operating state of the base plate and the future operating state of the base plate is based on the monitor data received over a time period.

6. The method according to claim 1, wherein determining the current operating state of the base plate and the future operating state of the base plate is based on one or more previous operating states.

7. The method according to claim 4, wherein the time period includes time period up to and including the current time.

8. The method according to claim 3, the method comprising:
displaying, in the second user interface screen, third user interface objects representing previous operating states, the current operating state, and one or more future operating states mapped over a time window comprising elapsed time prior to the current time, current time and future time period after the current time.

9. The method according to claim 3, the method comprising:
displaying, in the second user interface screen, a fifth user interface object indicative of the connection between the monitor device and the base plate.

10. The method according to claim 3, the method comprising:
displaying, in the second user interface screen, a sixth user interface object indicative of battery status of the monitor device.

11. The method according to claim 1, the method comprising:
displaying, on the display, a fourth user interface object;
detecting a second input selecting the fourth user interface object; and
in response to detecting the second input, displaying a visual indicator indicating to the user to perform a change of base plate.

12. The method according to claim 11, wherein displaying the visual indicator indicating to the user to perform the change of base plate comprises displaying a first prompt indicating to the user to remove the monitor device from the used base plate.

13. The method according to claim 1, the method comprising:
detecting, based on the monitor data, removal of the monitor device from the base plate, and
updating accordingly the display of the fifth or sixth user interface object to indicate lack of connection between the monitor device and the base plate.

14. The method according to claim 11, wherein displaying the visual indicator indicating to the user to perform the change of base plate comprises displaying a second prompt indicating to the user to apply a new base plate.

15. The method according to claim 11, the method comprising capturing an image of peristomal area of the user.

16. The method according to claim 11, wherein displaying the visual indicator indicating to the user to perform the change of base plate comprises displaying a third prompt indicating to the user to attach the monitor device to the new base plate.

17. The method according to claim 1, the method comprising:
detecting, based on the monitor data, attachment of the monitor device to the base plate, and
updating accordingly the display of the fifth or sixth user interface object to indicate an established connection between the monitor device and the base plate.

18. The method according to claim 11, the method comprising:
determining whether the change of base plate satisfies a success criterion, and
in accordance with the determination that the change of base plate satisfies the success criterion, displaying a seventh user interface object indicating that the ostomy system is operational.

19. The method according to claim 18, wherein the success criterion comprises a primary success criterion, and wherein when the primary success criterion is satisfied when the monitor device is connected properly to the base plate.

20. The method according to claim 18, wherein the success criterion comprises a secondary success criterion, and wherein when the secondary success criterion is satisfied when the monitor device is connected properly to accessory device.

21. The method according to claim 18, wherein the success criterion is satisfied when the primary success criterion is satisfied, and when the secondary success criterion is satisfied.

22. The method according to claim 18, wherein displaying a seventh user interface object indicating that the ostomy system is operational comprises displaying the seventh user interface object on a home screen, and/or on a lock screen.

23. The method according to claim 18, wherein displaying a seventh user interface object indicating that the ostomy system is operational comprises displaying the seventh user interface object in a third user interface screen of the ostomy user application.

24. The method according to claim 1, wherein the first user interface screen comprises a lock screen of the accessory device, and/or a home screen of the accessory device.

25. The method according to claim 1, wherein displaying the first user interface screen comprises displaying a first notification.

26. The method according to claim 1, the method comprising:
obtaining an operating state of the base plate;
determining whether the operating state satisfies a change criterion; and
in accordance with the operating state satisfying a change criterion, performing the displaying of the first user interface screen comprising the first primary user interface object and the first secondary user interface object.

27. The method according to claim 1, the method comprising:
determining a status of an ostomy inventory of the user, and
displaying on a fourth user interface screen one or more user interface objects representative of the status.

28. An accessory device, wherein the accessory device forms part of an ostomy system, the accessory device comprising:
a memory;
a processor; and
an interface configured to communicate with one or more devices of the ostomy system, the one or more devices comprising a monitor device, and/or an ostomy appliance configured to be placed on a skin surface of a user;
wherein the ostomy appliance comprises a base plate;
wherein the interface is coupled to the processor and the memory,
wherein the interface comprises a display;
wherein the interface is configured to obtain monitor data from the monitor device;

wherein the processor is configured to:
  determine a current operating state of the base plate based on the monitor data;
  determine a future operating state of the base plate based on the monitor data and the current operating state; and
  to provide data for display, on the display, a first user interface screen comprising a first primary user interface object representing the current operating state and/or a first secondary user interface object representing the future operating state.

* * * * *